US005955280A

United States Patent [19]
Vidal et al.

[11] Patent Number: 5,955,280
[45] Date of Patent: Sep. 21, 1999

[54] REVERSE TWO-HYBRID SYSTEM

[75] Inventors: Marc Vidal, Boston, Mass.; Jef D. Boeke, Baltimore, Md.; Ed Harlow, Boston, Mass.

[73] Assignees: The General Hospital Corporation, Boston, Mass.; The Johns Hopkins University, Baltimore, Md.

[21] Appl. No.: 08/923,274

[22] Filed: Sep. 4, 1997

Related U.S. Application Data

[63] Continuation of application No. 08/420,525, Apr. 11, 1995, abandoned.
[51] Int. Cl.$^6$ .............................. C07H 21/04; C12N 1/19; C12N 5/10; C12Q 1/68
[52] U.S. Cl. .................. 435/6; 435/254.2; 435/320.1; 435/325; 536/23.1; 536/24.1
[58] Field of Search .............................. 435/6, 7.1, 252.1, 435/252.3, 254.2, 254.21, 255.1, 255.2, 320.1, 325; 536/23.1, 23.4, 24.1

[56] References Cited

U.S. PATENT DOCUMENTS

| | | |
|---|---|---|
| 5,283,173 | 2/1994 | Fields et al. . |
| 5,580,736 | 12/1996 | Brent et al. ................................. 435/6 |
| 5,610,015 | 3/1997 | Wickens et al. ............................ 435/6 |
| 5,695,941 | 12/1997 | Brent et al. ................................. 435/6 |

FOREIGN PATENT DOCUMENTS

| | | |
|---|---|---|
| WO 92/05286 | 4/1992 | WIPO . |
| WO 94/02588 | 2/1994 | WIPO . |
| WO 94/10300 | 6/1994 | WIPO . |
| WO 94/17101 | 8/1994 | WIPO . |
| WO 96/02561 | 2/1996 | WIPO . |

OTHER PUBLICATIONS

Le Douarin et al., "A New Version of the Two–Hybrid Assay For Detection of Protein–protein Interactions," Mar. 11, 1995, Nucl. Acids Res. 23: 876–878.

U.S. Patent Application No. 08/783,534, filed Jan. 14, 1997, Brent et al.

C.A. Leanna et al., "The Reverse Two–Hybrid System: A Genetic Scheme for Selection Against Specific Protein/Protein Interactions", 1996 Oxford University Press, Nucleic Acids Research, 1996, vol. 24, No. 17, 3341–3347.

D.J. SenGupta et al., "A Three–Hybrid System to Detect RNA–Protein Interactions In Vivo", Genetics, vol. 93, pp. 8496–8501, Aug. 1996.

S.L. Mansour et al., "Disruption of the Proto–Oncogene int–2 in Mouse Embryo–Derived Stem Cells: A General Strategy for Targeting Mutations to Non–Selectable Genes", Nature, vol. 336, Nov. 24, 1985, pp. 347–352.

Hai–Ling Hsu et al., "Formation of In Vivo Complexes Between the TAL1 and E2A Polypeptides of Leukemic T Cells", Proc. Natl. Acad. Sci. USA, Medical Sciences, vol. 91, Apr. 1994, pp. 3181–3185.

Alani et al., "A Method for Gene Disruption That Allows Repeated Use of URA3 Selection in the Construction of Multiply Disrupted Yeast Strains", Genetics, 116:541–545, 1987.

Bartel et al., "BioFeedback", BioTechniques, 14:920–924, 1993.

Baudin et al., "A Simple and Efficient Method for Direct Gene Deletion in *Saccharomyces Cerevisae*", Nucleic Acids Research, 21:3329–3330, 1993.

Berger et al., "Genetic Isolation of ADA2: A Potential Transcriptional Adaptor Required for Function of Certain Acidic Activation Domains", Cell, 70:251–265, 1992.

Boeke et al., "A Positive Selection for Mutants Lacking Orotindine–5'–Phosphate Decarboxylase Activity In Yeast: 5–Fluoro–Orotic Acid Resistance", Mol Gen Genet, 197:345–346, 1984.

George Boguslawski, "Effects of Polymyxin B Sulfate and Polymyxin B Nonapeptide On Growth and Permeability of the Yeast *Saccharomyces Cerevisiae*", Mol. Gen. Genet, 199:401–405, 1985.

George Boguslawski, "Polymyxin B Nonapeptide Inhibits Mating in *Saccharomyces Cerevisiae*" Antimicrobial Agents and Chemotherapy, 29:330–332, 1986.

Buckingham et al., "Nucleotide Sequence and Promoter Analysis of SPO13, a Meiosis–specific Gene of *Saccharomyces Cerevisiae*", Proc. Natl. Acad. Sci., 87:9406–9410, 1990.

Chalfie et al., "Green Fluorescent Protein as a Marker for Gene Expression", Science, 263:802–805, 1994.

Chevray et al., "Protein Interaction Cloning in Yeast: Identification of Mammalian Proteins that React with the Leucine Zipper of Jun", Proc. Natl. Acad. Sci., 89:5789–5793, 1992.

Chien et al., "The Two–Hybrid System: A Method to Identify and Clone Genes for Proteins that Interact with Protein of Interest", Proc. Natl. Acad. Sci., 88:9578–9582, 1991.

Fields et al., "a Novel Genetic System to Detect Protein–Protein Interactions", Nature, 340:245–246, 1989.

Ingles et al., "Reduced Binding of TFIID to Transcriptionally Compromised Mutants of VP16", Nature, 351:588–590, 1991.

Durfee et al., "The Retinoblastoma Protein Associates with the Protein Phosphatase Type 1 Catalytic Subunit", Genes & Development, 7:555–569, 1993.

Helin, et al., "Inhibition of E2F–1 Transactivation by Direct Binding of the Retinoblastoma Protein", Molecular and Cellular Biology, 13:6501–6508, 1993.

(List continued on next page.)

*Primary Examiner*—George C. Elliott
*Assistant Examiner*—Robert Schwartzman
*Attorney, Agent, or Firm*—Fish & Richardson P.C.

[57] ABSTRACT

Disclosed are methods for identifying molecular interactions (e.g., protein/protein, protein/DNA, protein/RNA, or RNA/RNA interactions). All of the methods within the invention employ counterselection and at least two hybrid molecules. Molecules which interact reconstitute a transcription factor and direct expression of a reporter gene, the expression of which is then assayed. Also disclosed are genetic constructs which are useful in practicing the methods of the invention.

114 Claims, 25 Drawing Sheets

OTHER PUBLICATIONS

Hiebert et al., "The Interaction of RB with E2F Coincides with an Inhibition of the Transcriptional Activity of E2F", Genes & Development, 6:177–185, 1992.

Hope et al., "Functional Dissection of a Eukaryotic Transcriptional Activator Protein, GCN4 of Yeast", Cell, 46:885–894, 1986.

Kumar et al., "Functional Domains of the Human Estrogen Receptor", Cell, 51:941–951, 1987.

Lillie et al., Transcription Activation by the Adenovirus E1a Protein, Nature, 338:39–44, 1989.

Luche et al., "A Cis–cting Element Present in Multiple Genes Serves as a Repressor Protein Binding Site for the Yeast CARI Gene", Molecular and Cellular Biology, 10:3884–3895, 1990.

Ma et al., "A New Class of Yeast Transcriptional Activators", Cell, 51:113–119, 1987.

Pierrat et al., "Functional Analysis of the Human Estrogen Receptor Using a Phenotypic Transactivation Assay in Yeast", Gene, 119:237–245, 1992.

Muhlrad et al., "A Rapid Method for Localized Mutagenesis of Yeast Genes", Yeast, 8:79–82, 1992.

Rose et al., "Structure and Function of the Yeast URA3 Gene: Expression in *Escherichia Coli*", Gene, 29:113–124, 1984.

Rose et al., "Identification of a Ty Insertion Within the Coding Sequence of the *S. Cerevisiae* URA3 Gene", Mol. Gen. Genet, 193:557–560, 1984.

Rodney J. Rothstein, "One Step Gene Disruption in Yeast", Methods in Enzymology, 101:202–211, 1983.

Sardet et al., "E2F–4 and E2F–5, Two Members of the E2F Family, are Expressed in the Early Phases of the Cell Cycle", Proc. Natl. Acad. Sci., 92:2403–2407, 1995.

Sikorski et al., "A System of Shuttle Vectors and Yeast Host Strains Designed for Efficient Manipulation of DNA in *Saccharomyces Cerevisiae*", Genetics, 122:19–27, 1989.

Sikorski et al., "In Vitro Mutagenesis and Plasmid Shuffling: From Cloned Gene to Mutant Yeast", Methods In Enzymology, 194:302–319, 1991.

Strich et al., "UME6 is a Key Regulator of Nitrogen Repression and Meiotic Development", Genes & Development, 8:796–810, 1994.

Vidal et al., "Identification of Essential Nucleotides in an Upstream Repressing Sequence of *Saccharomyces Cerevisiae* by Selection for Increased Expression of TRK2", Proc. Natl. Acad. Sci., 92:2370–2374, 1995.

Vidal et al., "RPDI (SIN3/UME4) Is Required for Maximal Activation and Repression of Diverse Yeast Genes", Molecular and Cellular Biology, 11:6306–6316, 1991.

Whyte et al., "Association Between an Oncogene and an Anti–oncogene: The Adenovirus E1A Proteins Bind to the Retinoblastoma Gene Product", Nature, 334:124–129, 1988.

Yang et al., "Protein–peptide Interactions Analyzed with the Yeast Two–hybrid System", Nucleic Acid Research, 23:1152–1156, 1995.

Harper et al. (1993) The p21 Cdk–interacting protein Cip1 is a potent inhibitor of G1 cyclin–dependent kinases. Cell 75:805–816, Nov. 1993.

Bartel et al. (1993) Using the Two–hybrid system to detect protein–protein interactions. In: Cell Interact. Dev. D.A. Hartley (Ed.), IRL, Oxford, UK, pp. 153–179.

Mendelsohn et al. (1994) Applications of interaction traps/two–hybrid systems to biotechnology research. Curr. Opin. Biotechnol. 5:482–486, Oct. 1994.

Bendixen et al. (1994) A yeast mating–selection scheme for detection of protein–protein interactions. Nucleic Acids Res. 22:1778–1779, May 1994.

| DB-X | Total | His+ | Retested | Known interacting | "Novel" interacting | False positive |
|---|---|---|---|---|---|---|
| None | 1x10⁶ | 1 | 0 | | | |
| p130 | 5x10⁵ | 19 | 9 | 0 | 5→2 | |
| DP1 | 2x10⁵ | 7 | 7 | 6→2 | 1→1 | |
| pRb | 1x10⁶ | 20 | 0 | | | |
| p35 | 1x10⁶ | 20 | 8 | 0 | 8→2 | 0 |
| CDK3 | 1x10⁶ | 38 | 16 | | | |
| CDK3 | 1x10⁶ | 38 | 16 | | | |
| DCC1 | 3x10⁶ | 81 | 23 | 0 | | |
| Zebu | 1x10⁶ | 81 | 23 | | | |

FIG. 11

In vitro mutagenic PCR reaction

In vivo gap repair

FIG. 21

MARKED BOX 2

| (SEQ ID NO:) | 283 | | | | | | | | | | | | | | | | | | 301 | |
|---|---|---|---|---|---|---|---|---|---|---|---|---|---|---|---|---|---|---|---|---|
| (11) | Q | I | N | L | K | S | H | S | G | P | I | H | V | L | L | N | K | | | E2F5 |
| (12) | Q | I | H | L | K | S | V | S | G | P | I | E | V | L | V | N | K | | | E2F4 |
| (13) | Q | I | H | L | A | S | T | Q | G | P | I | E | V | L | L | C | P | E | | E2F3 |
| (14) | Q | I | Y | L | K | S | T | Q | G | P | I | E | V | Y | L | C | P | E | | E2F2 |
| (15) | Q | I | S | L | K | S | K | Q | G | P | I | D | V | F | L | C | P | E | | E2F1 |
| (16) | T | | | | | | | | P | | | G | | | | | | | | E2F1-20 |
| (17) | T | | | | | | | | | | | | | | | | | | | E2F1-30 |
| (18) | | | | | | | | | | | | | | | | | | | | E2F1-32 |
| (19) | N | | | | | | | | | | | | | | | | | | | E2F1-31 |
| | – | – | – | – | – | – | – | – | – | – | – | – | – | – | – | – | – | – | – | E2F1-65 |

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (xi) SEQUENCE DESCRIPTION: SEQ ID NO:1:

```
GAAGGTTAAT GTGGCTGTGG TTTCAGGGTC CATAAAGCTT GTCCTGGAAG TCTCATGGAG      60
```

(2) INFORMATION FOR SEQ ID NO:2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:2:

```
TCAGGATCCC TAGGTTCCTT TGTTACTTCT TCCG                                34
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

```
GCGAGGCATA TTTATGGTGA AGG                                            23
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

```
CATTTCCGTG CAAGGTACTA AC                                             22
```

(2) INFORMATION FOR SEQ ID NO:5:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:5:

```
AAGCTTATGC CCAAGAAGAA GCGGAAGGTC TCGAGGTCGA CCCCGGGAAT TCAG           54
```

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Met Pro Lys Lys Lys Arg Lys Val Ser Arg Ser Thr
1               5                   10
```

(2) INFORMATION FOR SEQ ID NO:7:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (xi) SEQUENCE DESCRIPTION: SEQ ID NO:7:

```
GTATCGTCGA GGTCGACCCC GGGAATTCAG ATCTACTAGT GCGGCCGCTA AGTAAGTAAG     60
```

ACGTCGAGCT CTAAGTAAGT AACGGCCGCC ACCGCGGTGG AGCTTT    106

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

Val Ser Ser Arg Ser Thr Pro Gly Ile Gln Ile Tyr
1               5                   10

(2) INFORMATION FOR SEQ ID NO:9:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (xi) SEQUENCE DESCRIPTION: SEQ ID NO:9:

AAAGAGGGTG GGTCGACCCC GGGAATTCAG ATCTACTAGT GCGGCCGCTA AGTAAGTAAG    60

ACGTCGAGCT CTAAGTAAGT AACGGCCGCC ACCGCGGTGG AGCTTT    106

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:10:

Lys Glu Gly Gly Ser Thr Pro Gly Ile Gln Ile Tyr
1               5                   10

(2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:11:

Gln Ile Asn Leu Lys Ser His Ser Gly Pro Ile His Val Leu Leu Ile
1               5                   10                  15

Asn Lys (2) INFORMATION FOR SEQ ID NO:12:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:12:

```
Gln Ile His Leu Lys Ser Val Ser Gly Pro Ile Glu Val Leu Leu Val
1               5                   10                  15

Asn Lys
```

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:13:

```
Gln Ile His Leu Ala Ser Thr Gln Gly Pro Ile Glu Val Tyr Leu Cys
1               5                   10                  15

Pro Glu
```

(2) INFORMATION FOR SEQ ID NO:14:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

```
Gln Ile Tyr Leu Lys Ser Thr Gln Gly Pro Ile Glu Val Tyr Leu Cys
1               5                   10                  15

Pro Glu
```

(2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:15:

```
Gln Ile Ser Leu Lys Ser Lys Gln Gly Pro Ile Asp Val Phe Leu Cys
1               5                   10                  15

Pro Glu
```

(2) INFORMATION FOR SEQ ID NO:16:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:16:

```
Gln Thr Ser Leu Lys Ser Lys Gln Gly Pro Ile Asp Val Phe Leu Cys
1               5                   10                  15

Pro Glu
```

(2) INFORMATION FOR SEQ ID NO:17:

```
        (i) SEQUENCE CHARACTERISTICS:
            (A) LENGTH: 18 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:17:

Gln Ile Ser Leu Lys Ser Lys Pro Gly Pro Ile Gly Val Phe Leu Cys
1               5                   10                  15

Pro Glu (2) INFORMATION FOR SEQ ID NO:18:

(i) SEQUENCE CHARACTERISTICS:
            (A) LENGTH: 18 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:18:

Gln Thr Ser Leu Lys Ser Lys Gln Gly Pro Ile Asp Val Phe Leu Cys
1               5                   10                  15

Pro Glu (2) INFORMATION FOR SEQ ID NO:19:

(i) SEQUENCE CHARACTERISTICS:
            (A) LENGTH: 18 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:19:

Gln Asn Ser Leu Lys Ser Lys Gln Gly Pro Ile Asp Val Phe Leu Cys
1               5                   10                  15

Pro Glu
```

REVERSE TWO-HYBRID SYSTEM

This application is a continuation of U.S. application Ser. No. 08/420,525, filed Apr. 11, 1995, abandoned.

STATEMENT AS TO FEDERALLY SPONSORED RESEARCH

This invention was made at least in part with funds from the Federal government, and the government therefor has certain rights in the invention.

BACKGROUND OF THE INVENTION

This invention relates to in vivo methods for characterizing interactions between molecules (e.g., protein and/or RNA molecules).

Numerous biologically important functions involve transient interactions between DNA molecules and proteins, RNA molecules and proteins, two or more proteins or RNA molecules, or ligands and receptors. For example, during most of the cell cycle, the tumor suppressor gene product pRb binds to the transcription factor E2F and represses its activity. E2F activity is provided by a family of at least seven proteins. The members of one subfamily (E2F-1, -2, -3, -4, and -5) form heterodimers with the members of another subfamily (DP-1 and -2). These heterodimers bind to the promoter of target genes and activate their transcription at certain stages of the cell cycle.

The transcriptional activity of the E2F/DP complexes can be repressed by any of several functionally related proteins termed the "pocket" proteins. Included in this category are proteins termed p107, p130, and pRb (the retinoblastoma protein). The pocket proteins exert their transcriptional inhibitory activity by directly interacting with the E2F/DP complexes. At the G1/S transition of the cell cycle, where E2F activity is required, the pocket proteins are phosphorylated which causes pRb and E2F to dissociate, leading to activation of the E2F transcription factor.

The physiological relevance of the interactions between E2F and the pocket proteins and between E2F and DP family members is supported by several observations: (i) in a variety of tumors, both copies of the RB gene contain loss of function mutations, and reintroduction of the wild-type RB gene reduces tumorigenicity; (ii) overexpression of E2F-1 in an experimental system can lead to neoplastic transformation; (iii) PRAD1, the gene which encodes cyclin D, a positive regulatory subunit of the pRb kinases, is, as the result of a chromosomal rearrangement, overexpressed in numerous tumors; (iv) disruption of the interaction of E2F with proteins is required for the oncogenic activity of certain DNA tumor viruses. oncogenic proteins such as E1A of adenoviruses, the large T antigen of SV40, and E7 of Human Papilloma Viruses can abrogate pRb-mediated repression of E2F, causing the host cell to enter the cell cycle inappropriately. Compounds which can destabilize the interaction of an oncogenic viral protein with pRb without affecting the interaction of pRb with E2F can be used therapeutically to treat or prevent cancers associated with these viruses.

Previous studies of interactions between regulatory proteins have revealed important paradigms about how proteins interact with each other. For example, studies of protein/protein interactions have led to the identification of several structural motifs (e.g., the helix-loop-helix motif, SH2 and SH3 domains, and the leucine zipper). The primary amino acid sequences of E2Fs, DPs, and the pocket proteins do not resemble any of the known motifs. Thus, a convenient method which permits a detailed study of the protein/protein interactions involved in this novel family of regulatory proteins may reveal new motifs for protein/protein interactions. The E2F-1/DP-1 interaction domain has been mapped to amino acids 120–310 of E2F-1 and amino acids 205–277 of DP-1. In contrast, the E2F-1/pRb interaction domain has been mapped to amino acids 409–427 of E2F-1. Thus, the DP-1 and pRb binding sites on E2F-1 do not overlap. Accordingly, certain mutations may affect the ability of E2F-1 to bind to DP-1 without affecting the ability of E2F-1 to bind to pRb. Similarly, certain compounds may affect the ability of E2F-1 to bind to DP-1 without affecting its ability to bind to pRb.

Counterselectable Markers: While selectable markers have been used to, under certain conditions, promote the growth of only those cells which express the selectable markers, counterselectable marker have been used, under certain conditions, to promote the growth of only those cells which have lost the counterselectable marker. Counterselectable markers when present on plasmids can be used to select for cells that have lost the plasmid, a process called plasmid "shuffling" (see, e.g., Sikorski and Boeke, 1991, Meth. in Enzymol. 194:302). For example, expression of the URA3 gene, which encodes orotidine-5'-phosphate, is lethal in the presence of a medium containing 5-fluoro-orotic acid (5-FOA). Cells expressing URA3 can also be positively selected for by growing them on uracil-free media; thus, depending on the growth conditions, URA3 can be used either for positive or negative conditions. The LYS2 gene, which encodes α-aminoadipate reductase, can also be used for counterselection; yeast cells which express LYS2 will not grow on a medium containing α-aminoadipate as a primary nitrogen source. Similarly, expression of LYS5 on a medium containing α-aminoadipate is lethal. These genes, which are involved in lysine biosynthesis, can be selected in a positive fashion on a lysine-free medium. Another counterselectable reporter gene is the CAN1 gene which encodes an arginine permease. Expression of this gene in the absence of arginine and in the presence of canavanine is lethal. Similarly, expression of the counterselectable gene CYH2 is lethal in the presence of cycloheximide. Expression of a counterselectable reporter gene has been used to identify mutations in the activation domain of estrogen receptor which inhibit its ability to activate transcription (Pierrat et al., 1992, Gene 119:237–245).

SUMMARY OF THE INVENTION

We have discovered that a genetic screening system which employs counterselection provides a convenient method for characterizing molecular interactions in a bidirectional manner. Thus, the invention can be used to determine whether two molecules (e.g., proteins, RNA molecules, or DNA molecules) interact. In addition, by using counterselection and by measuring the level of expression of a reporter gene, the invention can be used to determine how well two molecules interact. Thus, each of the methods of the invention employs counterselection, and most embodiments of the invention employ at least two hybrid proteins; thus, the methods have been termed reverse two-hybrid systems. The invention provides methods for (i) determining whether a first test protein is capable of interacting with a second test protein, where the proteins can be expressed from two separate nucleic acid libraries (i.e., bidirectional combinatorial libraries); in principle, this approach allows the identification all proten/protein interactions in a given genome; (ii) determining whether a compound can disrupt a protein/protein interaction; (iii) determining whether a first test protein is capable of interacting with a second test protein and incapable of interacting with a third test protein; (iv) determining whether a test protein is capable of interacting with a test RNA molecule; (iv) determining whether a first test RNA molecule is capable of interacting with a second test RNA molecule; (vi) identifying mutations which affect protein/protein, interactions (two-step selection); (vii) identifying a conditional allele of a protein which affects protein/protein interactions; (viii) identifying compensatory mutations which affect protein/protein interactions (bivalent genetics), and (ix) identifying protein/DNA interactions. The invention also features yeast strains and several genetic constructs which are useful for identifying molecular interactions with the disclosed methods.

The invention features, in one aspect, a method for determining whether a first test protein is capable of interacting with a second test protein. The method involves the following steps:

(a) providing a first population of mating competent cells, in which a plurality of the cells of the first population contain: (i) a first selectable/counterselectable reporter gene operably linked to a first DNA-binding-protein recognition site; (ii) a first fusion gene which expresses a first hybrid protein; the first hybrid protein includes the first test protein covalently bonded to a DNA-binding moiety which is capable of specifically binding to the DNA-binding-protein recognition site;

(b) providing a second population of mating competent cells, in which a plurality of the cells of the second population contain: (i) a second selectable/counterselectable reporter gene operably linked to a second DNA-binding-protein recognition site; and (ii) a second fusion gene which expresses a second hybrid protein; the second hybrid protein includes the second test protein covalently bonded to a gene activating moiety;

(c) maintaining the first and the second populations of mating competent cells, independently, under conditions such that expression of the counterselectable reporter genes inhibits the growth of said cells;

(d) mixing the first and the second populations of mating competent cells under conditions conducive to formation of mated cells; and (e) detecting expression of a reporter gene as a measure of the ability of the first test protein to interact with the second test protein, where the reporter gene is the first or the second reporter gene or another reporter gene included in the first or the second mating competent cells or the mated cells, and is operably linked to either the first of the second DNA-binding-protein recognition sites.

In this aspect of the invention, the peptide sequences of the first and second test proteins can be intentionally designed or randomly generated. If desired, the sequence of one of the two test proteins can be intentionally designed while the other is randomly generated. In yet another embodiment of the invention, one part of the protein is intentionally designed, and a second part is randomly generated. Preferably, the selectable/counterselectable reporter genes used in this aspect of the invention selected from the group including URA3, LYS2, and GAL1. If desired, the first and second counterselectable genes can be identical (e.g., both counterselectable genes can be URA3 genes), or two different counterselectable genes can be used (e.g., URA3 and LYS2).

In a second aspect, the invention features a method for determining whether a test compound is capable of disrupting or preventing binding between a first test protein and a second test protein. The method involves the following steps:

(a) providing a cell containing:
    (i) a counterselectable reporter gene operably linked to a DNA-binding-protein recognition site;
    (ii) a first fusion gene expressing a first hybrid protein which includes the first test protein covalently bonded to a DNA-binding moiety which is capable of specifically binding to the DNA-binding-protein recognition site; and
    (iii) a second fusion gene expressing a second hybrid protein which includes the second test protein covalently bonded to a gene activating moiety; the second test protein being one which binds the first test protein in the absence of the test compound;

(b) contacting the cell with the test compound under conditions such that expression of counterselectable reporter gene inhibits cell growth;

(c) detecting inhibition of expression of the counterselectable reporter gene as a measure of the ability of the compound to disrupt or prevent binding between the first and the second test proteins.

In this aspect of the invention, the first and second test proteins should be known to interact with each other in the absence of the test compound. Suitable pairs of test proteins include, for example, cFos and cJun, cJun and cJun, and E2F1 and pRb. The test compound can be any molecule, such as a small, organic molecule or a protein (e.g., a protein which is encoded by a nucleic acid of a nucleic acid library, or a protein of a randomly generated peptide sequence). Examples of preferred proteins to be used as test compounds include E1A of adenovirus, large T antigen of SV40, and E7 of a Human Papilloma Virus. Inhibition of expression of the counterselectable reporter gene can be detected by assaying for growth of the cell in the presence of a compound that normally is toxic to the cell when the counter selectable reporter gene is expressed. In this embodiment of the invention, suitable counterselectable reporter genes include URA3, LYS2, GAL1, CYH2, and CAN1.

The invention also features a method for determining whether a first test protein is capable of interacting with a second test protein and incapable of interacting with a third test protein. The method involves:

(a) providing a cell which contains:
    (i) a first fusion gene which expresses a first hybrid protein; the first hybrid protein includes the first test protein covalently bonded to a gene activating moiety;
    (ii) a reporter gene which is operably linked to a first DNA-binding-protein recognition site;
    (iii) a second fusion gene which expresses a second hybrid protein, the second hybrid protein includes the second test protein covalently bonded to a DNA-binding moiety which is capable of specifically binding to the first DNA-binding-protein recognition site and which is incapable of specifically binding to a second DNA-binding-protein recognition site;
    (iv) a counterselectable reporter gene operably linked to the second DNA-binding protein recognition site; and
    (v) a third fusion gene which expresses a third hybrid protein; the third hybrid protein includes the third test protein covalently bonded to a second DNA-binding-moiety which is capable of specifically binding to the second DNA-binding-protein recognition site and incapable of binding to the first DNA-binding-protein recognition site;

(b) maintaining the cell under conditions such that expression of the reporter gene is detectable and does not inhibit the growth of the cell, and expression of the counterselectable reporter gene inhibits the growth of the cell; and (c) detecting growth of the cell and expression of the selectable reporter gene as a measure of the ability of the first test protein to interact with the second test protein, and as a measure of the inability of the first test protein to interact with the third test protein.

If desired, the ability of the first test protein to interact with the second test protein and not with the third test protein can be measured in the presence of a test compound, such as a polypeptide, a nucleic acid, or a small organic molecule. Where a polypeptide acts as the test compound, the polypeptide can be of a randomly generated peptide sequence, of an intentionally designed peptide sequence, or encoded by a nucleic acid contained within a nucleic acid library. In addition, any of the test proteins can comprise a randomly generated peptide sequence or be mutagenized versions of preferred proteins. Useful counterselectable reporter genes include URA3, LYS2, GAL1, CYH2, and CAN1. Preferred reporter genes include LEU2, TRP1, HIS3, and LacZ.

The invention further features a method for determining whether a test RNA molecule is capable of interacting with a test protein. The method involves:

(a) providing a first population of mating competent cells in which a plurality of the cells of the population contain:
  (i) a first selectable/counterselectable reporter gene operably linked to a first DNA-binding-protein recognition site;
  (ii) a first fusion gene which expresses a first hybrid RNA molecule in which the test RNA molecule is covalently bonded to a non-random RNA molecule; and
  (iii) a second fusion gene which expresses a first hybrid protein having a DNA-binding moiety which is capable of specifically binding to the first DNA-binding-protein recognition site, the DNA-binding moiety being covalently bonded to an RNA-binding moiety, and the RNA-binding moiety being capable of specifically binding to the non-random RNA molecule;

(b) providing a second population of mating competent cells, in which a plurality of the cells of the population contain:
  (i) a second selectable/counterselectable reporter gene operably linked to a second DNA-binding-protein recognition site; and
  (ii) a third fusion gene which expresses the test protein covalently bonded to a gene activating moiety; and (c) maintaining the first and the second populations of mating competent cells, independently, under conditions such that expression of the selectable/counterselectable reporter genes inhibits growth of the cells of the populations;

(d) mixing the first and the second populations of mating competent cells under conditions conducive to formation of mated cells; and (e) detecting expression of a selectable/counterselectable reporter gene as a measure of the ability of the test RNA molecule to interact with the test protein.

If desired, the test RNA molecule and/or test protein can include a randomly-generated nucleotide or amino acid sequence; alternatively, the test RNA molecule and/or test protein can be intentionally designed. Optionally, the ability of the test RNA molecule and test protein to interact can be measured in the presence of a test compound (e.g., a dissociator or stabilizer of the interaction), such as a protein (e.g., an intentionally designed protein or a randomly generated protein such as a protein encoded by a nucleic acid contained within a nucleic acid library). Preferred selectable/counterselectable reporter genes include URA3, LYS2, and GAL1.

An additional feature of the invention is a method for determining whether a first test RNA molecule is capable of interacting with a second test RNA molecule. The method involves:

(a) providing a first population of mating competent cells in which a plurality of the cells of the population contain:
  (i) a first selectable/counterselectable reporter gene operably linked to a first DNA-binding-protein recognition site;
  (ii) a first fusion gene which expresses a first hybrid RNA molecule; the first hybrid RNA molecule includes the first test RNA molecule covalently bonded to a first non-random RNA molecule; and
  (iii) a second fusion gene which expresses a first hybrid protein; the first hybrid protein includes a DNA-binding moiety which is capable of specifically binding to the first DNA-binding-protein recognition site, and the DNA-binding moiety is covalently bonded to a first RNA-binding moiety which is capable of specifically binding to the first non-random RNA molecule;

(b) providing a second population of mating competent cells in which a plurality of the cells of the population contain:
  (i) a second selectable/counterselectable reporter gene operably linked to a second DNA-bindingprotein recognition site;
  (ii) a third fusion gene which expresses a second hybrid RNA molecule; the second hybrid RNA molecule includes the second test RNA molecule covalently bonded to a second non-random RNA molecule; and
  (iii) a fourth fusion gene which expresses a gene-activating moiety covalently bonded to a second RNA-binding moiety which is capable of specifically binding to the second non-random RNA molecule;

(c) maintaining the first and the second populations of mating competent cells, independently, under conditions such that expression of the selectable/counterselectable reporter genes inhibits growth of the cells;

(d) mixing the first and the second populations of mating competent cells under conditions conducive to formation of mated cells; and (e) detecting expression of a counterselectable reporter gene as a measure of the ability of the first test RNA molecule to interact with the second test RNA molecule.

If desired, the first and/or second test RNA molecule can include a randomly generated RNA sequence. The amino acid or RNA sequence of a protein or RNA molecule used as a test compound can be intentionally designed or randomly generated (e.g., be encoded by a nucleic acid contained within a nucleic acid library). Preferred selectable/counterselectable reporter genes in this aspect of the invention include URA3, LYS2, and GAL1. Preferably, the first RNA-binding moiety does not bind to the second non-random RNA molecule, and the second RNA-binding moiety does not bind to the first non-random RNA molecule.

In another aspect, the invention features a method for determining whether a test DNA molecule is capable of interacting with a test protein. The method involves:

(a) providing a cell which contains (i) a counterselectable reporter gene operably linked to the test DNA molecule; and (ii) a fusion gene which expresses the test protein covalently bonded to a gene activating moiety; and (b) detecting expression of said counterselectable reporter gene as a measure of the ability of said test DNA molecule to interact with said test protein.

If desired, the DNA can be randomly generated and/or the protein include a randomly generated peptide sequence.

In yet another aspect, the invention features a method for identifying a mutation in a reference protein which affects the ability of the reference protein to interact with a test protein. The method involves:

(a) providing a cell which contains:
  (i) a counterselectable reporter gene operably linked to a DNA-binding-protein recognition site;
  (ii) a selectable reporter gene operably linked to a DNA-binding-protein recognition site;
  (iii) a first fusion gene expressing a first hybrid protein, where the first hybrid protein includes the first test protein; and
  (iv) a second fusion gene expressing a second hybrid protein, the second hybrid protein includes a candidate mutated reference protein, and the second test protein is encoded within a nucleic acid library of mutant alleles of the gene encoding the reference protein; and one of the first and the second hybrid proteins also includes a DNA-binding moiety which is capable of specifically binding to the DNA-binding-protein recognition site, and the other of the first and the second hybrid proteins also includes a gene activating moiety;

(b) maintaining the cell under conditions such that expression of the counterselectable reporter gene at a level equal to or greater than the level of expression obtained with the reference protein inhibits growth of the cell, and such that expression of the counterselectable reporter gene at a level less than the level of expression obtained with the reference protein does not inhibit growth of the cell;

(c) in a separate step, maintaining the cell under conditions such that expression of the counterselectable reporter gene does not inhibit growth of the cell, and detecting expression of the selectable reporter gene as a measure of the ability of the first test protein to interact with the candidate mutated reference protein.

If desired, the method can include comparing the sequence of the candidate mutated protein with the sequence of the reference protein as an indicator of a mutation in the reference protein which affects the ability of the reference protein to interact with the first test protein. If desired, the second fusion gene can encode a functional C-term tag, and, as is described herein, the presence of the functional C-term tag, indicating the presence of the C-terminus of the candidate mutated protein, can be measured by detecting expression of the selectable reporter gene or with other methods (e.g., detection of GFP with UV light).

In another aspect, the invention features a method for identifying a conditional mutant of a reference protein which has a decreased ability to interact with a second protein under a first set of conditions and which is capable of interacting with the second protein under a second set of conditions. The method involves:

(a) providing a cell which contains:
  (i) a counterselectable reporter gene operably linked to a DNA-binding-protein recognition site;
  (ii) a selectable reporter gene operably linked to a DNA-binding-protein recognition site;
  (iii) a first fusion gene expressing a first hybrid protein, where the first hybrid protein includes the candidate mutated reference protein, and the candidate mutated reference protein is encoded within a nucleic acid library of mutant alleles of the gene encoding the reference protein; and
  (iv) a second fusion gene expressing a second hybrid protein, where the second hybrid protein includes a second protein, and one of the first or second hybrid proteins also includes a DNA-binding moiety which is capable of specifically binding to the DNA-binding-protein recognition site, and the other of the first or second hybrid proteins also includes a gene activating moiety;

(b) maintaining the cell under conditions in which expression of the counterselectable reporter gene at a level equal to or greater than the level of expression obtained with the reference protein inhibits growth of the cell, and such that expression of the counterselectable reporter gene at a level less than the level of expression obtained with the reference protein does not inhibit growth of the cell;

(c) in a separate step, maintaining the cell under conditions such that expression of the counterselectable reporter gene does not inhibit growth of the cell, and detecting expression of the selectable reporter gene as a measure of the ability of the candidate mutant protein to interact with the second protein; and (d) in a separate step, maintainng the cells under conditions identical to those in step (c) except for one parameter, and detecting expression of the selectable reporter gene as a measure of the ability of the candidate mutant protein to interact with the second protein, (expression of the selectable reporter gene under step (c) conditions but not under step (d) conditions is indicative of the conditional mutant).

If desired, the method can also include comparing the sequence of the candidate mutant protein with the sequence of the reference protein as a means for identifying a mutant of the reference protein which has a decreased ability to interact with the second protein under a first set of conditions and which is capable of interacting with the second protein under a second set of conditions.

The conditions under which the cell is maintained in step (b) and the conditions under which the cell is maintained in step (c) can differ in any way desired by the practitioner. For example, the first and second growth conditions can differ in temperature and/or by the presence of a drug (e.g., formamide or deuterium).

The invention also features a method for identifying compensatory mutations in a first and a second reference protein which allow a first and a second mutant reference protein to interact with each other but not with the second and the first reference proteins, respectively. The method involves:

(a) providing a first population of mating competent cells in which a plurality of the cells of the population contain:

(i) a first counterselectable reporter gene operably linked to a DNA-binding-protein recognition site;

(ii) a first selectable reporter gene operably linked to a DNA-binding-protein recognition site;

(iii) a first fusion gene which expresses a first hybrid protein, where the first hybrid protein includes a first candidate mutant reference protein covalently bonded to a gene activating moiety, and where the first candidate mutant protein is encoded within a nucleic acid library of mutant alleles of the first reference protein; and (iv) a plasmid containing a first counterselectable marker, and a second fusion gene which expresses a second hybrid protein, where the second hybrid protein includes the second reference protein covalently bonded to a DNA-binding moiety;

(b) providing a second population of mating competent cells in which a plurality of the cells of the population contain:

(i) a second counterselectable reporter gene operably linked to a DNA-binding-protein recognition site;

(ii) a second selectable reporter gene operably linked to a DNA-binding-protein recognition site;

(iii) a third fusion gene which expresses a third hybrid protein, where the third hybrid protein includes the second candidate mutant reference protein covalently bonded to a DNA-binding moiety, and where the second candidate mutant protein is encoded within a nucleic acid library of mutant alleles of the second reference protein; and (iv) a plasmid containing a second counterselectable marker and a fourth fusion gene which expresses a fourth hybrid protein, where the hybrid protein includes the first reference protein covalently bonded to a gene activating moiety;

(c) maintaining the first and the second populations of mating competent cells, independently, under conditions such that expression of the counterselectable reporter genes at a level equal to or greater than the level of expression obtained with the first and second reference proteins inhibits growth of the cells;

(d) maintaining the first and the second populations of mating competent cells under conditions such that expression of the counterselectable marker inhibits growth of the cells;

(e) maintaining the first and the second populations of mating competent cells under conditions conducive to formation of mated cells;

(f) detecting expression of the selectable reporter genes as a measure of the ability of the first and the second candidate proteins to interact with each other and not with the second and the first reference proteins.

If desired, the method can also include comparing the sequences of the first and the second candidate mutant proteins which interact with each other with the sequences of the first and the second reference proteins as a means for identifying compensatory mutations in the first and the second reference proteins.

The invention further features several genetic constructs which are useful in practicing various aspects of the invention. In one aspect, the genetic construct includes: (i) a yeast origin of replication; (ii) a selectable marker; (iii) a yeast promoter; (iv) a nuclear localization coding signal sequence; and (v) a bacterial origin of replication. A preferred nuclear localization coding signal sequence is the nuclear localization coding signal sequence of SV40 large T antigen. A preferred promoter is the ADH1 promoter, and a preferred genetic construct is the plasmid p2.5.

In another aspect, the genetic construct includes: (i) a yeast origin of replication; (ii) a selectable marker; (iii) a promoter; (iv) a bacterial origin of replication; (v) a counterselectable marker; and (vi) a sequence which expresses a DNA-binding moiety. Preferably, the genetic construct is p97.CYH2.

In still another aspect, the genetic construct includes: (i) a yeast origin of replication; (ii) a selectable marker; (iii) a promoter; (iv) a bacterial origin of replication; (v) a counterselectable marker; and (vi) a sequence which expresses a gene activating moiety. Preferably, the genetic construct is pMV257.

More generally, the invention features any genetic construct (e.g., a plasmid or a chromosome) having a counterselectable reporter gene operably-linked to a promoter which contains an upstream repressing sequence and a DNA-binding-protein recognition site for a DNA-binding moiety which can mediate transcription of the counterselectable reporter gene (e.g., an intact or a reconstituted transcription factor). Included in the preferred promoters is a SPO13 promoter, and a preferred counterselectable reporter gene is the URA3 gene. A preferred DNA-binding-protein recognition site is the binding site for Gal4. Thus, a preferred genetic construct is SPAL:URA3.

In addition, the invention features a yeast cell having integrated into its genome a counterselectable reporter gene which is operably linked to a promoter which includes (i) an upstream repressing sequence, and (ii) a DNA-binding-protein recognition site, wherein the yeast cell lacks (i) a naturally-occurring protein which is substantially identical to the protein encoded by the counterselectable reporter gene, and (ii) at least one naturally-occurring protein which, when it is expressed, confers a growth advantage on a cell containing it. Such a yeast cell can contain a SPO13 promoter which includes a DNA-binding-protein recognition site for a protein selected from the group which includes GAL4, LexA, and Ace1. Preferred yeast cells include MaV103, MaV203, and MaV99.

In preferred embodiments of each of the aforementioned aspects of the invention, the cells of the populations of cells are yeast cells; preferably, the yeast is *Saccharomyces cerevisiae*. If desired, the ability of two or more molecules to interact can be measured in the presence of a test compound in a method of identifying compounds which dissociate or stabilize the interaction of two molecules of interest. The test compound can be expressed within the cell by employing conventional methods for gene expression, or the test compound can simply be added to the growth medium. Yeast strains employed in the invention can be chemically treated (e.g., with polymixin B nonapeptide) to increase the uptake of compounds (see, e.g., Boguslawski et al., Mol. Gen. Genet. 199:401–405 and Antimicrob. Agents and Therapies 29:330–332). Where the test compound is added to the growth medium, yeast mutants which have relatively high uptake levels of extraneous compounds, such as the erg6, ise1, ISE2, and srb1 mutants of *S. cerevisiae*, are particularly useful. Where two populations of mating competent yeast cells are used to produce mated cells, the two populations must include mating competent cells of compatible mating types (e.g., MATa and MATα).

If desired, the methods of the invention can be coupled with methods for mutagenizing proteins or RNA molecules. In order to identify amino acid residues or nucleotides-responsible for the interaction of proteins and/or RNA molecules. For example, mutations in one or both of two proteins which prevent two proteins from interacting indicate that amino acids at those positions contribute to the ability of the wild-type proteins to interact. Similarly, compensatory mutations in two interacting proteins define critical amino acids which contribute to the ability of the corresponding wild-type proteins to interact. The invention also provides methods for identifying conditional alleles that affect protein/protein, protein/RNA, protein/DNA interactions, or RNA/RNA interactions. Once identified, a conditional allele provides a detectable phenotype that can be used to characterize the function of a protein or RNA molecule. Such alleles can be identified by mutating one of the interacting molecules and identifying those mutants which can interact with its wild-type partner under certain (i.e., permissive), but not other (i.e., restrictive), conditions.

Preferably, each of the reporter genes is operably linked to a promoter which carries a repressing sequence which prevents transcription in the absence of a gene activating moiety. Thus, the reporter gene should be positioned such that its expression is highly responsive to the presence or absence of a transcription factor. For example, it is preferred that where a URA3 allele is used, the allele confers a Ura⁻ Foa$^r$ phenotype in the absence of a transcription factor, and it confers a Ura⁺ Foa$^s$ phenotype in the presence of a transcription factor. Certain promoters, such as the SPO13 promoter, naturally contain an upstream repressing sequence. Other promoters can be engineered with conventional cloning methods to contain such sequences. Where a counterselectable reporter gene is used, expression of the gene can be detected by detecting inhibition of cell growth.

Where more than one reporter gene is employed, the reporter genes can be connected to promoters which are identical to each other only at their DNA-binding-protein recognition sites, if desired. Preferably, the reporter gene is one which allows for titratable selection; thus, cell growth can be measured over a range of conditions (e.g., 5-FOA concentrations).

A variety of DNA-binding moieties and gene activating moieties are suitable for use in the various aspects of the invention. Generally, the DNA-binding domain or gene activating domain of any transcription factor can be used. If desired, the gene activating domain of VP16 can be used. The DNA-binding-protein recognition site and the gene activating and DNA-binding moieties all can correspond to identical transcription factors, or they can correspond to different transcription factors. Useful binding sites include those for the yeast protein GAL4, the bacterial protein LexA, the yeast metal-binding factor Ace1. These binding sites can readily be used with a repressed promoter (e.g., a SPO13 promoter can be used as the basis for SPAL, SPEX and SPACE promoters, respectively, for a SPO13 promoter combined with GAL, LEX, and ACE1 DNA binding sites). Other useful transcription factors include the GCN4 protein of *S. cerevisiae* (see, e.g., Hope and Struhl, 1986, Cell 46:885–894) and the ADR1 protein of *S. cerevisiae* (see, e.g., Kumar et al., 1987, Cell 51:941–951). The DNA-binding-protein recognition site should include at least one binding site for the DB of the transcription factor that is used. While the number of DNA-binding-protein recognition sites that can be used is unlimited, the number of binding sites is preferably between 1 and 100, more preferably 1 and 20; still more preferably, the number of binding sites is between 1 and 16. The number of binding sites can be adjusted to account for factors such as the desired sensitivity of the assay.

If desired, the allele for the reporter gene (e.g., SPALX:URA3) can be integrated into the genome of a haploid or diploid cell. If desired, a combination of alleles can be used; for example, SPALX:URA3 can be chromosomally located and SPEX:URA3 can be located on a plasmid; SPALX:URA3 can be expressed from a plasmid and SPACEX:URA3 can be located on a chromosome.

By "dissociator compound" is meant any molecule which disrupts or prevents binding of two molecules. Examples of dissociator compounds (also referred to herein as "dissociators") are polypeptides, nucleic acids, and small, organic molecules (i.e., molecules having a molecular weight of less than 1 kD).

By "reporter gene" is meant a gene whose expression can be assayed as a measure of the ability of two test molecules to interact (i.e., as a measure of protein/protein, protein/RNA, RNA/RNA, or protein/DNA interactions). A useful reporter gene has in its promoter a DNA-binding-protein recognition site to which a reconstituted transcription factor or DNA-binding protein of interest binds. Such genes include, without limitation, lacZ, amino acid biosynthetic genes (e.g., the yeast LEU2, HIS3, LYS2, or TRP1), URA3 genes, nucleic acid biosynthetic genes, the bacterial chloramphenicol transacetylase (cat) gene, and the bacterial gus gene. Also included are those genes which encode fluorescent markers, such as the Green Fluorescent Protein gene. Certain reporter genes are considered to be "selectable," "counterselectable," or "selectable/counterselectable" reporter genes, as is described below.

By "test" protein, RNA molecule, or DNA molecule is meant a molecule whose function (i.e., ability to interact with a second molecule) is being characterized with the methods of the invention.

By "DNA-binding" protein is meant any of numerous proteins which can specifically interact with a nucleic acid. For example, a DNA-binding protein used in the invention can be the portion of a transcription factor which specifically interacts with a nucleic acid sequence in the promoter of a gene. Alternatively, the DNA-binding protein can be any protein which specifically interacts with a sequence which is naturally-occurring or artificially inserted into the promoter of a reporter gene. Where protein/DNA interactions are characterized, the DNA-binding protein can be covalently bonded to a gene-activating moiety such that binding of the DNA-binding protein to a site located within the promoter of a chosen reporter gene activates transcription of the reporter gene.

By "selectable" marker is meant a gene which, when it is expressed, confers a growth advantage on a cell containing it. Examples of selectable markers include, without limitation, LEU2, TRP1, and HIS3. Certain selectable markers described herein can be used to promote the growth of cells containing a plasmid containing a selectable marker. A promoter which is operably linked to a selectable marker located on a plasmid can be the naturally-occurring promoter for the marker, or the marker can be engineered to be operably linked to a promoter other than the one to which it is naturally operably linked. Generally, a promoter which is operably linked to a selectable marker located on a plasmid (e.g., a plasmid used to express an interacting molecule or dissociator) used in the invention does not contain a DNA-binding-protein recognition site(s) which is functionally identical to a DNA-binding-protein recognition site contained within the promoter of the reporter gene which is used to measure the molecular interaction of interest. In other words, the DNA-binding-protein which mediates transcription of the reporter gene should not also mediate transcription of the selectable marker, and the DNA-binding-protein which mediates transcription of the selectable marker should not also mediate transcription of the reporter gene.

By "screenable" reporter gene is meant a gene whose expression can be detected in a cell by a means other by conferring a selective growth advantage on a cell. An example of a screenable reporter gene is the lacZ gene. If desired, a screenable reporter gene can be integrated into the genome of a yeast cell. It is preferred, though not essential, that the promoter of the screenable reporter gene be distinct from the promoters of any other reporter genes used in the cell. A screenable reporter gene can be used in the invention to measure the ability of two molecules to interact and reconstitute a transcription factor. Thus, the promoter which is operably linked to a screenable reporter gene should contain a DNA-binding-protein-recognition site(s) to which a reconstituted transcription factor, or to which a DNA-binding protein fused to a gene-activating moiety, can bind.

By "counterselectable" marker is meant a gene which, when it is expressed, prevents the growth of a cell containing it. Examples of counterselectable reporter genes include URA3, LYS2, GALZ, CYH2, and CAN1. These markers can be used to select for plasmid elimination.

By "selectable" reporter gene is meant a reporter gene which, when it is expressed under a certain set of conditions, confers a growth advantage on cells containing it.

By "counterselectable" reporter gene is meant a reporter gene which, when it is expressed under a certain set of conditions, prevents the growth of a cell containing it. Examples of counterselectable reporter genes include URA3, LYS2, GAL1, CYH2, and CAN1.

By "selectable/counterselectable" reporter gene is meant a reporter gene which, when it is expressed under a certain set of conditions, is lethal to a cell containing it, and when it is expressed a different set of conditions, confers a selective growth advantage on cells containing it. Thus, a single gene can be used as both a selectable reporter gene and a counterselectable reporter gene. Examples of selectable/counterselectable reporter genes include URA3, LYS2, and GAL1. In each aspect of the invention where a selectable/counterselectable reporter gene is employed, a combination of a selectable reporter gene and a counterselectable reporter gene can be used in lieu of a single selectable/counterselectable reporter gene. For example, in the first aspect of the invention, each mating competent cell can be provided with (i) a selectable reporter gene, and (ii) a counterselectable reporter gene. Where two such genes substitute for a single selectable/counterselectable gene, it is preferred that the reporter genes be operably linked to identical promoters. In particular, it is preferred that the reporter genes be operably linked to promoters that have identical DNA-binding-protein recognition site.

By "DNA-binding-protein recognition" site is meant a segment of DNA that is necessary and sufficient to specifically interact with a given polypeptide (i.e., the DNA-binding-protein).

By "covalently bonded" is meant that two molecules (e.g., RNA molecules or proteins) are joined by covalent bonds, directly or indirectly. For example, the "covalently bonded" proteins or protein moieties may be immediately contiguous, or they may be separated by stretches of one or more amino acids within the same hybrid protein.

By "protein" is meant a sequence of amino acids, constituting all or a part of a naturally-occurring polypeptide or peptide, or constituting a non-naturally-occurring polypeptide or peptide.

By "DNA-binding moiety" is meant a stretch of amino acids which is capable of directing specific polypeptide binding to a particular DNA sequence (i.e., a DNA-binding-protein recognition site).

By "RNA-binding moiety" is meant a stretch of amino acids which is capable of directing specific polypeptide binding to a particular RNA sequence (i.e., an RNA-binding-protein recognition site).

By "hybrid" protein, RNA molecule, or DNA molecule is meant a chimera of at least two covalently bonded polypeptides, RNA molecules, or DNA molecules.

By "gene activating moiety" is meant a stretch of amino acids which is capable of inducing the expression of a gene to whose control region (i.e., promoter) it is bound.

By "operably linked" is meant that a gene and a regulatory sequence(s) (e.g., a promoter) are connected in such a way as to permit gene expression when the appropriate molecules (e.g., transcriptional activator proteins or proteins which include transcriptional activation domains) are bound to the regulatory sequence(s).

By "randomly generated" sequence is meant a sequence having no predetermined sequence; this is contrasted with "intentionally designed" sequences which have a DNA, RNA, or protein sequence or motif which is determined prior to their synthesis. Randomly generated sequences can be derived from a nucleic acid library.

By "mutated" is meant altered in sequence, either by site-directed or random mutagenesis. Mutated sequences include those sequences which have point mutations, insertions, deletions, or rearrangements.

By "promoter" is meant minimal sequence sufficient to direct transcription; such elements can be located in the 5' or 3' regions of the native gene.

By "repressing" sequence is meant a DNA sequence which, under certain conditions, inhibits expression of a gene to which it is connected.

By nucleic acid "library" is meant a set of 5 or more DNA molecules. Such a library can have hundreds, thousands, or even millions of different DNA molecules.

By "bidirectional combinatorial library" is meant a very large set of pairs of interacting hybrid molecules generated from two separate, parental expression libraries. Typically, the size of the set is approximately the product of the complexities of each parental library.

By "compensatory" mutations is meant mutations in a pair of interacting molecules (e.g., proteins) which allow the molecules to interact with each other but not with wild-type molecules.

By "mass mating" is meant the mixing of suspensions of mating competent yeast cells of complementary mating types so as to generate a very large number of mated cells. Typically, $10^{10}$ or even $10^{12}$ mated cells are generated. Preferably, the suspensions of cells are mixed at a 1:1 ratio (number of cells:number of cells).

By "functional C-term tag" is meant a stretch of amino acids located at the C-terminus of a test protein, the presence of which can be assayed to confirm that the carboxyl terminus of the test protein is intact, indicating that a full-length protein is expressed at detectable levels. For example, the functional C-term tag can be a sequence (e.g., the pocket binding domain of E2F1) which can interact with a second protein (e.g., pRb, p107, or p130). If desired, the functional C-term tag can be a sequence which can be detected without binding a second protein. For example, GFP (green fluorescent protein) can serve as a functional C-term tag, and it can be detected with UV light.

The present invention offers several features and advantages. For example, the invention allows one to screen two libraries of cDNA clones encoding peptides or RNA molecules simultaneously. Using the "mass mating" methods, the reaction testing the functional relationship of the various molecules is performed only once, and under identical conditions for all combinations of molecules in a given system. In addition, it is not necessary to have previously identified any of the molecules which interact. The present invention facilitates generation and screening of as many as $1 \times 10^{13}$ interactions. Thus, the invention facilitates screening of a large number of combinations of molecules, increasing the probability of detecting relatively rare association or dissociation events. The invention can be used, on a large scale, to generate protein/protein linkage maps of most or all interactions that occur with two libraries of interest. Yeast cells containing each of the possible pairs of interacting molecules can be organized on plates in a method of cataloging the molecular interactions. For example, DNA encoding a protein of interest can be used as a probe in a DNA hybridization against DNA extracted from yeast colonies organized on a solid support (e.g., a nitrocellulose filter). By identifying a yeast colony to which the DNA of interest hybridizes, one immediately has identified a yeast strain containing a molecule which interacts with the protein of interest encoded by the DNA of interest. The gene encoding the few interacting molecule can then be cloned from a yeast cell derived from a hybridization positive colony.

The invention can also be used with great sensitivity to detect relatively rare association events. Accordingly, the invention addresses one of the most significant challenges in the construction of combinatorial libraries: identification of the few pairs of interacting molecules from a large population of potentially interacting molecules.

The invention also permits the identification of molecules which dissociate or prevent undesired interactions but which do not dissociate or prevent desired interactions. For example, the invention facilitates the identification of compounds which dissociate or prevent binding of viral proteins to molecules in a host cell but which do not affect binding of the host cell molecule to preferred molecules. In addition, the invention allows these dissociator compounds to be identified on a single medium (i.e., a single plate), making the screening of therapeutic compounds a rapid and convenient process. Compounds which stabilize molecular interactions can also be identified rapidly and conveniently by assaying for increased expression of a reporter gene in the presence of the compound.

The invention can also be used to identify the targets of a drug of interest (e.g., a dissociator or a stabilizer) for which the relevant molecular interaction is unknown. This method employs a collection of yeast cells, where each cell of the collection contains a pair of interacting molecules from a bidirectional combinatorial library. Each cell in the collection is exposed to the drug of interest, and colonies which express the reporter gene at an altered level (e.g., higher or lower) in the presence of the drug represent cells containing hybrid proteins which are targets of the drug of interest. The hybrid proteins encoded within these cells can be identified with conventional methods.

Because low-copy plasmids can be used in the invention, the proteins and RNA molecules of interest can be expressed at physiologically relevant levels. Expression of the molecules of interest from low-copy plasmids should allow a practitioner to detect subtle differences between various pairs of interacting molecules. When genes are overexpressed from high-copy plasmids, differences between pairs of proteins tend to be more difficult to detect as dissimilar pairs of interacting molecules can sometimes cause apparently similar levels of expression of the reporter gene. Reproducibility in the levels of expression of hybrid proteins in different yeast cells can be optimized with the use of low-copy plasmids.

Certain embodiments of the invention reduce the occurrence of four types of false positives (relative to their incidence obtained with other systems). Interactions classified as false positives include interactions between:

(i) proteins which obviously could not interact under physiological conditions because they are not expressed (a) in the same cell-type, (b) in the same cellular compartment, or (c) at the same stage of development;

(ii) proteins which are not biologically relevant and which may result from expression of the incorrect open reading frame; or (iii) proteins which mediate transcription of the reporter gene by themselves, without requiring a specific interaction partner. The appearance of these false positives is highly promoter-dependent (Bartel et al., 1993, Biofeedback 14:920–924). In addition, it has been suggested that 0.1% of random sequences from *E. coli* can activate transcription (i.e., function as an AD) when fused to a DB in a eukaryotic cell (Ma and Ptashne, 1987, Cell 51:113–119).

By maintaining the level of expression of the hybrid proteins at physiologically relevant levels, the invention inhibits the recovery of the first two classes of false positives. If desired, the chances of obtaining false positives can also be decreased by using a "triple selection method" in practicing the invention. For triple selection, three reporter genes are operably linked to promoters which have different sequences, with the exception of the DNA-binding-protein recognition sequence (FIG. 1). By employing three reporter genes which are operably linked to three different promoters, the likelihood of recovering the third class of false positives is diminished.

Where the invention is used to detect binding of a monoclonal antibody to an antigen, the invention offers the following features. Like the immune system, the invention is combinatorial in nature, and thus the mass mating method used in the invention facilitates analysis of large numbers of combinations of interacting molecules. In addition, the somatic refinement capability of the immune system can be reproduced synthetically with the use of the invention and the PCR mutagenesis method and titratable selection method described herein.

The invention also provides a convenient method for isolating mutant alleles of a protein or RNA molecule. While conventional methods of isolating mutant alleles are based on a previous implication of a particular region of a molecule (e.g., a domain which is conserved among related molecules), the invention permits large numbers of mutant alleles to be generated and screened in a manner without prior knowledge of the molecule and without bias in the mutagenesis method.

The invention can be used as a tool for providing information regarding the structure and regulation of molecular (e.g., protein/protein) interactions. Particularly interesting molecular interactions that can be examined with the invention include protein/protein interactions between a virus and components of a host cell. Dissociator compounds which can disrupt or prevent these interactions can be used therapeutically to decrease viral pathogenicity.

DETAILED DESCRIPTION

The drawings will first be briefly described.

Figure 3:
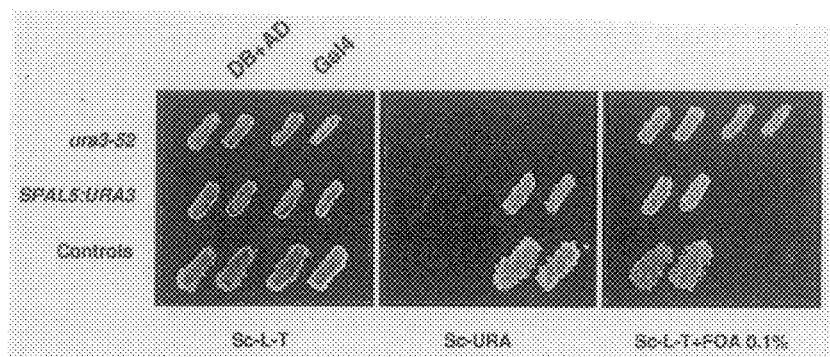

FIG. 3 is a photograph of yeast cells which demonstrates that expression of a SPAL5:URA3 allele can be induced in cells and confer a Foa$^s$ phenotype on cells. Control strains are wild-type URA3 (two patches on right side of each panel) and ura3-52 mutant strains (two patches on left side of each panel). The cells were grown on synthetic complete medium lacking leucine and tryptophan (Sc-L-T), synthetic complete medium lacking uracil (Sc-ura), or synthetic complete medium lacking leucine and tryptophan and containing 5-FOA (Sc-L-T+FOA), as indicated.

Figure 4:
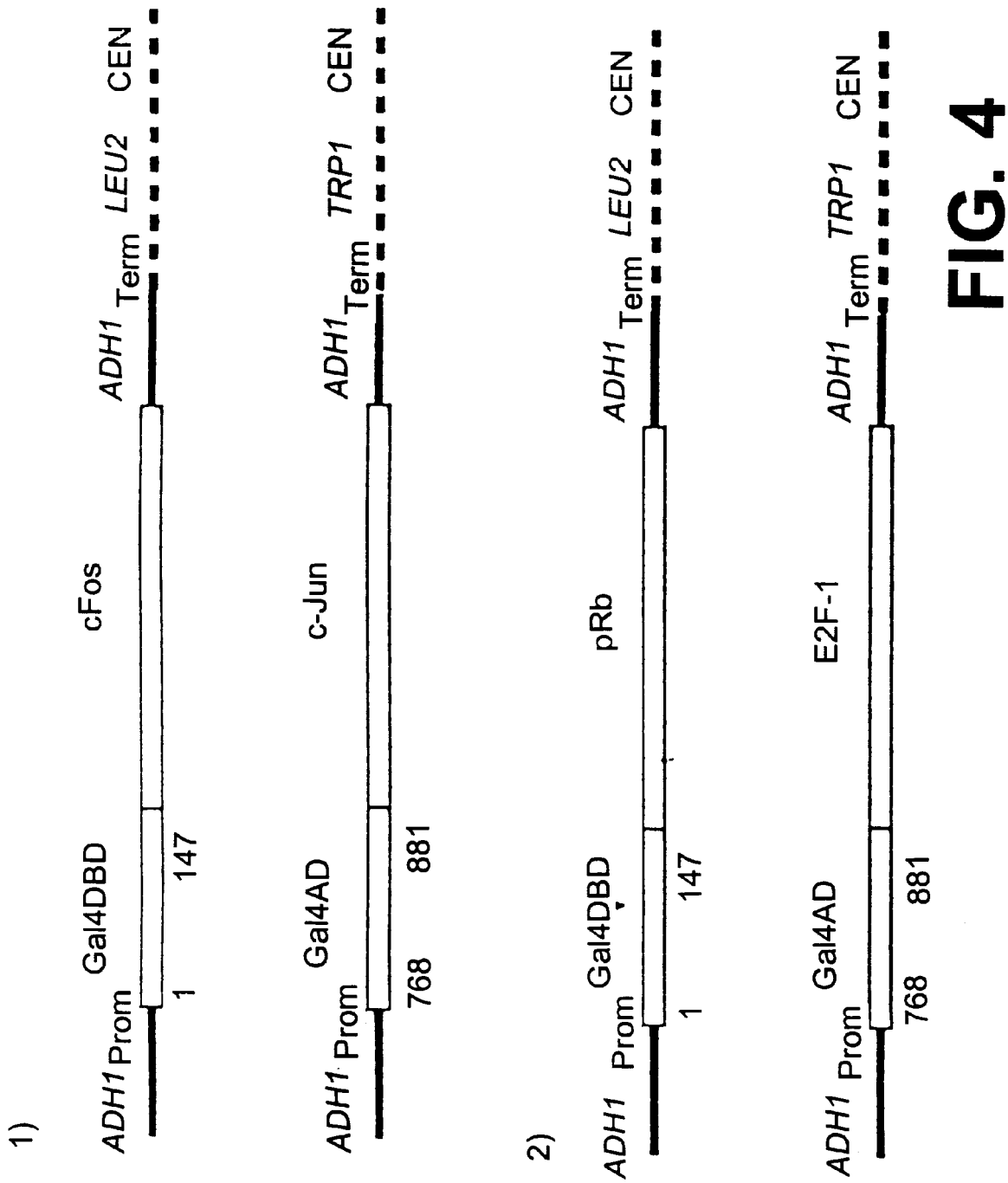

FIG. 4 is a schematic representation of the genetic constructs used to express DB-cFos, AD-cJun, DB-pRb, and AD-E2F1.

Figure 5:
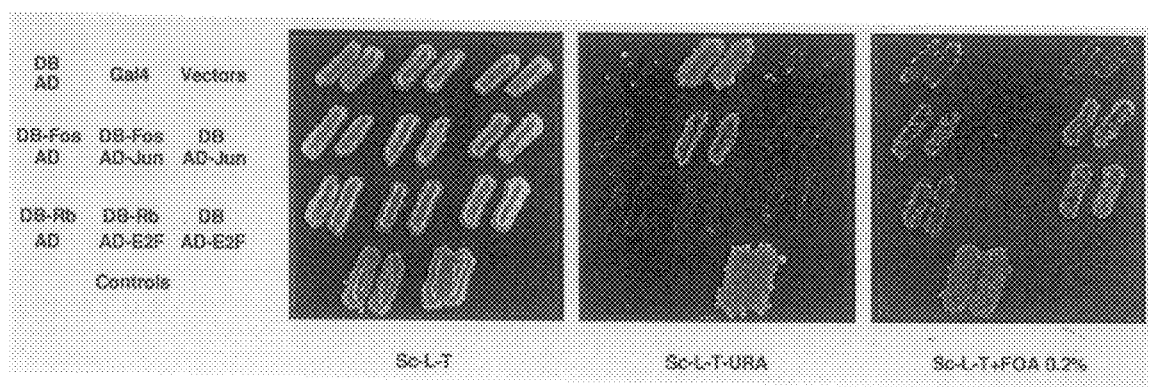

FIG. 5 is a photograph of yeast cells in which a GAL4 transcription factor was reconstituted with various interacting proteins. Reconstitution induces expression of the SPAL5:URA3 alleles and confers Foa$^s$ on the cells. Control strains are wild-type URA3 (two patches on right side of each panel) and ura3-52 mutant strains (two patches on left side of each panel). These experiments employ the yeast strain MaV103 which includes the counterselectable reporter gene SPAL9:URA3. The cells were grown on synthetic complete medium lacking leucine and tryptophan (Sc-L-T), synthetic complete medium lacking uracil (Sc-ura), or synthetic complete medium lacking leucine and tryptophan and containing 5-FOA (Sc-L-T+FOA), as indicated.

Figure 6:
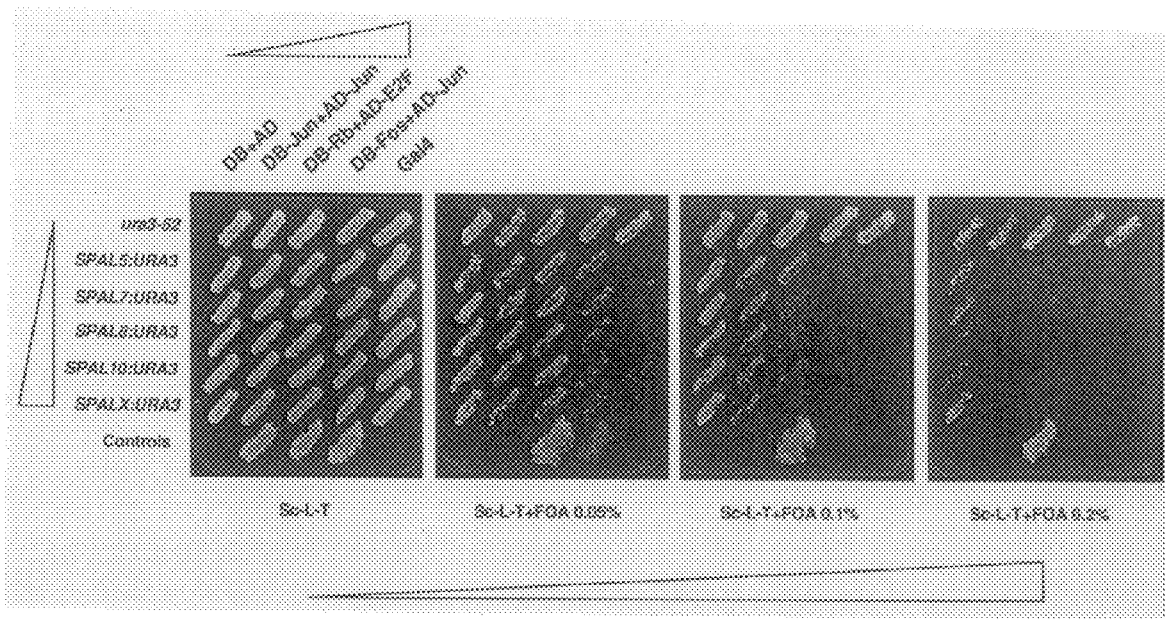

FIG. 6 is a photograph of yeast cells which define the limit of growth threshold on 5-FOA for various interacting proteins which reconstitute a transcription factor: cFos/cJun (0.05%), pRb/E2F1 (0.1%), and cJun/cJun (0.2%). Control strains are wild-type URA3 (two patches on right side of each panel) and ura3-52 mutant strains (two patches on left side of each panel). The cells were grown on synthetic complete medium lacking leucine and tryptophan (Sc-L-T), or synthetic complete medium lacking leucine and tryptophan and containing 5-FOA (Sc-L-T+FOA), with 5-FOA at the indicated concentrations.

Figure 7:
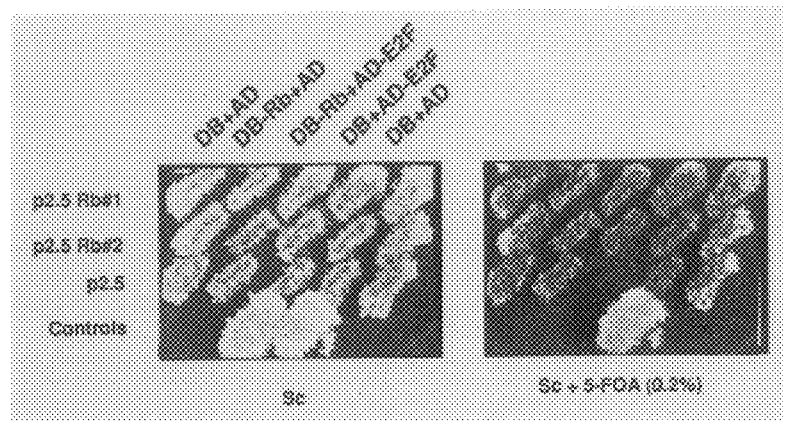

FIG. 7 is a photograph of yeast cells which indicates that the plasmid p2.5 can be used to express dissociator compounds in cells expressing molecules which, in the absence of a dissociator, would reconstitute a transcription factor. Control strains are wild-type URA3 (two patches on right side of each panel) and ura3-52 mutant strains (two patches on left side of each panel). The cells were grown on synthetic complete medium lacking leucine and tryptophan (Sc-L-T), synthetic complete medium lacking uracil (Sc-ura), or synthetic complete medium lacking leucine and tryptophan and containing 5-FOA (Sc-L-T+FOA), as indicated. Rb#1 and Rb#2 are two independent isolates of the construct encoding Rb.

Figure 8:
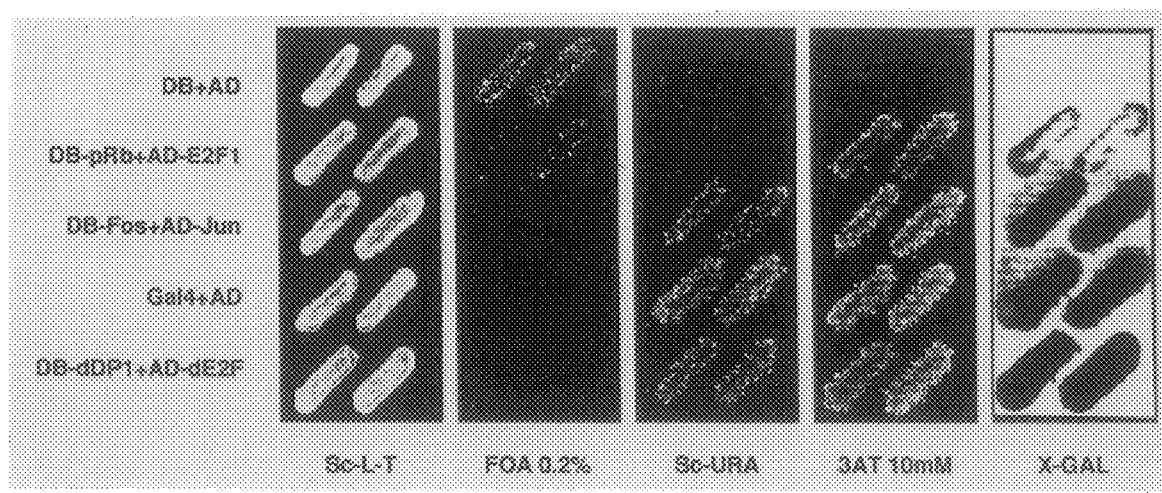

FIG. 8 is a photograph which shows the various phenotypes of the MaV103 strain of yeast expressing any of a variety of hybrid proteins under several different growth conditions. Plates designated as 3AT are Sc-L-T-H (lack leucine, tryptophan, and histidine), and contain 10 mm 3-amino triazole (3AT). Plates designated as X-gal contain Sc-L-T medium and contain 20 mg/ml 5-bromo-4-chloro-3-indolyl-β-D-galactopyranoside (X-gal) which serves as substrate for β-galactosidase.

Figure 9:
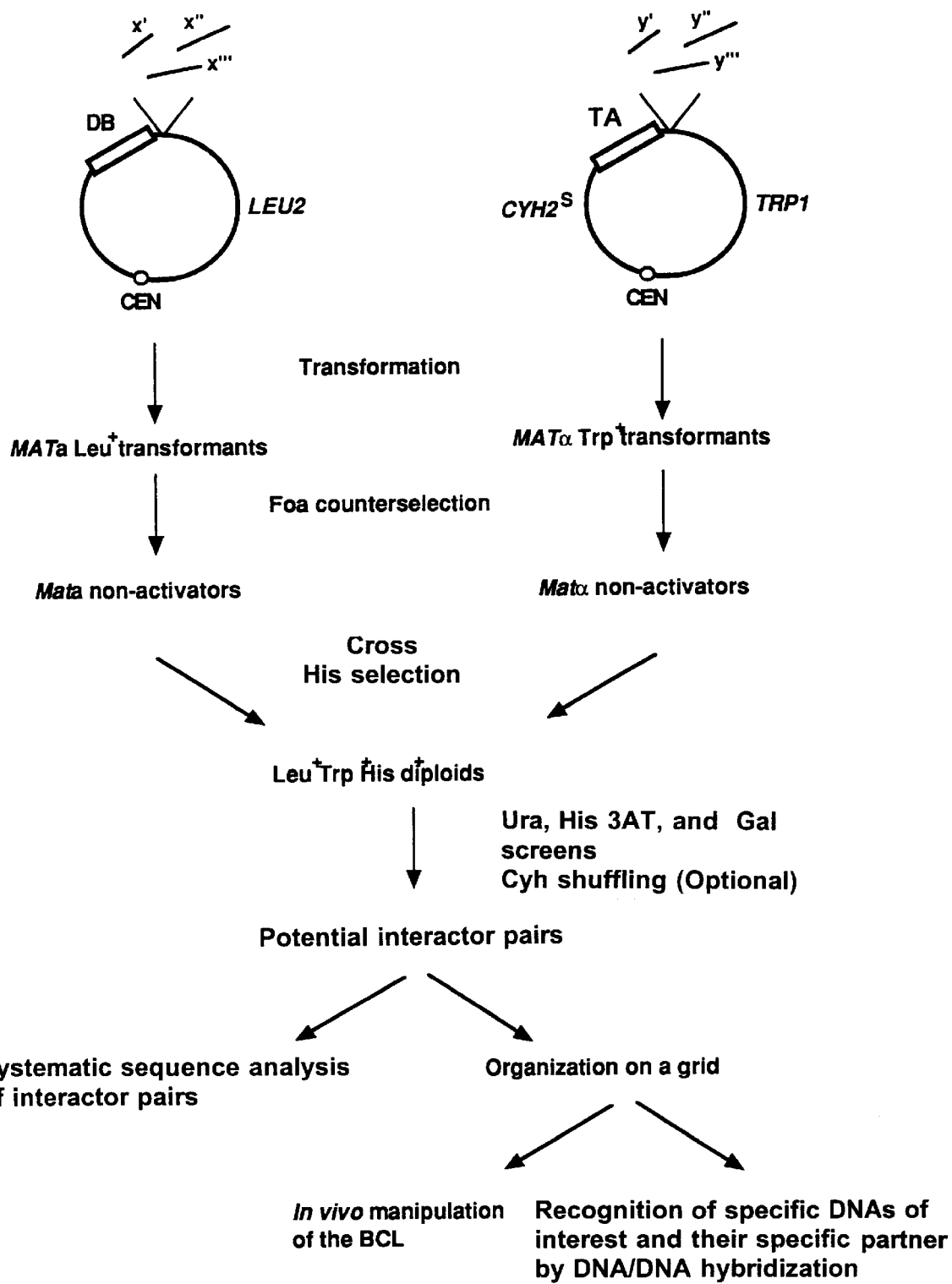

FIG. 9 is a schematic representation of an example of the reverse two-hybrid method used to generate a collection of interacting molecules (i.e., a bidirectional combinatorial library (BCL)).

Figure 10A:
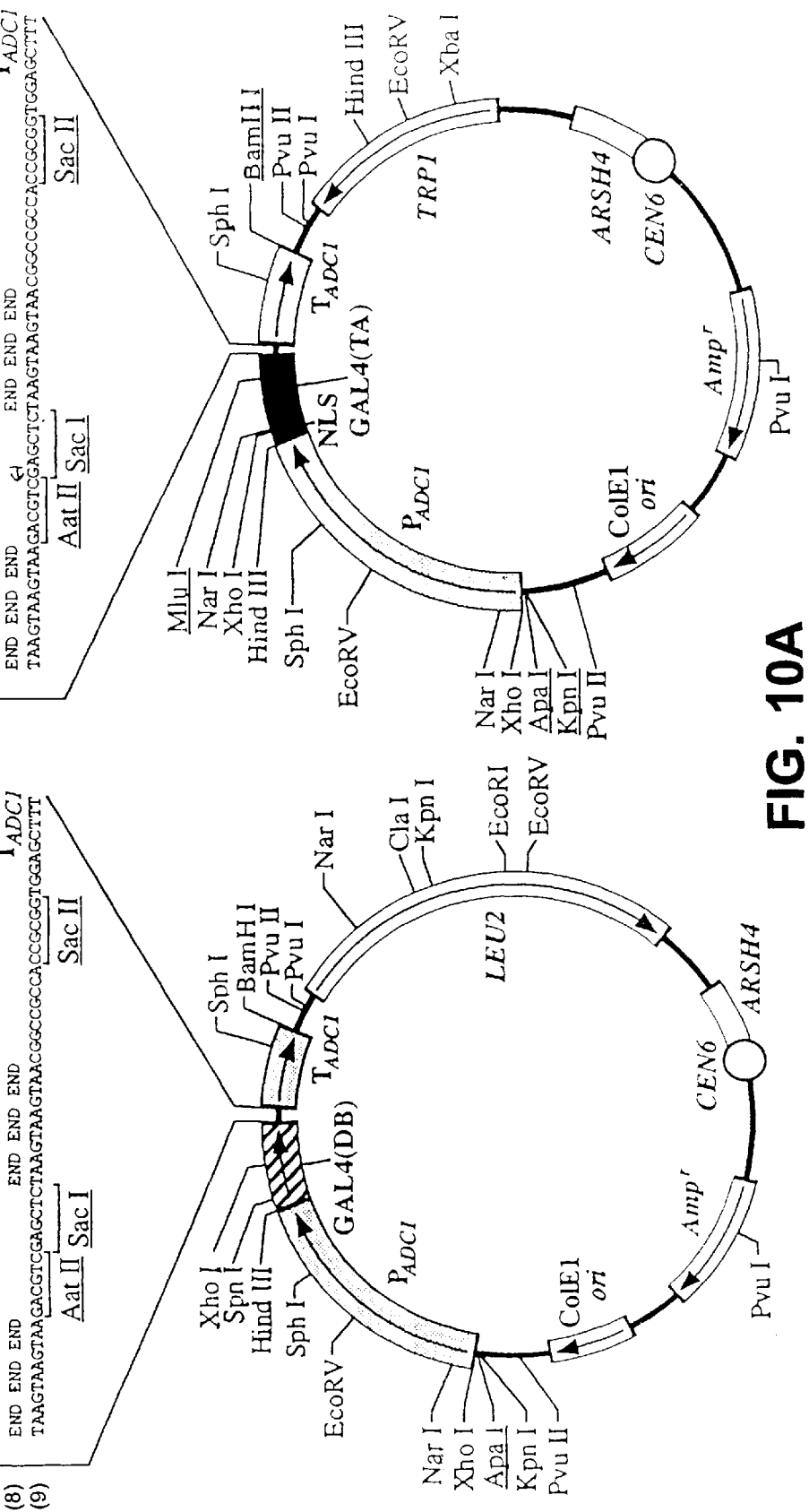
Figure 10B:
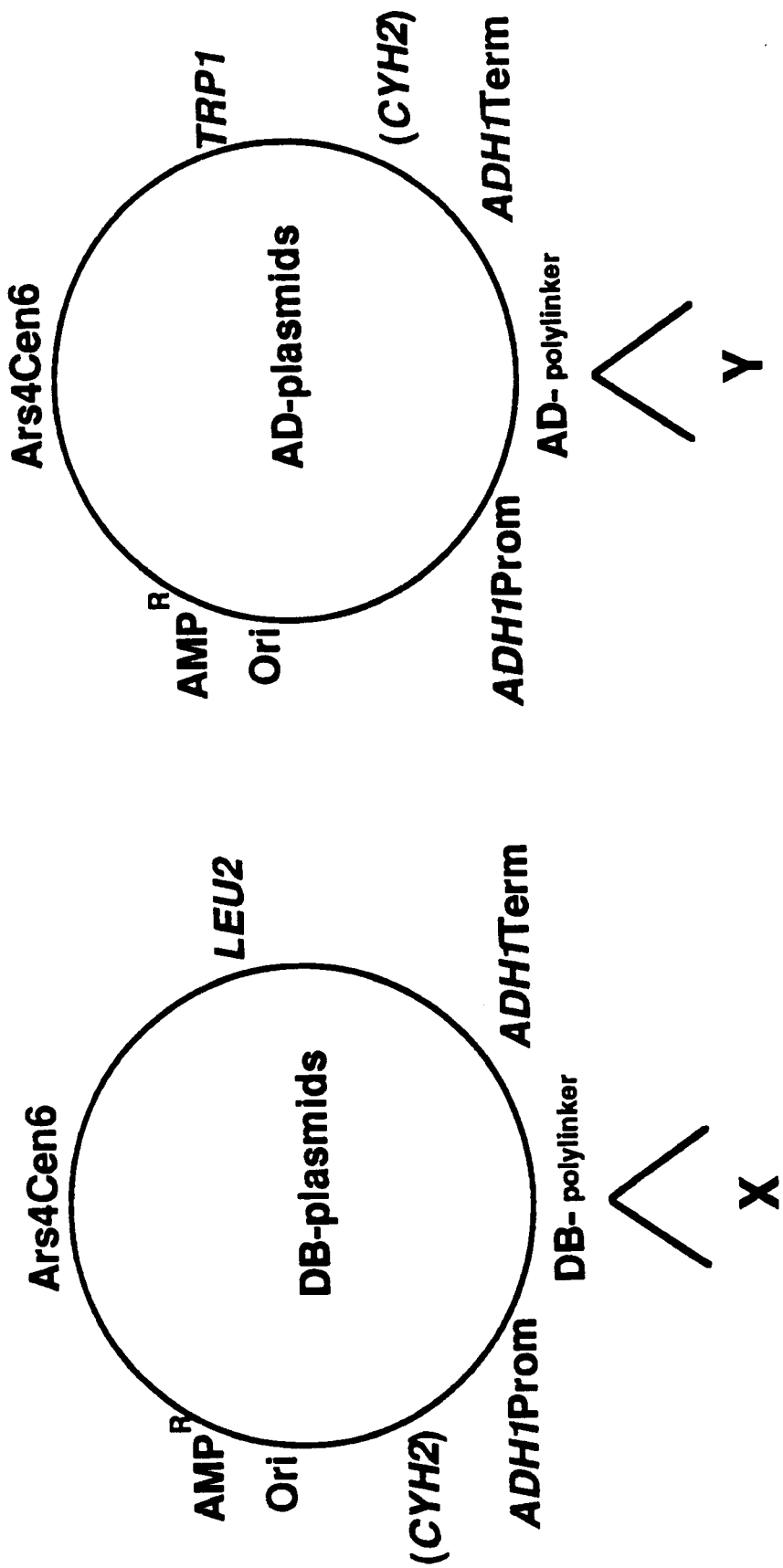

FIG. 10A is a schematic representation of plasmids into which the CYH2 counterselectable marker was inserted. A portion of pPC97 (left panel), containing a polylinker, is represented by SEQ ID NO: 7. The amino acid sequence encoded by this portion of pPC97 is represented by SEQ ID NO: 8. A portion of pPC86 (right panel), containing a polylinker, is represented by SEQ ID NO: 9. The amino acid sequence encoded by this portion of pPC86 is represented by SEQ ID NO: 10. FIG. 10B is a schematic representation of the plasmids used to create hybrid proteins with the GAL4-AD or GAL4-DB.

FIG. 11 is a chart summarizing the results of a unidirectional (i.e., classical) two-hybrid screen performed with MaV103. When compared to conventional two-hybrid systems, the number of positives was relatively low. "Retested" refers to clones that score positive for the three phenotypes. X→Y refers to the number of X clones identifying Y proteins.

Figure 12:
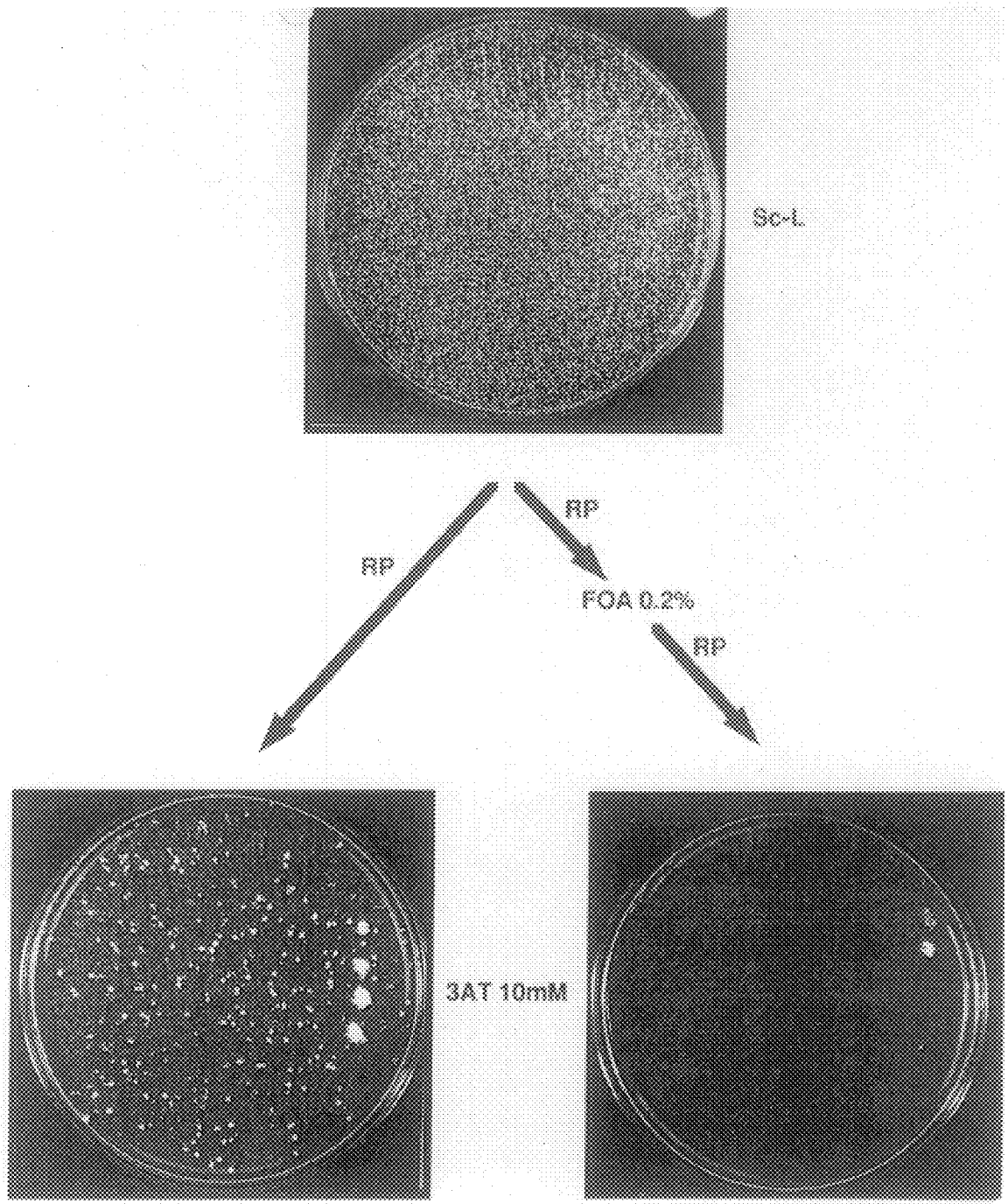

FIG. 12 is a photograph of yeast cells containing synthetic libraries which contain two self-activating clones. The bottom left panel is a photograph of a plate containing a Sc-L-T-H medium and which contains 3AT. The cells growing on the plate in the bottom-right panel were replica-plated from Sc-L to Sc-l+5-FOA to Sc-L-T-H+3AT. As a negative control, the Sc-L plate was also directly replica-plated onto 3AT plates lacking histidine, and the resulting cells are shown in the bottom left panel. The large patches on the right side of each plate represent control cells. From top to bottom, the controls are pPC97/pPC86, Db-pRb/AD-E2F1, Fos/Jun, and intact Gal4.

Figure 13:
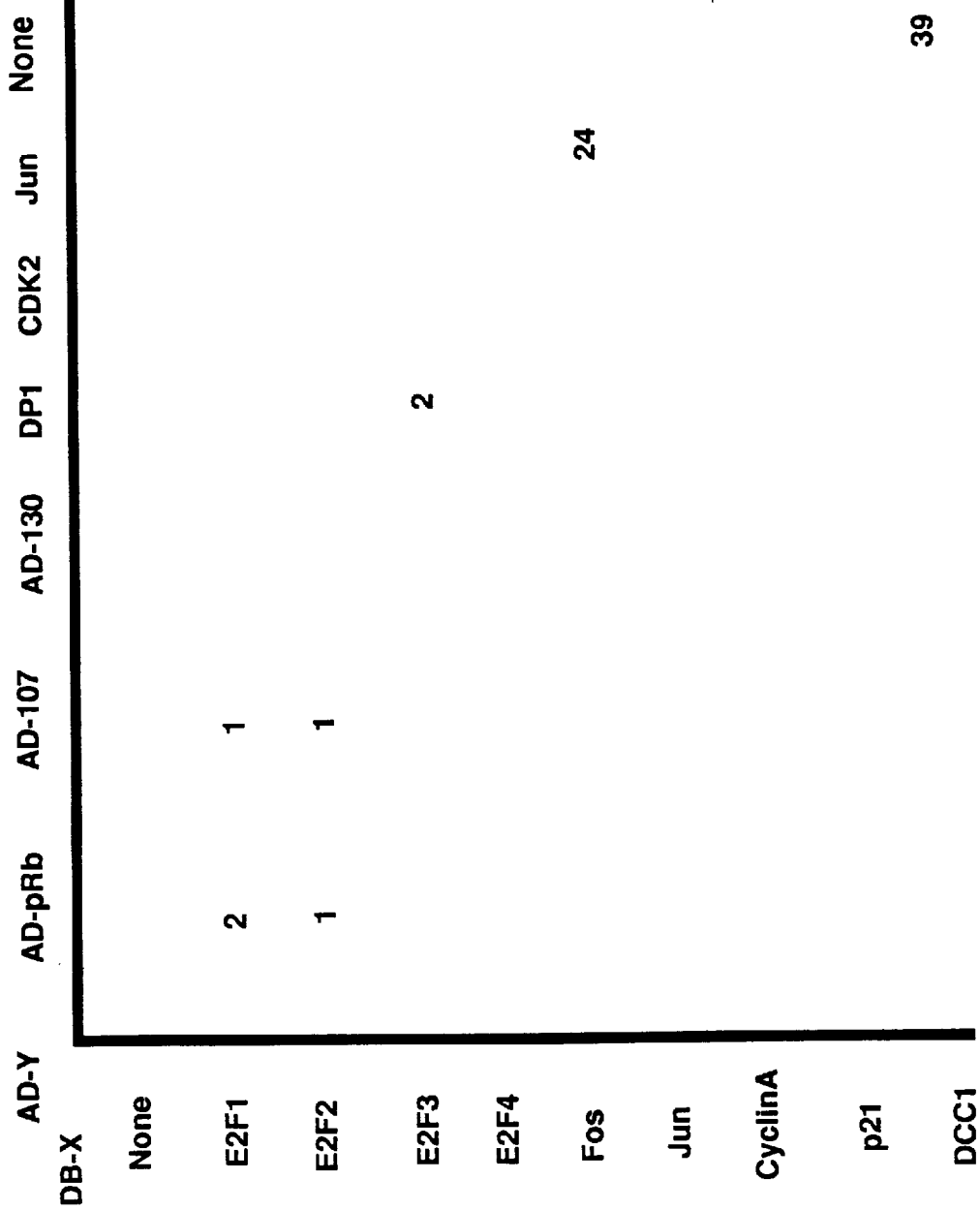

FIG. 13 is a chart which summarizes the interactions observed with the synthetic libraries.

Figure 14:
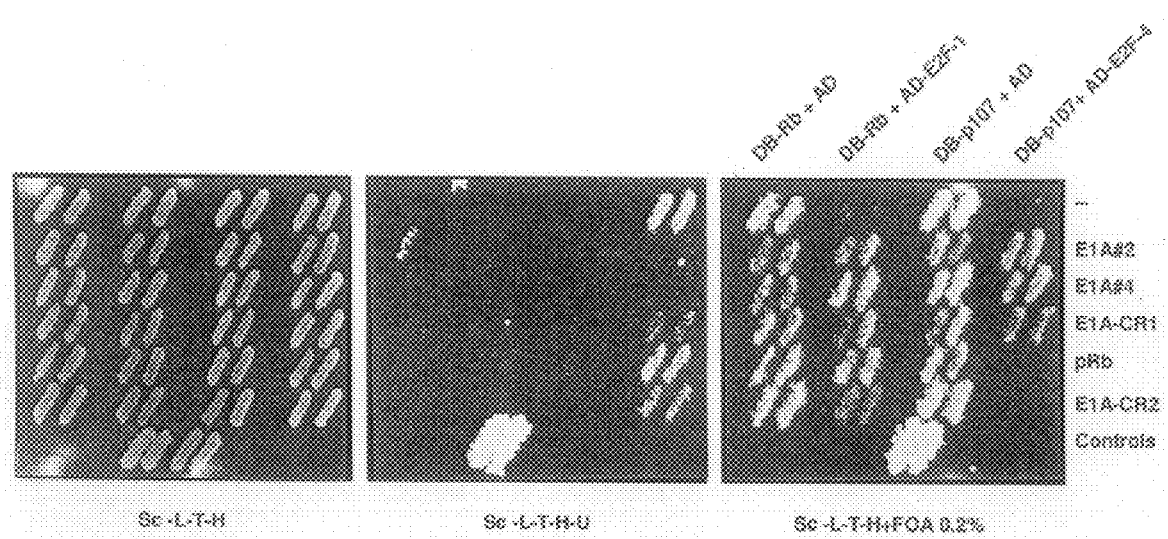

FIG. 14 is a photograph of yeast cells in which E1A is overexpressed in cells which expressed either AD-E2F1 and DB-pRb, or AD-E2F1 and DB-p107 hybrid molecules. Control strains are wild-type URA3 (two patches on right side of each panel) and ura3-52 mutant strains (two patches on left side of each panel). The cells were grown on synthetic complete medium lacking leucine and tryptophan (Sc-L-T), synthetic complete medium lacking uracil (Sc-ura), or synthetic complete medium lacking leucine and tryptophan and containing 5-FOA (Sc-L-T+FOA), as indicated. E1a#2 and E1a#4 refer to amino acids 30–132, and amino acids 30–86 and 120–139, respectively.

Figure 15:
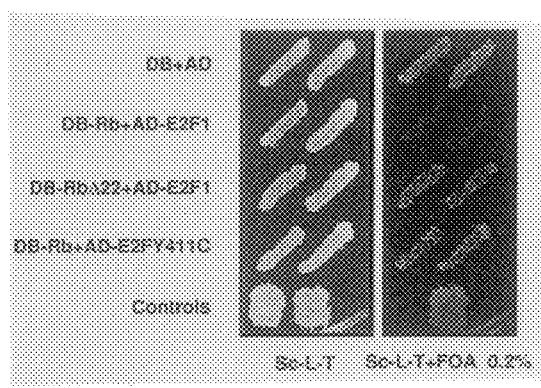

FIG. 15 is a photograph of yeast cells indicating that the inability of the mutant, pRbΔ22, to interact with E2F1 can be detected with the invention. Control strains are wild-type URA3 (patch on left side of each panel) and ura3-52 mutant strains (patch on right side of each panel). The cells were grown on synthetic complete medium lacking leucine and tryptophan (Sc-L-T), synthetic complete medium lacking uracil (Sc-ura), or synthetic complete medium lacking leucine and tryptophan and containing 5-FOA (Sc-L-T+FOA), as indicated.

Figure 16:
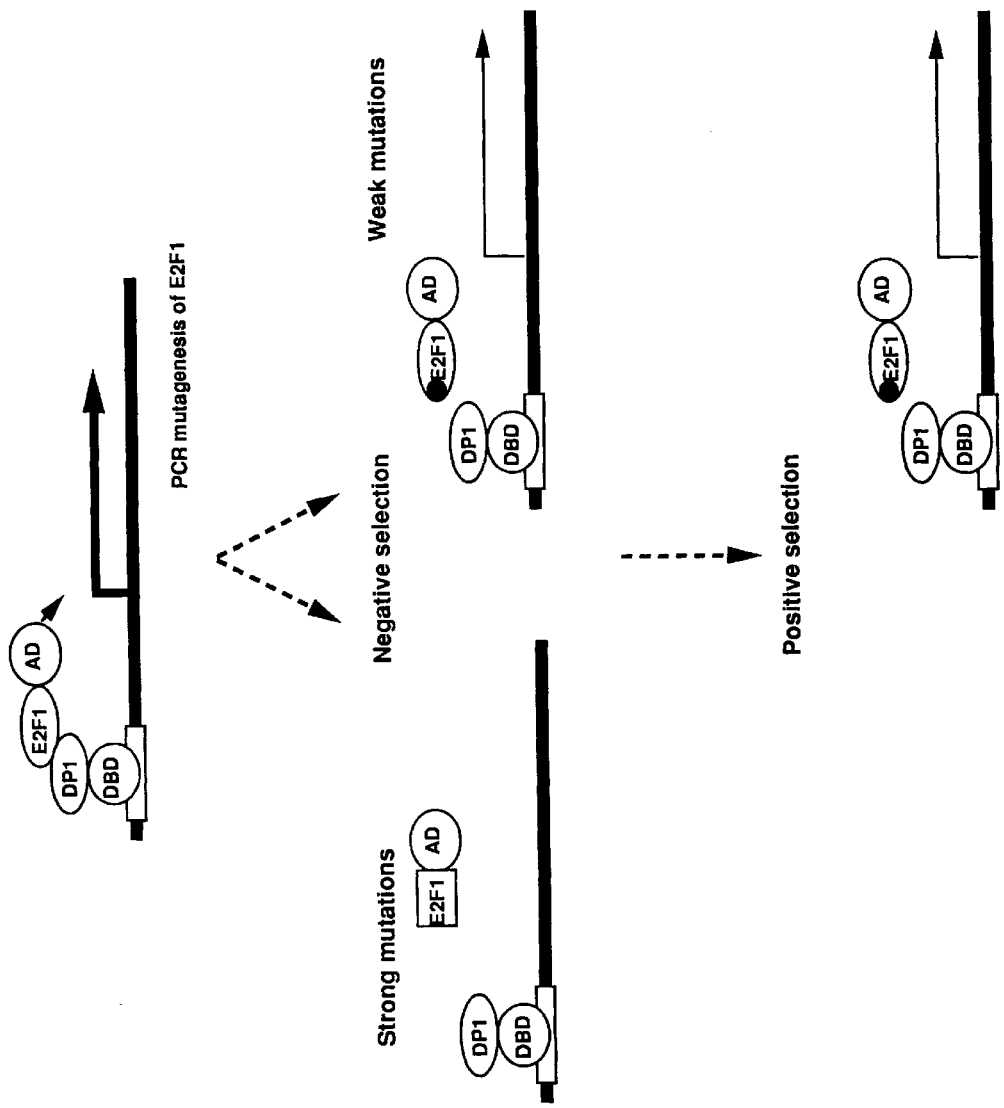

FIG. 16 is a schematic representation of a two-step selection method used to identify residues in E2F1 which mediate its ability to interact with DP1.

Figure 17:
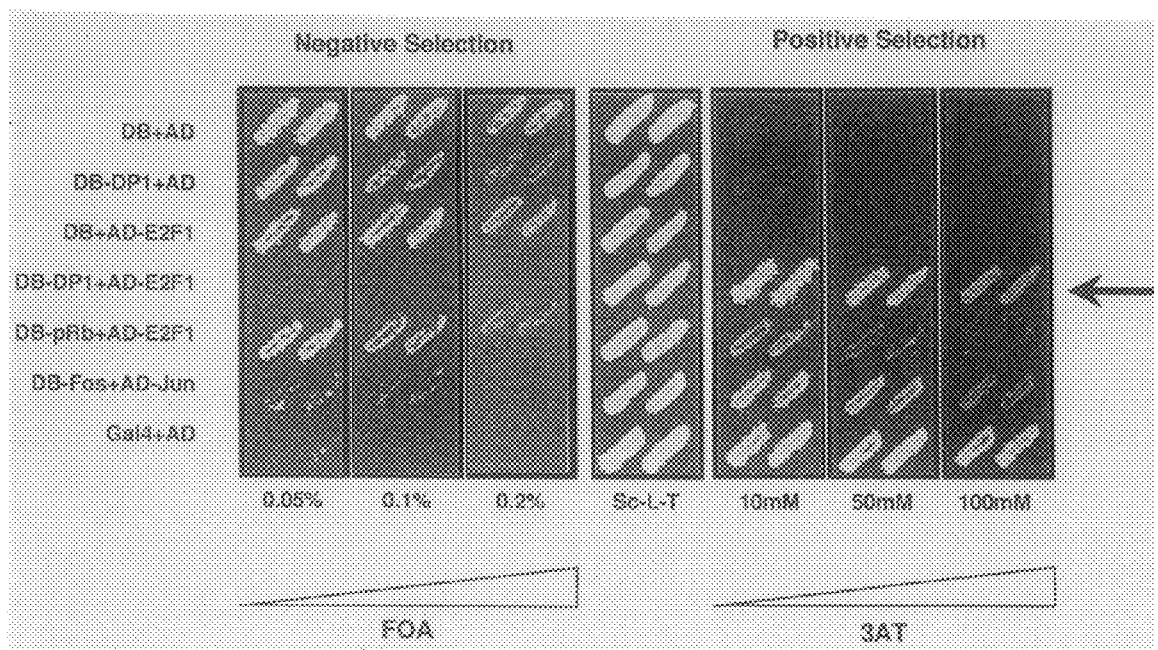

FIG. 17 is a photograph of yeast cells indicating that the GAL1:HIS3 and the SPAL9:URA3 reporter genes confer "titratable" phenotypes.

Figure 18A:
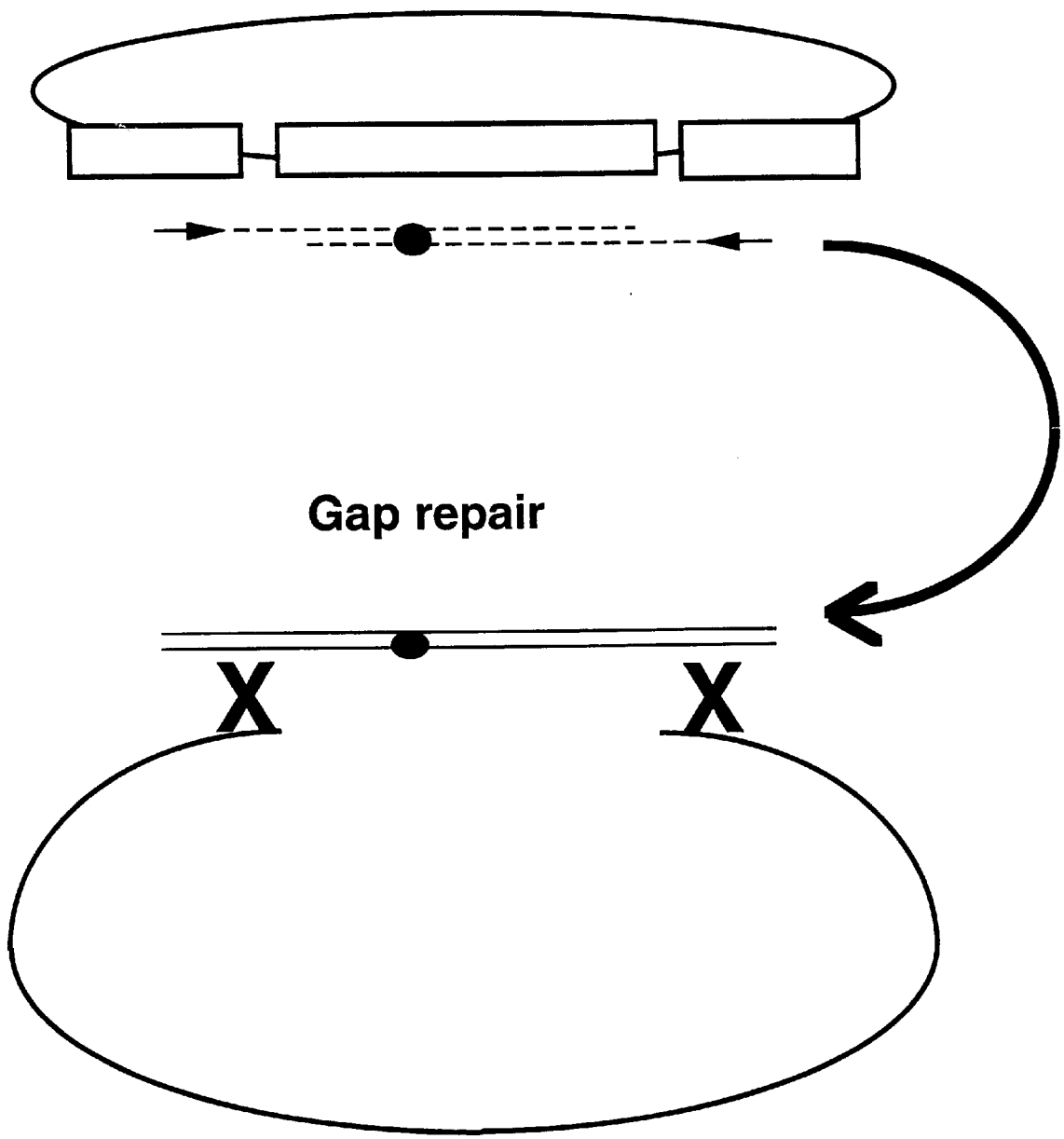
Figure 18B:
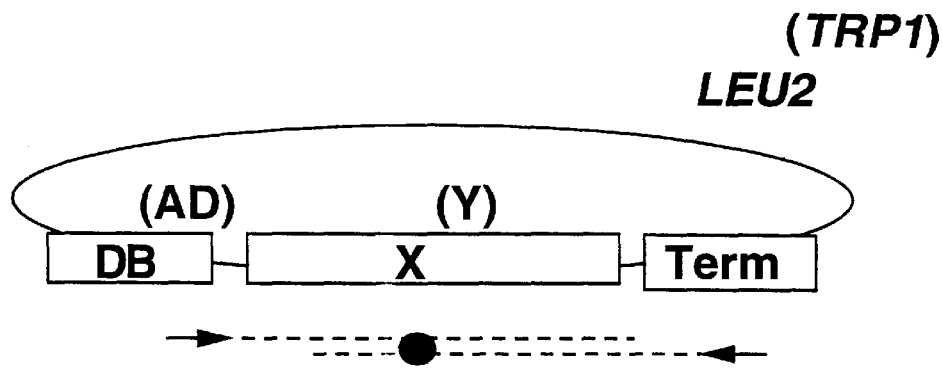
Figure 18B:
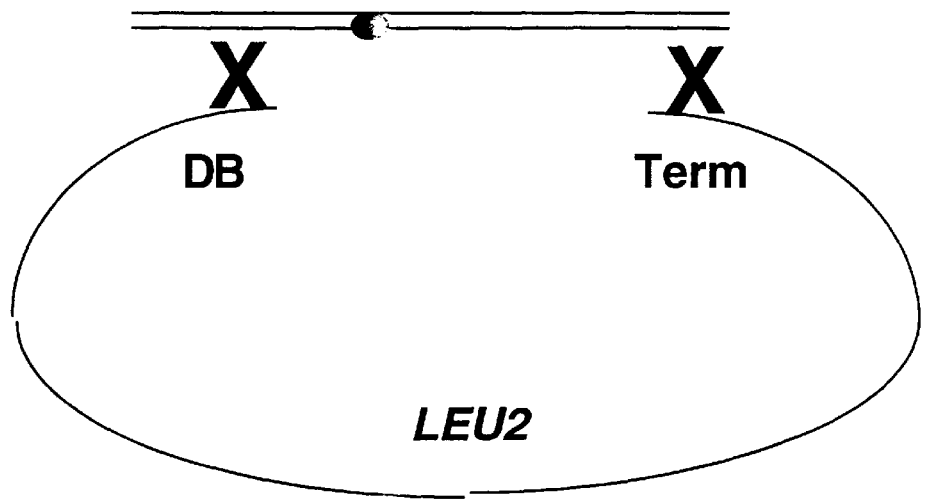

FIGS. 18A and 18B are schematic representations of the strategies used for PCR mutagenesis and in vivo gap repair.

Figure 19:
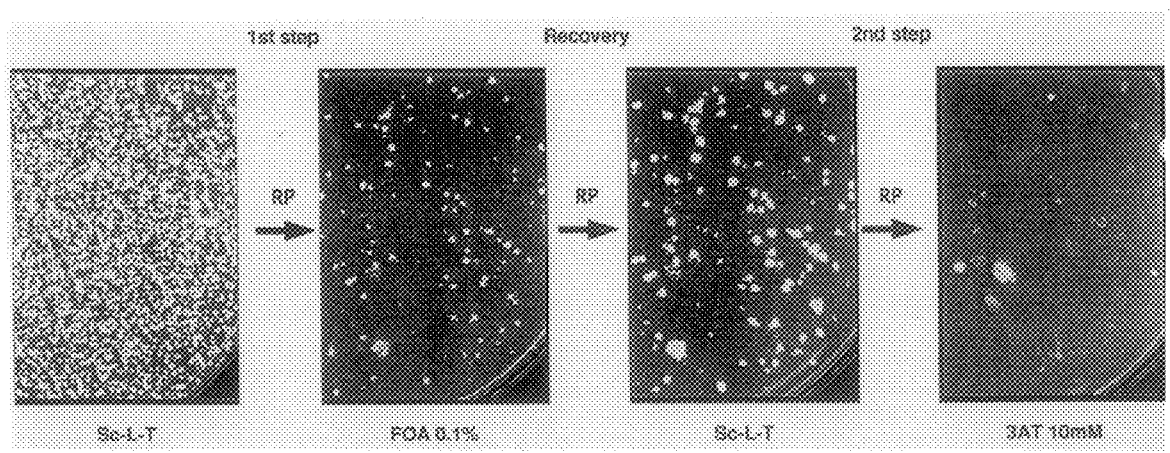

FIG. 19 is a series of photographs showing growth of yeast cells in the first and second steps of the two-step selection method. At each step, surviving colonies were transferred by replica-plating (RP). Control strains are wild-type URA3 (two patches on right side of each panel) and ura3-52 mutant strains (two patches on left side of each panel). The cells were grown on synthetic complete medium lacking leucine and tryptophan (Sc-L-T), synthetic complete medium lacking uracil (Sc-ura), or synthetic complete medium lacking leucine and tryptophan and containing 5-FOA (Sc-L-T+FOA), as indicated.

Figure 20:
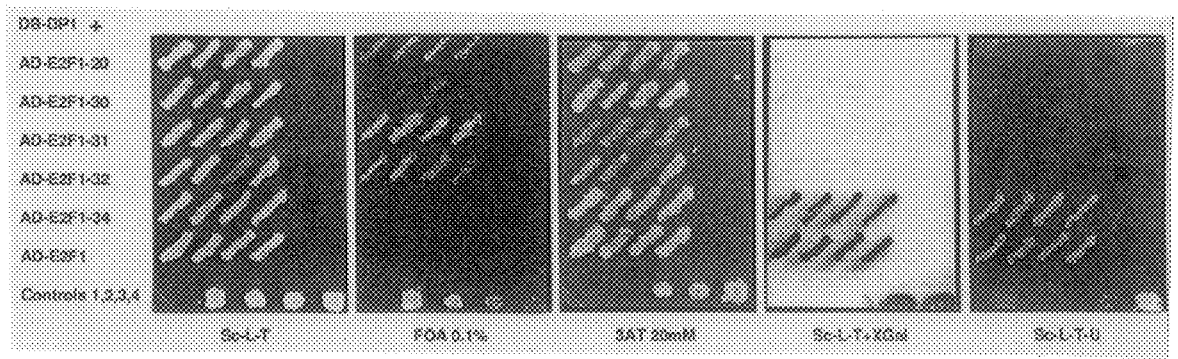

FIG. 20 is a series of photographs which display the phenotypes of the E2F1 alleles obtained in the second step of the two-step selection method.

FIG. 21 is a schematic representation of the Marked Box 2 domain and the mutations obtained with the two-step selection method. The amino acid sequences of the Marked Box 2 domains of E2F5, E2F4, E2F2, and E2F1 are represented by SEQ ID NOS: 11–15, respectively. The amino acid sequences of the Marked Box 2 domains of the alleles E2F1-20, E2F1-30, E2F1-32, and E2F1-65 are represented by SEQ ID NOS: 16–19, respectively.

Figure 22:
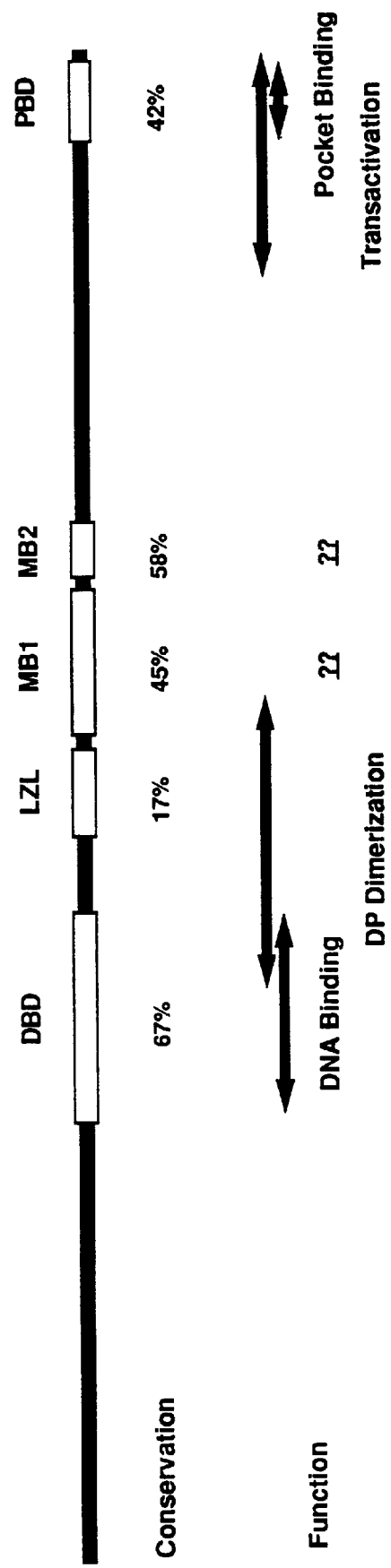

FIG. 22 is a schematic representation of E2F1 and its previously described functional domains.

Figure 23A:
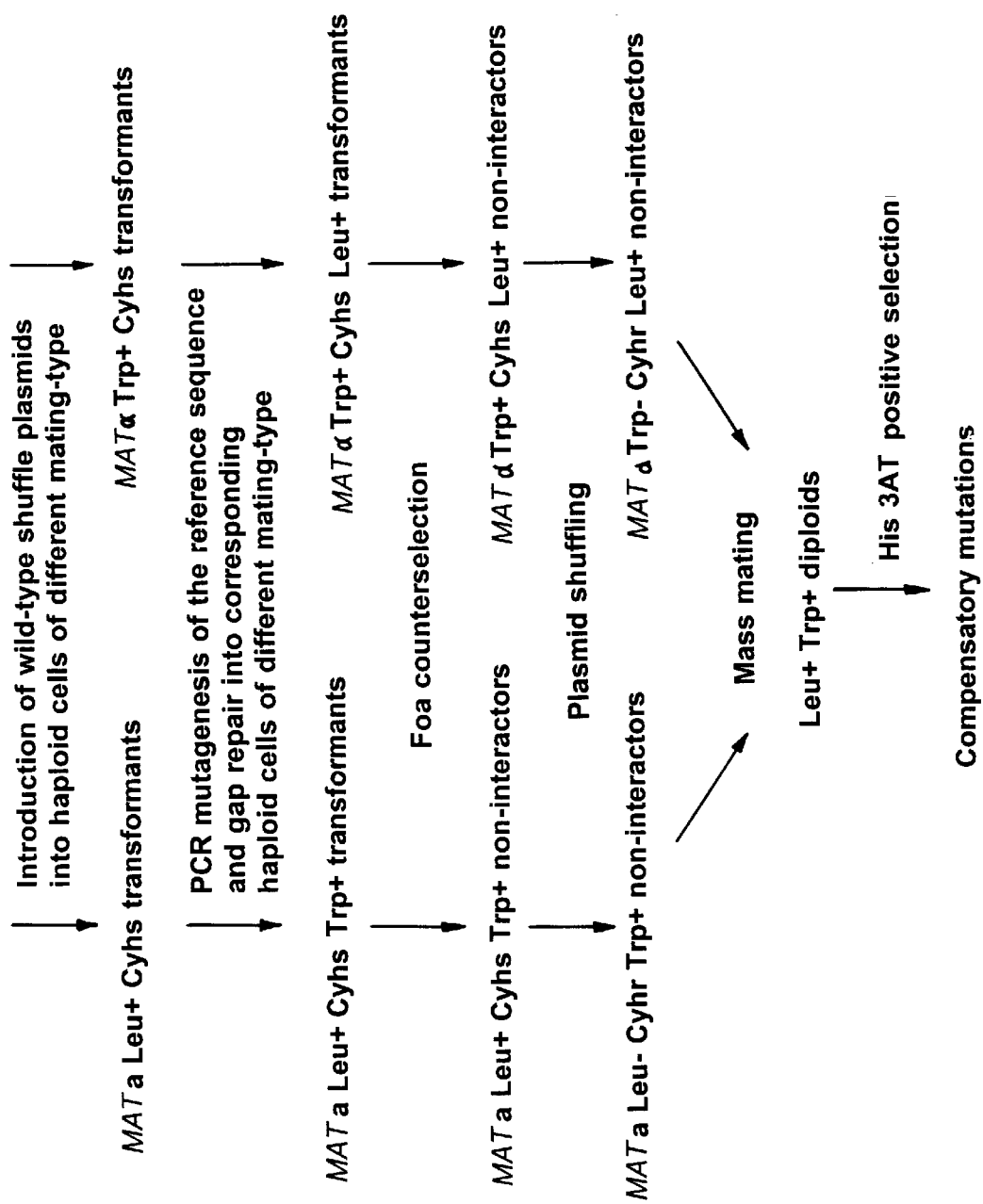
Figure 23B:
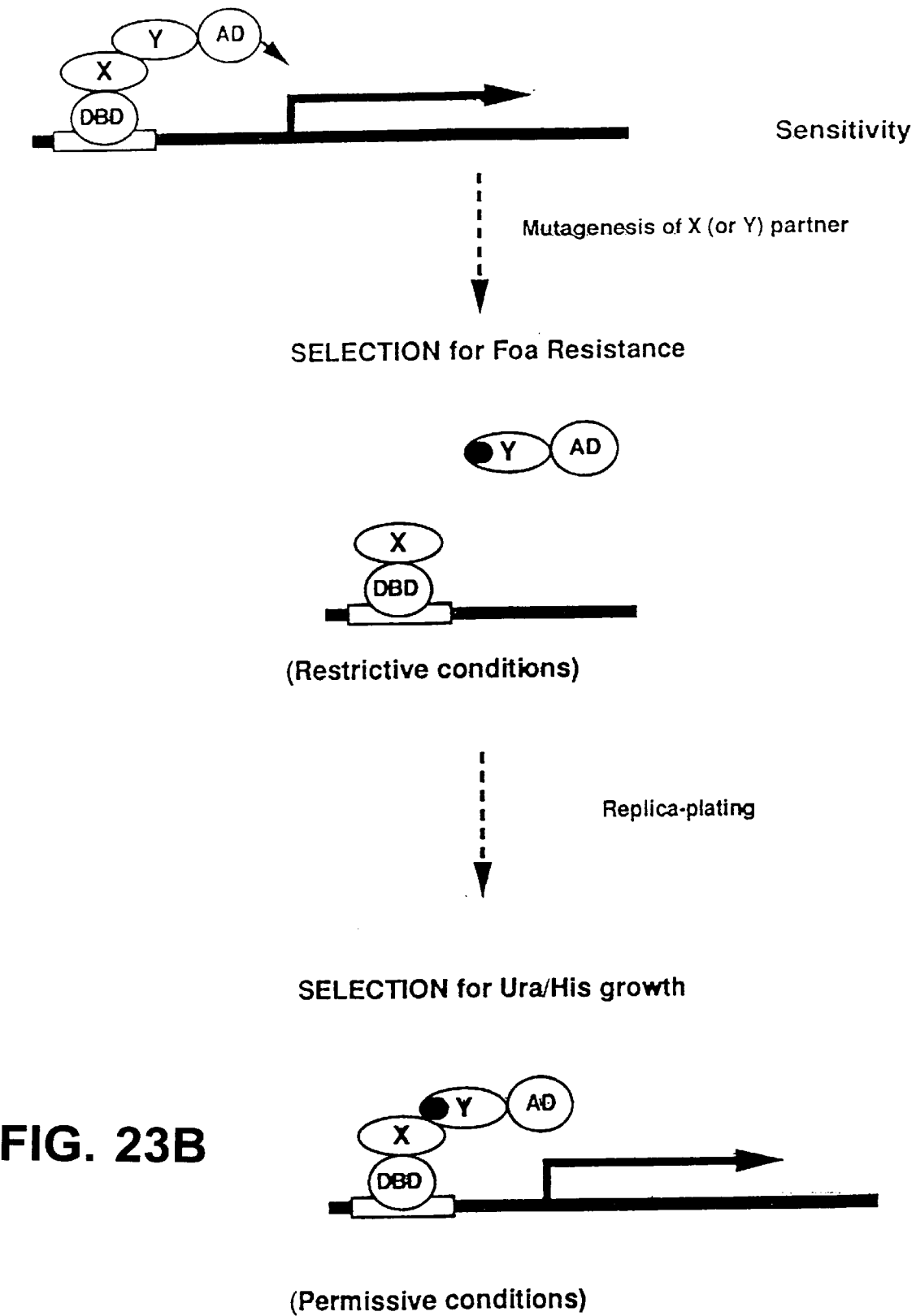

FIG. 23A is a chart summarizing a two-step selection method. FIG. 23B is a schematic representation of a two-step method for identifying conditional alleles (i.e., CATS).

Figure 24:
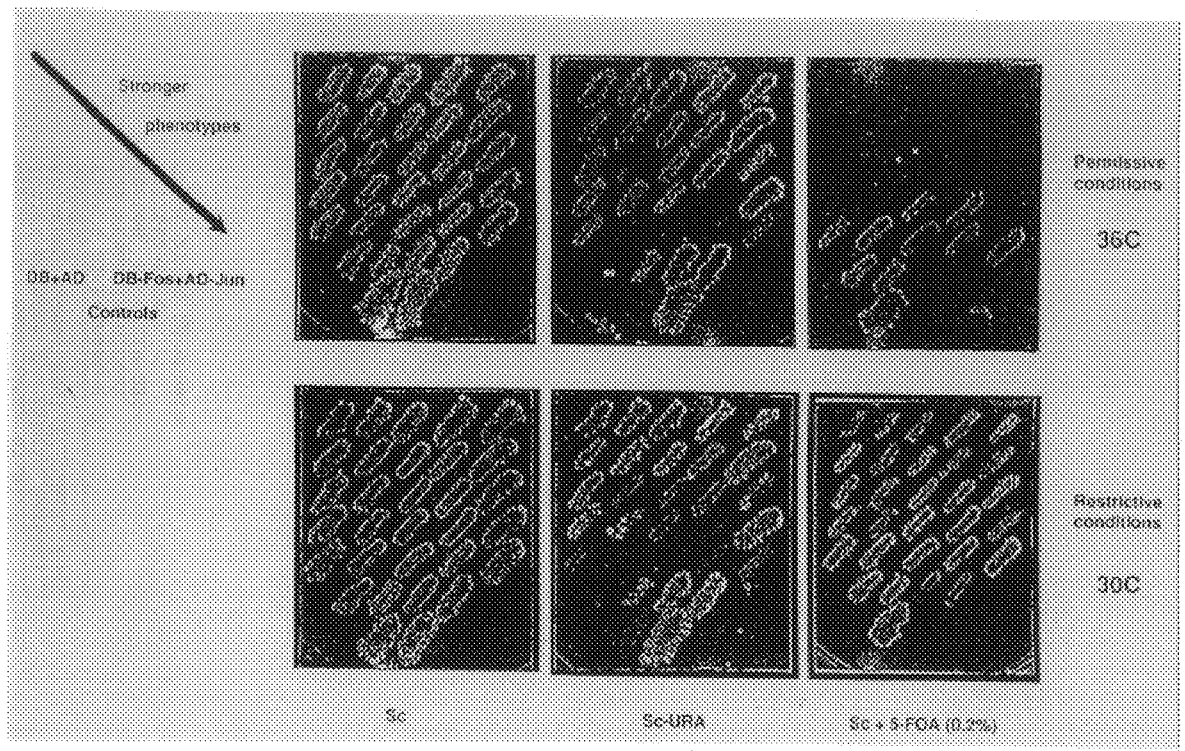

FIG. 24 is a series of photographs of yeast cells expressing DB-Fos and conditional alleles of AD-Jun. This figure indicates that a conditional allele of Jun prevents AD-Jun and DB-Fos from interacting at 30° C. but not at 36° C.

Figure 25:
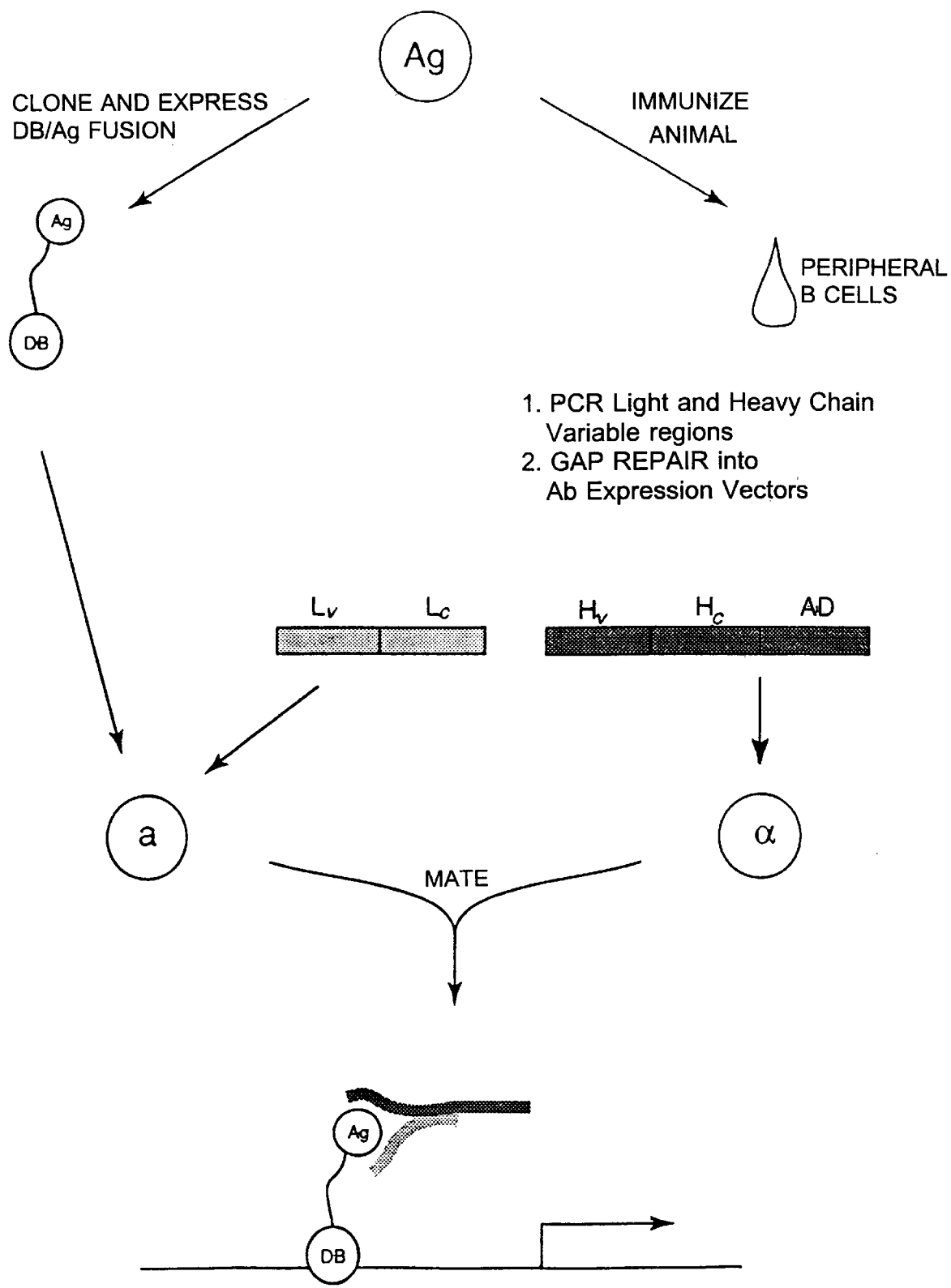

FIG. 25 is a schematic representation of a strategy useful for identifying antigen/antibody interactions.

ABBREVIATIONS

Abbreviations used herein include:
AA amino acid
AD activation domain
DB, DBD DNA-binding domain
5-FOA 5-fluoro-orotic acid
GBS GAL4 binding sequence
ORF open reading frame
URS upstream repressing sequence
Prom promoter
Term terminator
CEN centromere
ARS yeast origin of replication
RP replica-plate
2 mu yeast 2 micron plasmid origin of replication
ORI bacterial origin of replication
3AT 3-amino triazole Before providing detailed examples of the invention, several parameters of the invention are described.

Standard Two-hybrid System: The yeast two-hybrid system has been used to detect the association of pairs of proteins (see, e.g., Fields et al., U.S. Pat. No. 5,283,173). This method involves in vivo reconstitution of two separable domains of a transcription factor. The DNA binding domain (DB) of the transcription factor is required for recognition of a chosen promoter. The activation domain (AD) is required for contacting other components of the cell's transcriptional machinery. In this system, the transcription factor is reconstituted through the use of hybrid proteins. One hybrid is composed of the AD and a first protein of interest. The second hybrid is composed of the DB and a second protein of interest. In cases where the first and second proteins of interest interact with each other, the AD and DB are brought into close physical proximity, thereby reconstituting the transcription factor. Association of the proteins can be measured by assaying the ability of the reconstituted transcription factor to activate transcription of a reporter gene.

Useful reporter genes are those which are operably linked to a promoter that is specifically recognized by the DB. Typically, the two-hybrid system employs the yeast *Saccharomyces cerevisiae* and reporter genes whose expression can be selected under appropriate conditions. The two-hybrid system provides a convenient method for cloning a gene encoding a protein which interacts with a second, preselected protein. In such an experiment, a cDNA library is constructed in order to fuse randomly generated sequences to the AD, and the protein of interest is fused to the DB. In this "unidirectional" screening method, proteins expressed from one library of clones are tested for their ability to interact with one pre-selected protein of interest. Methods employing two libraries of clones (one fused to the AD and one fused to the DB) have not been described.

Reporter Genes: The reporter genes described herein can be located on a plasmid or can be integrated into the genome of a haploid or diploid cell. The reporter gene whose expression is to be assayed is operably linked to a promoter which has sequences that direct transcription of the reporter gene. The reporter gene is positioned such that it is expressed when a gene activating moiety of a transcription factor is brought into close proximity to the gene (e.g., by using hybrid proteins to reconstitute a transcription factor, or by covalently bonding the gene-activating moiety to a DNA-binding protein). The reporter gene can also be operably linked to regulatory sequences which render it highly responsive to the presence or absence of a transcription factor. For example, in the absence of a specific transcription factor, a highly responsive URA3 allele confers a Ura$^-$ Foa$^r$ phenotype on the cell. In the presence of a specific transcription factor, a highly responsive URA3 allele confers a Ura$^+$ Foa$^s$ phenotype on the cell. Where the cell carrying the reporter gene (i.e., a transformed yeast cell) normally contains a wild-type copy of the gene (e.g., the URA3 gene), the exogenous reporter gene can be integrated into the genome and replace the wild-type gene. Conventional methods and criteria can be used to connect a reporter gene to a promoter and to introduce the reporter gene into a cell.

Promoters: Suitable promoters for expression of a reporter gene are those which, when linked to the reporter gene, can direct transcription of it in the presence of appropriate molecules (i.e., proteins having transcriptional activation domains), and which, in the absence of a transcriptional activation domain, do not direct transcription of the reporter gene. An example of a useful promoter is the yeast SPO13 promoter. Other useful promoters include those promoters which contain upstream repressing sequences (see, e.g., Vidal et al., 1995, Proc. Natl. Acad. Sci. USA 92:2370–2374) and which inhibit expression of the reporter gene in the absence of a transcriptional activation domain. The ability of a promoter to direct transcription of a reporter gene can be measured with conventional methods of assaying for gene expression (e.g., detection of the gene product or its mRNA, or detection of cell growth under conditions where expression of the reporter gene is required for growth of a cell).

Conventional molecular biology techniques can be used to construct derivatives of promoters which include one or more DNA-binding-protein recognition sites. For example, the SPO13 promoter can be engineered to include one or more copies of the GAL4 binding sequence (GBS). The DNA binding sites in natural promoters for GAL4 have been extensively characterized, allowing the creation of a synthetic sequence to which GAL4 binds with relatively high affinity. URA3 alleles that are operably linked to a SPO13 promoter are referred to as SPALX:URA3, for SPO13/G AL/URA3; X represents the number of GBSs present in the promoter. Other useful DNA-binding-protein recognition sites include the LexA and Ace1 binding sites. In addition, where the ability of a protein to bind to a DNA sequence is measured, the DNA-binding-protein recognition site can be a wild-type DNA-binding-protein recognition site, or it can be any intentionally-designed or randomly-generated sequence of interest in order to test the ability of the DNA sequence to interact with a protein.

Yeast Strains: The yeast strains used in the invention can be grown and maintained with standard methods. *Saccharomyces cerevisiae* are particularly useful in the invention. In certain aspects of the invention, mating of two mating competent yeast cells is desired. For example, in certain methods, a hybrid protein which includes an activation domain is expressed in one mating competent cell, and a hybrid protein which includes a DNA-binding domain is expressed in a second mating competent cell. In such a case, the transcription factor is reconstituted by mating the first and second mating competent cells. Obviously, the two mating competent cells should be of compatible mating types. For example, one mating competent cell can be of the MATa mating type, and the other mating competent cell can be of the MATα mating type. It is inconsequential which hybrid protein is expressed in which cell type.

Figure 1:
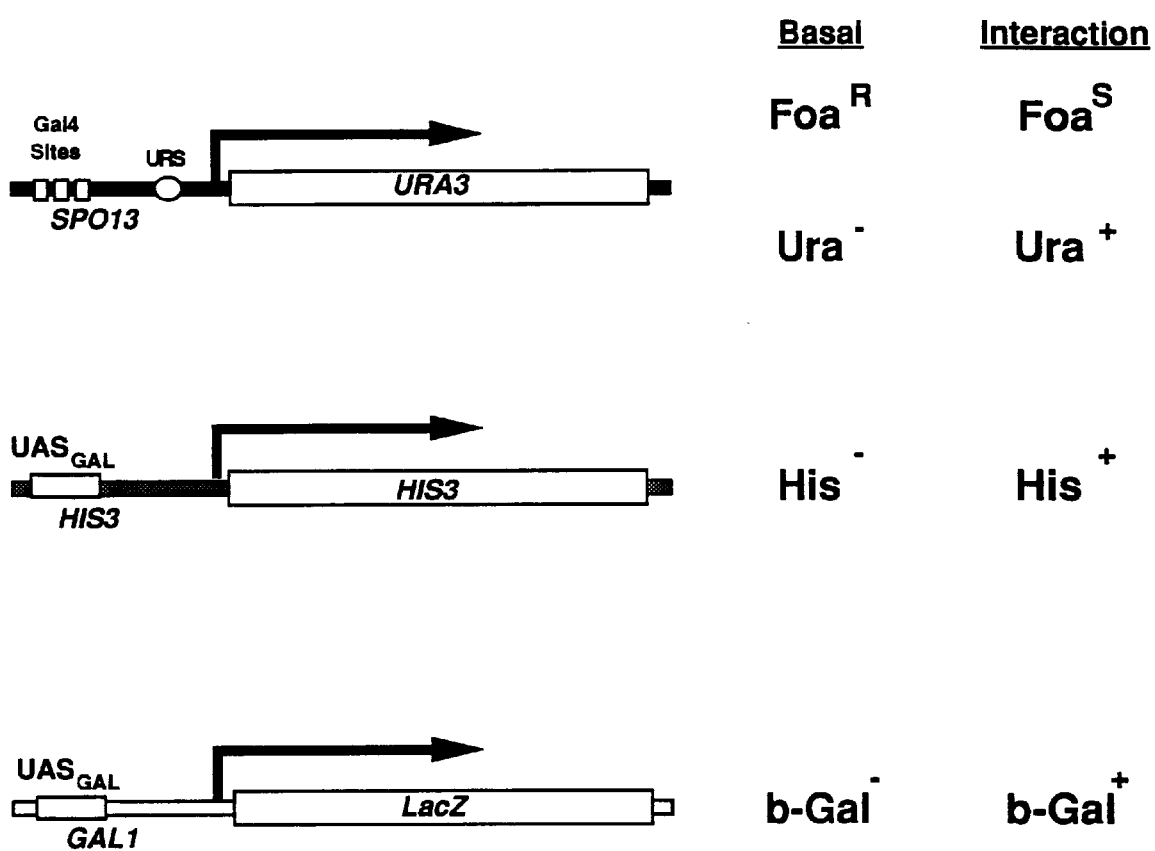
FIG. 1 is a schematic representation of three reporter genes that are operably linked to promoters having different sequences with the exception of the DNA-binding-protein recognition sequences.

A preferred yeast cell for characterizing molecular interactions has, integrated into its genome, a counterselectable reporter gene which is operably linked to a promoter which has (i) an upstream repressing sequence, and (ii) a DNA-binding-protein recognition site. The preferred yeast cell lacks (i) a naturally-occurring protein which is substantially identical to the protein encoded by the counterselectable reporter gene, and (ii) at least one naturally-occurring protein which, when it is expressed (e.g., from a plasmid), confers a growth advantage on a cell containing it. In addition, a yeast cell can contain, integrated into its genome, a selectable marker (e.g., HIS3) and/or a gene whose expression can be screened (e.g., lacZ). Where three such genes (i.e., a counterselectable reporter gene, a selectable marker, and a screenable marker) are integrated into the genome of a cell, it is preferred that the promoters of the three genes be distinct with the exception of the DNA-binding-protein recognition site (FIG. 1). The use of distinct promoters decreases the likelihood of obtaining false positives.

We have constructed a set of yeast strains having the following features: (i) a set of non-reverting auxotrophic mutations for selection of the two plasmids expressing the two-hybrids and dependence upon GAL1:HIS3 expression on medium lacking histidine: leu2, trp1, and his3; (ii) two recessive drug resistance mutations (can1 and cyh2) to facilitate plasmid shuffling; and (iii) three integrated GAL4-inducible reporter genes (Gal1:HIS3, Gal1:lacZ, and SPAL:URA3; FIG. 1). Yeast strains of both mating types (MATα and MATa) having these features were constructed.

Of particular use in the invention are the yeast strains MaV103 and MaV203, described below. Where uptake of a test compound (e.g., a potential dissociator) is desired, the erg6 mutant strain is particularly useful because of its relatively high ability to take up compounds. Other methods of permeabilizing the yeast cell may also be employed; these include treatment with chemicals such as polymixin B nonapeptide.

Figure 2:
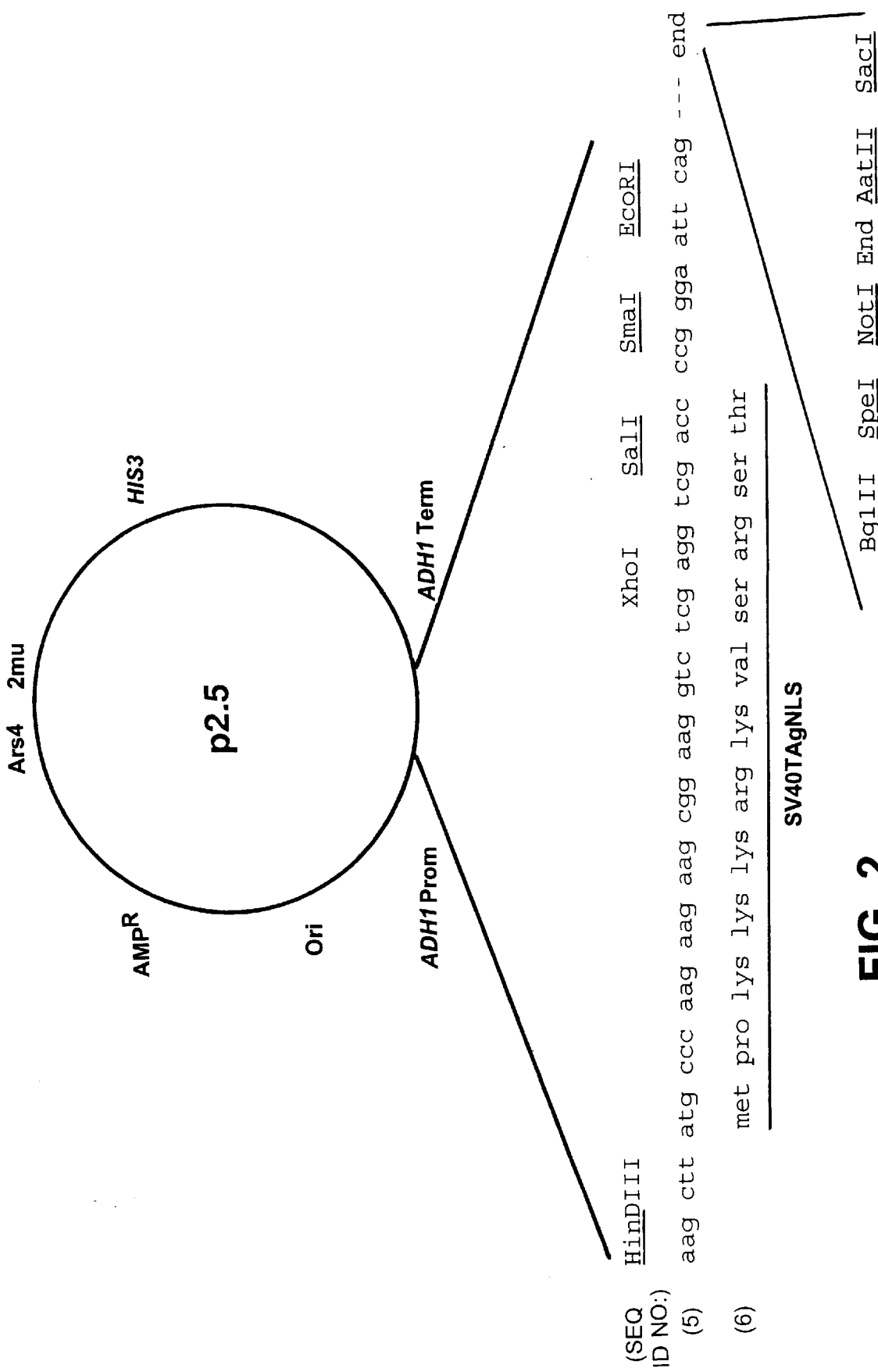
FIG. 2 is a map of the plasmid p2.5 A portion of the plasmid, containing a polylinker, is represented by SEQ ID NO: 5. The SV40 T antigen nuclear localization sequence is represented by SEQ ID NO: 6.

Construction of Plasmid p2.5: We have designed a novel plasmid, termed p2.5, which is useful for synthesizing dissociator compounds (e.g., proteins or RNA molecules) that can be tested in the invention (FIG. 2). More generally, this plasmid can be used to express preferred genes in yeast cells. This plasmid allows for the creation of cDNA libraries encoding dissociator compounds, and it offers the following features: (i) a 2 μm sequence which allows the plasmid to be maintained at high copy numbers; (ii) a selectable marker which, preferably, allows the plasmid to be selected for independently of the genetic constructs (i.e., plasmids) encoding the hybrid proteins or hybrid RNA molecules used in the invention; (iii) a yeast ADH1 promoter, which is a strong constitutive promoter; (iv) a GAL4 recognition site; (v) a nuclear localization signal located upstream of the polylinker, facilitating transport of the encoded polypeptide to the nucleus of the host cell; and (vi) a bacterial origin of replication. Plasmid p2.5 was generated by inserting the XhoI-XhoI fragment of pPC86, which contained the ADH1 promoter, into the XhoI site of pRS323, and subsequently the SalI-BamHI fragment of pPC86 containing the polylinker and the ADH1 terminator was inserted into the SalI-BamHI sites of the pRS323 (Sikorski et al., 1989, *Genetics* 122:19–27).

Construction of Plasmids for Producing Hybrid Proteins: Plasmids p97.CYH2 and pMV257 are useful in the invention for producing hybrid proteins having a GAL4-DB or AD, respectively, fused to a potential interacting molecule of interest (FIG. 10B). These plasmids are produced by inserting a sequence encoding CYH2 into pPC97 (for DB plasmids) or pPC86 (for AD plasmids) (FIG. 10A). Both p97.CYH2 and pMV257 have (i) a yeast ARS4 origin of replication; (ii) a yeast CEN6 centromeric sequence; (iii) a selectable marker (e.g., LEU2 for pPC97, and TRP1 for pPC86); (iv) a yeast ADH1 promoter and terminator; (v) a GAL4-DB (for pPC97) or a GAL4-AD (for pPC86); (vi) an SV40 large T antigen sequence encoding a nucleolar signal sequence positioned in frame with the DB or AD domain; (vii) a bacterial origin of replication; and (viii) a CYH2 counterselectable marker. Those skilled in the art recognize that numerous similar plasmids can be used to produce hybrid proteins. For example, hybrid proteins that include the DB or AD of VP16 (from Herpes Simplex Virus or Ace1 can be produced with plasmids having, in place of the GAL4-DB or -AD, sequences encoding the VP16 or Ace1 DB or Ace1 AD. Similarly selectable markers other than Leu2 and Trp1 can be used. These plasmids can be constructed with conventional molecular biology methods. Generally, in order to select for a yeast cell containing one of these plasmids, the yeast cell should not, in the absence of the plasmid, express a functional gene product which corresponds to the selectable marker. For example, a yeast cell into which p97.CYH2 is transformed should have a leu2 mutation; thus, a transformant containing p97.CYH2 can be selected on a medium which lacks leucine. The yeast strains MaV103 and MaV203 are particularly useful in conjunction with p97.CYH2 and pMV257.

Assay of Protein/Protein Interactions: The invention provides a convenient method for identifying protein/protein interactions. This method employs two populations of mating competent cells (e.g., yeast cells). Conventional cloning techniques can be used to operably link a selectable/ counterselectable reporter gene (e.g., a URA3 gene) to a promoter (e.g., a SPO13 promoter) which contains at least one recognition site for a DNA-binding-protein (e.g., a transcriptional factor such as GAL4). If desired, conventional methods can be used to integrate the selectable/counterselectable reporter gene into the genome of a yeast cell.

Assay of Protein/RNA Interactions: Conventional cloning methods can be used to express a variety of protein or RNA molecules in yeast cells. The RNA-binding moieties and the non-random RNA molecules to which they bind are unlimited. Generally, it is preferable that the RNA-binding moiety be composed of fewer than 50 amino acids. Preferably, the non-random RNA molecule is between 10 and 1,000 nucleotides in length; more preferably, the non-random RNA molecule is between 10 and 100 nucleotides in length. An example of a suitable RNA-binding moiety and the nonrandom RNA molecule to which it binds is the iron response element binding protein and the iron response element.

Assay of RNA/RNA Interactions: Numerous RNA/RNA interactions can be identified with the reverse two-hybrid system of the invention. Construction of appropriate expression plasmids for use in this aspect of the invention can be accomplished with commonly-known cloning methods. Non-random RNA molecules and RNA-binding moieties which are useful in identifying protein/RNA interactions are also useful for identifying RNA/RNA interactions.

Assay of DNA/Protein Interactions: The invention can also be used to characterize protein/DNA interactions. In this aspect of the invention, the DNA sequence of interest (the "test DNA sequence") is contained within a promoter which is operably linked to a counterselectable reporter gene. In this sense, the test DNA sequence serves as the DNA-binding-protein recognition site. The protein of interest (the "test protein") is examined for its ability to bind the test DNA sequence. In this aspect of the invention, the "test protein" is produced as a hybrid protein with a gene activating moiety, and binding of the hybrid protein to the test DNA sequence activates transcription of the counterselectable reporter gene. If desired, the test DNA sequence and/or the sequence of the test protein can be intentionally designed, randomly generated, or composed of both intentionally designed and randomly generated sequences. If desired, the test DNA sequence and/or the gene encoding the test protein can be derived from a nucleic acid library. Thus, a bidirectional combinatorial library can be created and screened in this aspect of the invention. The methods described herein for characterizing protein/protein interactions and for identifying compounds and mutations which affect protein/protein interactions can, with appropriate modifications, be used to characterize protein/DNA interactions.

Identification of Dissociator Compounds: Potential dissociator compounds can be introduced into cells by simply adding them to cultures. Many potential dissociator compounds are small enough that they will be taken up by a cell by endocytosis. Alternatively, if the dissociator compound is an RNA molecule or a protein, it can be produced in a cell by transforming the cell with a DNA construct expressing the desired RNA or protein. Dissociator compounds can be identified rapidly by first plating cells harboring a reconstituted transcription factor onto a solid medium under conditions such that the reconstituted transcription factor directs expression of a counterselectable reporter gene. This procedure creates a lawn of non-growing cells on the medium. The compounds to be tested are then deposited in an ordered fashion (e.g., to form a pattern, such as a grid) onto the lawn of non-growing cells. Compounds that are added in solution to the solid medium will diffuse slowly throughout the medium, creating a gradient in the concentration of the compound in the medium. Dissociator compounds can be identified by a growth of cells at the site at which the compound was deposited because dissociation of the transcription factor inhibits expression of the counterselectable reporter gene which prevents cell growth. Cells which grow in response to the addition of a dissociator compound will also form a gradient; the largest number of cells likely will grow at the position on the plate at which the dissociator compound was added. At the very center of a growing colony of cells, there may be a ring of non-growth due to toxicity of the compound at high concentrations. The diameter of the ring of growth will reflect the strength of the dissociator compound and reflect the concentration of compound required for dissociation.

Optimization of Sensitivity: Typically, before a dissociator is identified as such, its relative affinity for either partner of an interacting pair of molecules is unknown. Thus, the preferred conditions for identifying dissociators should permit recognition of even small decreases in the transcriptional activity of reporter genes. Conditions of maximum sensitivity can be established by minimizing the number of DNA-binding-protein recognition sites in the promoters of the reporter genes, and by using the lowest concentration of a drug (e.g., 5-FOA) sufficient to confer a drug-sensitive (e.g., Foa$^s$) phenotype on the host cell.

We describe below several examples of various aspects of the invention which provide guidance for practicing other embodiments of the invention.

Inducible Expression of a Reporter Gene: To demonstrate that expression of a reporter gene used in the invention can be induced with a transcription factor, we measured the ability of a reconstituted GAL4 protein to induce expression of a SPALX:URA3 allele. In this example, we employed the SPAL5:URA3 allele, which carries 5 GBSs. We analyzed the Ura and 5-FOA phenotypes conferred in the presence of (i) the full-length, wild-type GAL4 protein, or (ii) the GAL4-DB (amino acids 1–147) and the GAL4-AD (amino acids 768–881), expressed as two separate molecules in the same cell. Transformants that expressed the full-length GAL4 transcription factor exhibited strong, tightly regulated Ura$^+$ and Foa$^s$ phenotypes, while transformants which expressed GAL4-DB and GAL4-AD as two separate molecules exhibited strong and tightly regulated Ura$^-$ and Foa$^r$ phenotypes because the cells lacked a molecule capable of reconstituting the transcription factor. The strength of the Foa$^s$ phenotype was comparable to the phenotype exhibited by an untransformed wild-type control strain (FIG. 3). As was expected, none of the proteins (GAL4, GAL4-DB, or GAL4-AD) had any effect in cells containing a null allele of URA3 (ura3-52) (FIG. 3).

Use of Two Hybrid Molecules to Reconstitute a Transcription Factor: Here, we show that two hybrid molecules can be used to induce expression of a reporter gene. We demonstrate this with two different pairs of proteins; the proteins in each pair are known to interact. The first pair of proteins, cFos and cJun, interact with relatively high affinity. The second pair of proteins, pRb and E2F1, interact with relatively low affinity. We have used these two pairs of proteins and SPALX:URA3 alleles to demonstrate reconstitution of the GAL4 transcription factor. In these experiments, a total of four hybrid molecules were used. For the first pair of proteins, the interaction domain of cFos was covalently bonded (i.e., fused) to GAL4-DB, and the interaction domain of cJun was covalently bonded to GAL4-AD.

For the second pair of proteins, the interaction domain of pRb was fused to the GAL4-DB, and the interaction domain of E2F1 was fused to the GAL4-AD (FIG. 4).

DNA molecules encoding these fusion proteins each were constructed with a centromeric plasmid carrying an ADH1 promoter and a selectable marker. In this case, plasmids expressing the DBs carried the yeast LEU2 gene as a selectable marker; plasmids expressing the ADs carried the yeast TRP1 gene as a selectable marker. As negative controls, the GAL4-DB and GAL4-AD were expressed separately and without the interaction domains of cFos, cJun, pRb, or E2F1. To demonstrate that the Foas phenotype provides a sensitive measure of transcription, we compared the ability of the proteins to induce a Foa$^s$ phenotype with their ability to induce expression of β-galactosidase activity from a GAL4-inducible GAL1:lacZ reporter gene.

We found that the cFos and cJun interaction domains, and the interaction domains of pRb and E2F1 were able to reconstitute the GAL4 transcription factor in vivo. Cell cultures which expressed the DB-cFos hybrid and the AD-cJun hybrid also produced significant levels of β-galactosidase activity from GAL1:lacZ. Similarly, cell cultures which expressed the GAL4-DB-pRb hybrid and the GAL4-AD-E2F1 hybrid produced significant levels of β-galactosidase activity from GAL1:lacZ. To provide a quantitative assessment of the ability of DB-cFos and AD-cJun and of DB-E2F1 and AD-pRb to reconstitute a transcription factor, the β-galactosidase levels obtained by reconstituting GAL4 with these hybrid molecules was compared with the level obtained with an intact, full-length GAL4 protein (FIG. 5). Transcription of the GAL1:lacZ reporter gene induced by the intact GAL4 protein produced 3,000 β-galactosidase-specific units. The GAL4 protein reconstituted with DB-cFos and AD-cJun gave 100 β-galactosidase-specific units. Transcription induced by reconstitution of GAL4 with DB-pRb and AD-E2F1 produced only 0.5 β-galactosidase-specific units. These data indicate that the relatively strong interaction of cFos and cJun, and even the relatively weak interaction of pRb and E2F1, can be detected in the assay (FIG. 5).

Determination of the Limit of Growth Threshold: It is useful, though not necessary, to determine the "limit of growth threshold" in order to perform the counterselection methods under the ideal conditions for detecting compounds or mutations that may only weakly affect the interaction of two molecules. The limit of growth threshold is the minimum concentration of a drug (e.g., 5-FOA), in combination with the minimum number of GBSs, required to prevent growth of a cell. The higher the required concentration of the drug, the stronger the interaction between the two molecules responsible for reconstituting the transcription factor. The number of GBSs used in the invention can vary, if desired.

We defined the limit of growth threshold for three different pairs of interacting proteins which reconstitute the GAL4 transcription factor: (i) cFos/cJun, (ii) cJun/cJun, and (iii) pRb/E2F1. Control cells which lacked a GBS in the SPO13:URA3 promoter were not sensitive to 5-FOA, even in the presence of a GAL4 protein. Similarly, cells which expressed the GAL4-DB or GAL4-AD in the absence of a polypeptide which enabled them to associate (i.e., an interaction domain) also were resistant to 5-FOA, irrespective of the number of GBS. In contrast, cells in which GAL4 was reconstituted with cFos/cJun, cJun/cJun, or pRb/E2F1 displayed a 5-FOA sensitive phenotype.

In this example, the relative strengths of the interactions responsible for reconstituting the transcription factors are: cFos/cJun>cJun/cJun>pRb/E2F1. A gradient of 5-FOA sensitivity was observed on varying concentrations of 5-FOA in the context of increasing numbers of GBSs over a range of concentrations of 5-FOA for each interaction that was tested. These data indicate that the limit of growth threshold is 0.05% 5-FOA for cFos/cJun, 0.1% 5-FOA for pRb/E2F1, and 0.2% for cJun/cJun (FIG. 6).

Assay of Plasmid p2.5: To provide evidence of the operability of the plasmid p2.5, we confirmed that this plasmid does not erroneously affect transcription. We constructed derivatives of p2.5 which expressed pRb (p2.5pRB) without expressing an AD. When p2.5pRB was introduced into yeast cells that expressed intact GAL4, the plasmid did not affect the Ura or Foa phenotype of the host cell, indicating that the plasmid did not affect GAL4-dependent transcriptional function. This result indicates that pRb did not have a positive effect on expression of SPAL:URA3. This plasmid did produce significant quantities of pRb, as expression of this plasmid in cells conferred an Foa$^s$ phenotype on cells expressing DB-pRb and AD-E2F1 (FIG. 7). We have shown by Western blot analysis that the expression levels of the hybrid molecule was unchanged in cells harboring the p2.5pRB plasmids. These findings indicate that the p2.5 plasmids are useful for expressing potential dissociator compounds to be tested with the invention.

Construction of Yeast Strains Containing SPAL:URA3 Alleles: A SPO13:URA3 construct was obtained from plasmid pPL128 (from R. Strich and R. Esposito PUBLISHED????). This construct includes a fully functional SPO13 promoter and an ORF encoding a fusion protein having the first 15 amino acids of SPO13 fused to the full-length Ura3 protein, excluding the first methionine codon. Prior to insertion of the GAL4 binding sites (GBSs), the SPO13:URA3 fragment was excised from pPL128 with a SmaI-BamHI double digestion and cloned into a pBSK plasmid (Stratagene) which had been digested with ClaI, treated with Klenow, and subsequently digested with BamHI. The resulting plasmid, pMV252, contains within the SPO13 promoter, two EcoRI sites at nucleotides −170 and −368, and a unique HindIII site at −213. The GBSs were derived from plasmid GAL4–5/E1bCAT (Lillie et al., 1989, *Nature* 338:39–44). A fragment containing 5 GBSs was excised from this plasmid with a HindIII-XbaI double-digestion, and the fragment was subsequently blunt-ended with Klenow. The resulting fragment was cloned into pMV252 which had been digested with EcoRI and treated with Klenow. By sequence and PCR analysis, we identified two plasmids, pMV262–11 and pMV262-12, that contain 5 and 15 GBSs, respectively.

The SPAL:URA3 constructs were introduced into the yeast genome by integrative recombination at the ura3-52 locus by homologous recombination of the product of a polymerase chain reaction (i.e., by the gap repair method), generating the respective SPAL:URA3 alleles. The 5' primer was JB516 which contains 40 nucleotides of the URA3 sequence upstream of its promoter (−257 to −218) fused to 20 nucleotides of the SPO13 promoter (−370 to −351) (5'-GAAGGTTAATGTGGCTGTGGTTTCAGGGTC CATAAAGCTTGTCCTGGAAGTCTCATGGAG-3'; SEQ ID NO: 1) (Rose et al., 1984 *Gene* 29:113–124; Buckingham et al., 1990, *Proc. Natl. Acad. sci. USA* 87:9406–9410). The 3' primer was 3'URA3 (nucleotides +656 to +632 of URA3) (5'-TCAGGATCCCTAGGTTCCTTTGTTACTTCTTCCG-3'; SEQ ID NO: 2) (Rose et al., 1984 *Gene* 29:113–124). Standard PCR reaction conditions using pMV262-11 or pMV262-12 as templates generated either a product of the expected size (1,000 bp) or a mixture of products ranging from 1,000 to 1,300 bp, respectively.

The PCR products were transformed directly into the yeast strain MaV82, and transformants were selected on a medium which lacked uracil. The yeast strain MaV82 is MaV52 transformed with pCL1, a plasmid expressing GAL4 (Fields, et al., 1989, *Nature* 340:245–246). MaV52 (MATa ura3-52 leu2-3, 112 trp1-901 his3Δ200 ade2-101 gal4Δ gal80Δ GAL1:lacZ GAL1:HIS3@lys2 can1$^R$ cyh2$^R$) was obtained by 5-FOA selection (to eliminate GAL1:lacZ@URA3) and subsequent Can selection of Y153 (Boeke et al., 1984, *Mol. Gen. Gen.* 197:345–346; and Durfee et al., 1993, *Genes and Development* 7:555–569). A double homologous recombination event or a gene conversion event at the ura3-52 locus is expected using the 40 nucleotides in the 5' end of the PCR product, and the 320 nucleotides between the Ty insertion of ura3-52 and the 3' end of the PCR product (Rothstein, 1983, *Methods Enzymol.* 101:202–211; Baudin et al., 1993, *Nucleic Acids Research* 21:3329–3330; and Rose et al., 1984, *Mol. Gen. Genet.* 193:557–560).

Approximately 50% of the transformants exhibited the expected GAL4-dependent Ura$^+$ phenotype as tested by pCL1 plasmid loss. Integration of the SPAL:URA3 alleles was confirmed, and the number of GBSs was estimated in a PCR reaction using genomic DNA as a template. Of the different transformants, MaV99 contained 10 GBSs and is therefor SPAL10:URA3. The 5' primer was JB536 (nucleotides −298 to −276 of the URA3 sequence; 5'-GCGAGGCATATTTATGGTGAAGG-3'; SEQ ID NO: 3). The 3' primer was 13-5 (nucleotides −124 to −145 of the SPO13 antisense sequence; 5'-CATTTCCGTGCAAGGTACTAAC-3'; SEQ ID NO: 4) (Buckingham et al., 1990, *Proc. Natl. Acad. Sci. USA* 87:9406–9410). Strains MaV108 (MATa, lacks the GAL1:HIS3 fusion) and MaV103 (MATa, contains the GAL1:HIS3 fusion) and MaV203 (MATα, contains the GAL1:HIS3 fusion). MaV103 and MaV203 are meiotic segregants of a cross between MaV99 and PCY2 (Chevray et al., 1992, *Proc. Natl. Acad. Sci. USA* 89:5789–5793).

Plasmid Constructions: The cFos and cJun hybrid proteins (DB-cFos, AA 132–211 (pPC76); DB-Jun, AA 250–334 (pPC75); AD-cJun, AA 250–334 (pPC79)) have previously been described (Chevray et al., 1992, *Proc. Natl. Acad. Sci. USA* 89:5789–5793). Other proteins were generated by cloning PCR products so that they are in frame with the GAL4-DB (AA 1–147) or the GAL4-AD (AA 768–881) with plasmids pPC97 (for GAL4-DB) (pPC97 is pPC62 containing the pPC86 polylinker), or pPC86 (for GAL4-AD) (Chevray et al., 1992, *Proc. Natl. Acad. Sci. USA* 89:5789–5793). To produce proteins having wild-type sequences, the PCR products were also cloned into p97.CYH2. The CYH2 gene on this plasmid facilitates plasmid shuffling and removal of the plasmid from a cell. DB-pRb included AA 302–928 of pRb; DB-pRbΔ22 included AA 281–894 of a mutant pRb having a deletion of exon 22; DB-p107 included AA 372–1068 of p107; AD-E2F1 included AA 342–437 of E2F1; AD-E2F1Y411C included AA 342–437 of mutant E2F1 having a tyrosine to cysteine change at AA 411; and AD-E2F4 included AA 1–413 of E2F4 (Hiebert et al., 1992, *Genes & Development* 6:177–185; Whyte et al., 1988, *Nature* 334:124–129; Helin et al., 1993, *Mol. Cell. Biol.* 13:6501–6508; Sardet et al., 1995, *Proc. Natl. Acad. Sci*).

The p2.5 derivatives were generated by cloning PCR products into p2.5: E1A#2 included AA 30–132 of E1A; E1A#4 included AA 30–86 and 120–139 of E1A; E1A-CR1 included AA 1–120 of E1A; pRB included AA 302–928 of pRb; and E1A-CR2 included AA 76–139 of E1A. To isolate an AD-E2F1 hybrid which is capable of interacting with DB-DP1 without being toxic to the host cell, we screened a cDNA library in yeast cells expressing the DB-DP1 hybrid. Among other potential interacting molecules, we isolated an AD-E2F1 fusion which included AA 159–437 of E2F1.

Mutaaenesis Gap Repair Method: The polymerase chain reaction (PCR) mutagenesis gap repair method provides a convenient means for mutagenizing a chosen sequence (Muhlrad et al., 1992, *Yeast* 8:79–82). In this method, DNA encoding the sequence to be mutated is amplified in a PCR reaction under conditions which favor incorporation of incorrect nucleotides into the DNA molecule. Such conditions include relatively high manganese levels and/or a unequal mixture of the various nucleotides. The PCR primers which are used in this method generate linear PCR products which have at their ends sequences which are homologous to portions of a linearized expression plasmid. Yeast cells then are co-transformed with the linearized plasmid and the PCR products. At a high frequency, repair of the linearized plasmid in vivo results in the formation of stable circular plasmids containing the mutagenized sequence.

Compensatory Mutations: Compensatory mutations are mutations in pairs of interacting molecules (e.g., RNA molecules or proteins) which allow the mutated molecules to interact with each other but not with the corresponding wild-type proteins or RNA molecules. Examples of compensatory mutations include mutations which result in a reversal of charged residues that contact each other. For example, in two wild-type proteins (X and Y), a positively charged residue in the interacting molecule X contacts a negatively charged residue in interacting molecule Y. Compensatory mutations in X and Y may mutate X so that it contains a negatively charged residue, and mutate Y so that it contains a positively charged residue as a site of interaction. Compensatory mutations may also involve alterations in the sizes of interacting domains of the molecules. For example, if a portion of interacting partner X fits into a cavity of interacting molecule Y, compensatory mutations in X may render the interacting domain larger in size, and compensatory mutations in Y may render the interacting cavity larger in size to accommodate the larger interacting domain of X.

Knowledge of compensatory mutations in interacting molecules is of value to scientists because often these mutations are located at sites which are critical for interaction of two molecules. Compensatory mutations are thought to define key residues involved in molecular interactions, such as contact residues or amino acids or ribonucleotides which are responsible for proper folding of the interacting molecules. To date, in the instances where compensatory mutations have been identified in a protein and the protein's X-ray crystal structure is known, there has been a significant correlation between the interacting residues identified by the crystal structure and the interacting residues identified with compensatory mutations. The identification of residues which play such a vital role in the function of a molecule is critical for the rational design of therapeutic compounds which function by disrupting undesired (i.e., disease-related) interactions between proteins and/or RNA molecules.

Conditional Mutants: The study of the structure and function of proteins and RNA molecules is facilitated by the identification of conditional mutants of the molecules of interest. These conditional alleles allow wild-type function under permissive conditions, yet, when the cells are shifted to restrictive conditions, there is a detectable change in the ability of a molecule to function. The isolation of conditional alleles is complicated by the fact that they occur at relatively low frequency due to the fact that the resulting structural and/or functional alterations are often subtle. In many classical methods, the genes encoding interacting molecules are modified in vitro with methods directed to creating either large deletions or site-directed mutations. Such methods can be time-consuming. In addition, classical methods do not enable one to select alleles that are (i) functional under conditions that have been designated permissive and (ii) non-functional under conditions that have been designated restrictive.

IDENTIFICATION OF PROTEIN/PROTEIN INTERACTIONS WITH PROTEINS ENCODED WITHIN SYNTHETIC LIBRARIES

Construction of Yeast Strains Containing Synthetic Libraries: We have characterized the phenotype of the yeast strain MaV103, and tested the reverse two-hybrid system with this strain and with MaV203 and various hybrid proteins (FIG. 8). To demonstrate the operability of the reverse two-hybrid method of the invention, we used two synthetic libraries having a limited number of unknown parameters to carry out reconstruction (i.e., reconstitution) experiments designed to determine (i) whether it is possible to use the mass mating method to identify interactions at a frequency of $10^{-6}$ in a bidirectional library, and (ii) the efficiency of the counterselection method used to eliminate self-activating mating competent clones prior to formation of mated cells. The strategy used to create this "Bidirectional Combinatorial Library" (BCL) is outlined in FIG. 9.

Construction of Synthetic Libraries: For the library of clones having a polypeptide fused to a DNA binding moiety, the GAL4-DB, was used (FIG. 10). We used the GAL4-DB vector to create plasmids encoding 15 hybrid proteins which included various forms of pRb, p107, p130, p21, cyclin D2, cFos, cJun, DCC1, or dE2F (FIG. 11). To dilute the plasmids encoding the 15 hybrid proteins, we prepared a DNA mixture which contained 1 ng of each of the various plasmids and 1 µg of a plasmid which expressed the GAL4-DB alone (i.e., not as a hybrid protein with another polypeptide). Because each they contain an endogenous AD, both of the hybrid proteins encoded by DB-DCC1 and dE2F are sufficient to activate transcription of the reporter genes in the absence of any polypeptide fused to GAL4-AD. Both of the hybrids are sufficient to confer a 3AT resistant (in the absence of histidine) and 5-FOA sensitive phenotype to the MaV103 cells. In this assay, these hybrid proteins served as controls for the ability of the method to detect and eliminate these false positives.

The GAL4-AD vector was used to assemble a synthetic library of hybrid proteins having a polypeptide fused to an activation domain (FIG. 10). The 15 polypeptides used to create the library of hybrid proteins included various forms of cdk2, cJun, E2F-1, E2F-2, E2F-3, or E2F-4 (FIG. 11). The library of AD hybrid proteins did not include any self-activating clones (i.e., false positives). To dilute the plasmids encoding the various hybrid proteins, we prepared a DNA mixture which contained 1 ng of each of the various plasmids and 1 µg of a plasmid which expressed the GAL4-AD alone (i.e., not as a hybrid protein with another polypeptide).

The mixtures of plasmids encoding the AD and the DB molecules were separately transformed into yeast strains which contained identical sets of reporter genes. One synthetic library of plasmids was transformed into MaV203, a MATα strain. The other synthetic library of plasmids was transformed into MaV103, a MATa strain. Which library is transformed into cells of which mating type does not matter, provided that yeast of two compatible mating types are used for the two libraries. The transformed yeast cells were plated onto an agar medium lacking either leucine or tryptophan, using either the LEU2 or the TRP1 marker, respectively, to select for transformants. MATa Leu$^+$ transformants were haploid clones obtained with the library of polypeptides fused to the GAL4-DB, and MATα Trp$^+$ transformants were haploid clones obtained with the library of polypeptides fused to the GAL4-AD.

Counterselection: Counterselection was used to eliminate the mating competent clones which could independently activate transcription. The Leu$^+$ and Trp$^+$ colonies obtained in the first selection step were directly replica-plated, separately, to a medium which included 0.2% 5-FOA (FIG. 12). On this medium, only the colonies corresponding to the non-activator clones grew further. If desired, the counterselection step can be repeated, and in this case, the step was performed twice. As is shown in FIG. 12, all of the clones which improperly activated transcription were completely eliminated by counterselection on 5-FOA (the large patches of cells on the right side of the plates represent controls used in the experiment; compare the number of colonies recovered in the absence of 5-FOA counterselection (bottom left panel) with the number obtained with 5-FOA counterselection (bottom right panel). After two rounds of 5-FOA counterselection, no self-activating clones were detected on a medium lacking histidine and containing 3AT.

Mass Mating Method: Cells which survived the counterselection step, indicating that they contained the non-activator clones, were harvested and resuspended in liquid media. Approximately $10^{10}$ cells from each of the two strains of cells were resuspended, separately, in 10 mL of media, giving a concentration of $10^9$ cells/mL. The two cell suspensions were subsequently mixed together and incubated overnight under conditions that favor formation of mated cells (i.e., mating). In this case, the mixture of mating competent cells was spread onto a 15 cm plate containing YEPD, a rich medium, and the resulting mated cells were re-plated on a medium which lacked both leucine and tryptophan. Our data indicate that the efficiency of mating was approximately 10%. Based on these data, we conclude that, if the volume of the suspensions is increased up to a few liters, up to $10^{13}$ mated cells can be selected with the mass mating method. These data suggest that by scaling up the reaction to a volume of a few liters, as many as $10^{13}$ pairs of interacting proteins can be generated and screened.

Selection: The mated cells which result from the mass mating method were plated onto a solid medium that selects for the presence of the plasmids encoding the AD and the DB. Here, a medium lacking both leucine and tryptophan was used. The colonies which grew on these plates were replica-plated onto a medium which lacked leucine, tryptophan, and histidine, and which contained 20 mM 3AT.

For a negative control, we induced formation of diploid cells from haploid cells that had been transformed exclusively with plasmids encoding GAL4-DB or GAL4-AD without being fused to another polypeptide. Of 5×10$^5$ diploid cells generated from the negative control, none of the diploids was able to survive on a medium that lacked both leucine and tryptophan, indicating that no false positives were obtained.

For a positive control, we constructed two synthetic libraries of cells expressing either DB-cFos or AD-cJun hybrid proteins. These libraries were diluted 1:100, and diploid cells were formed and selected on plates lacking leucine, tryptophan, and histidine. Under these conditions, surviving cells were obtained at the expected frequency of approximately $10^{-4}$ (twelve 3AT-resistant colonies were obtained from approximately 50,000 diploids).

In contrast, cells containing the synthetic libraries give rise to positive growing colonies on medium containing 3AT using this procedure. Among, $5 \times 10^6$ diploid tested, we recovered 400 3AT-resistant colonies. The diploid cells in this example were plated onto a medium lacking leucine and tryptophan and then plated onto a medium lacking leucine, histidine, and tryptophan, and containing 3AT. If desired, the mated cells can be plated directly onto a medium containing 3AT and lacking leucine, histidine, and tryptophan.

The 400 colonies that were recovered were tested for their sensitivity to 5-FOA as a measure of the expression of the URA3 gene. They also were tested for β-galactosidase activity on a medium containing X-gal. Approximately 95% of the clones that were tested expressed the URA3 and lacZ genes. Of these colonies, 120 were analyzed further. Plasmids were extracted from these colonies and amplified in, and then extracted from, $E.$ $coli$. We identified by sequence analysis the inserts in plasmids encoding 80 pairs of interacting proteins. The data obtained from the sequence analysis (FIG. 13) indicate that (i) most of the expected interactions were detected with the method; and (ii) the cFos/cJun interaction is reconstituted at a high frequency, possibly due to the relatively small sizes of the DNA encoding these polypeptides. Accordingly, the invention provides a convenient and efficient method for identifying protein-protein interactions.

IDENTIFICATION OF COMPOUNDS WHICH DISRUPT MOLECULAR INTERACTIONS

Dissociation of a Reconstituted Transcription Factor: We have tested the ability of the invention to detect inhibition of transcription of a reporter gene where inhibition is caused by a compound which disrupts (i.e., prevents or causes dissociation of) the interaction of two molecules. This method can be used to identify compounds (i.e., dissociators) which disrupt the ability of two hybrid molecules to interact and mediate transcription. Effective compounds cause a decrease in expression of the reporter gene (e.g., SPALX:URA3). For example, where the reporter gene is URA3, dissociator compounds confer a $Foa^r$ phenotype on the host cell. Thus, the invention provides a convenient means for identifying molecules which disrupt a protein/protein interaction.

We have found that transcription can be blocked in this system by overexpressing in a cell either one of the two interacting proteins which lacks a DB or an AD. The overexpressed interacting protein, which lacks a DB or AD, can compete with the two hybrid molecules and prevent activation of transcription of the reporter gene. These data provide evidence that dissociator compounds can be produced in the cell and be identified with the invention.

As another example of the ability of the invention to detect dissociation of two interacting molecules, we overexpressed a third protein, E1A, in cells which expressed either AD-E2F and DB-pRb, or AD-E2F and DB-p107 hybrid molecules. We measured the ability of adenovirus E1A protein to bind to pRb and p107 and cause dissociation of pRb/E2F and p107/E2F4. In these studies, E1A was expressed in yeast cells expressing AD-E2F and either DB-pRb or DB-p107 by employing conventional cloning methods to insert the E1A coding sequence into the polylinker of the plasmid p2.5. We found that expression of E1A in the yeast strains rescued the $Foa^s$ phenotype (FIG. 14), indicating that the invention can detect dissociation of both DB-pRb/AD-E2F and DB-p107/AD-E2F interactions.

Several observations suggest that dissociation mediated by E1A is specific: (i) overexpression of E1A did not affect the steady-state levels of the various hybrid proteins; (ii) E1A protein expression had no effect on the $Foa^s$ phenotype resulting from DB-DP1/AD-E2F interactions; (iii) conserved region II (CR2), known to be essential for pRb/E2F dissociation in mammalian cells, was required for the $Foa^s$ phenotype; and (iv) overexpression of pRb in the absence of any DB sequences rescued, to the same extent as E1A, the $Foa^s$ phenotype in cells expressing DB-pRb/AD-E2F1, but not the $Foa^s$ phenotype of DB-p107/AD-E2F4 (FIG. 14).

Increasing the Strength of a Dissociator Compound: If desired, the strength of a dissociator compound can be characterized by examining the ability of the compound to dissociate two interacting hybrid molecules (e.g., proteins) over a range of drug (e.g., 5-FOA) concentrations that cause lethality. For example, the first round of analysis can be performed with a relatively low 5-FOA concentration (i.e., a concentration which is close to the growth threshold) and with a low number of GBSs in order to identify relatively weak dissociator compounds. In the second round of analysis, the 5-FOA concentration and/or the number of GBSs is increased, and more potent dissociators are identified. The analysis can be repeated. This method is also useful in the design of dissociator compounds. Weak dissociator compounds, once identified, can be modified (e.g., by amino acid, nucleotide, or chemical group substitution accomplished with standard techniques) and then tested in subsequent rounds of analysis. Dissociator compounds that have been rendered more potent by the modification can be identified by their ability to promote cell growth (i.e., inhibit the interaction) under more stringent conditions (e.g., a higher concentration of 5-FOA) than could the parental molecule.

Use of a Diploid Yeast Strain to Identify Dissociator Compounds: If desired, diploid strains of yeast carrying two copies of a reporter gene can be used to identify dissociator compounds. For example, the use of diploid strains carrying two copies of SPALX:URA3 can reduce the probability that the appearance of an $Foa^r$ clone is due to a spontaneous reversion of the $Foa^s$ phenotype. Accordingly, the use of diploid strains increases the sensitivity of the method. While dissociator compounds can be identified in haploids or diploids, the use of diploids is preferred.

We have found that mutations responsible for reversion of the $Foa^s$ phenotype represented cis-acting mutations linked to the SPAL:URA3 reporter genes. Theoretically, both cis- and trans-acting mutations can lead to reversion of the $Foa^s$ phenotype. Cis-acting mutations are likely to involve deletion of the repeated GBSs in the promoters of the SPAL-X:URA3 allele, or mutation of the URA3 ORF itself, while trans-acting mutations are likely to represent gene conversion events between plasmid sequences, or knockout mutations in the coding sequences of the interacting molecules.

To characterize the nature of spontaneous mutations leading to reversion of the $Foa^s$ phenotype, we assayed whether expression of two reporter genes (GAL1:HIS3 and GAL1:lacZ) was altered in the $Foa^r$ colonies (i.e., spontaneous mutants). Our data indicate that expression of HIS3 and lacZ was not affected in these cells, suggesting that the reversions represented cis-acting mutations linked to the SPALX:URA3 promoter. Accordingly, diploid strains of yeast, containing two copies of the SPALX:URA3 reporter genes will decrease the frequency with which spontaneous revertants appear. The frequency is calculated to be $10^{-6} \times 10^{-6} = 10^{-12}$. The frequency of spontaneous reversion can also be determined experimentally by comparing the ratio of Foa$^r$ colonies arising from haploid cells expressing the cFos/cJun hybrid proteins with that of diploid cells.

USE OF MUTAGENESIS TO CHARACTERIZE
MOLECULAR INTERACTIONS

Identification of Mutant Interactina Molecules: We have also tested the ability of the invention to detect physiologically relevant mutations which abrogate interactions. An important precept of the invention is that a mutation which dissociates the interacting molecules should be able to reduce, to a detectable extent, expression of the reporter gene to which the DNA-binding-protein recognition site is operably linked. For example, a mutation in the retinoblastoma protein of a pRb/E2F1 interacting pair should result in a Foa$^r$ phenotype in cells, provided that the mutation involves a residue which participates in the interaction of the two molecules. To test the ability of the invention to detect decreases in transcription of the reporter gene, we utilized a pRb allele that, due to a deletion of exon 22, fails to associate with E2F1. We expressed this form of pRb as a hybrid protein with the GAL4-DB and termed the hybrid protein DB-pRbΔ22. E2F1 was expressed as a hybrid protein with GAL4-AD. We found that expression of these proteins in yeast resulted in a Foa$^r$ phenotype even though the level of expression of DB-pRbΔ22 was comparable to the level of expression of the wild-type pRb (FIG. 15). We also performed the reciprocal experiment, which involves a hybrid protein having a mutated allele of E2F1 (AD-E2FY411C) which fails to bind pRb. Expression of this mutant allele also resulted in a Foa$^r$ phenotype (FIG. 15). These data provide further evidence that the reverse two-hybrid system of invention can be used to detect mutations which prevent two molecules from associating.

Use of a Two-Step Selection Method to Identify Subtle Mutations Which Define Structurally and Functionally Significant Residues: We have used a two-step selection method to identify residues in E2F1 which mediate its ability to interact with DP1. This method relies upon the strategy outlined in FIG. 16. We first identified mutations which affect the ability of DP1 and E2F1 to bind to each other, and, in a second step, identified those which do not completely abrogate interaction between the proteins. This strategy was based on the premise that mutations which completely destroy the ability of E2F1 to interact with DP1 may represent uninformative mutations, such as those which alter the size of the protein (e.g., non sense mutations, deletions, or insertions). This method facilitates the identification of alleles (e.g., alleles selected from a library of alleles) which mildly affect the protein/protein interaction.

In this example of the two-step selection method, we used a GAL1:HIS3 reporter gene (Durfee et al., 1993, Genes & Dev. 7:555–569). This reporter gene is particularly well-suited for this method because the His phenotype is titratable, i.e., the His phenotype can be measured over a range of concentrations of 3AT, a specific inhibitor of HIS3 enzymatic activity (FIG. 17). Cells in which GAL1:HIS3 is expressed grow on a medium lacking histidine and containing high concentrations of 3AT. In the present case, expression of DB-DP1/AD-E2F1 allowed the cells to grow on a medium containing up to 100 mM 3AT (FIG. 17). In this two-step selection method, the first selection was performed with 0.1% 5-FOA, and the second selection was performed with 10 mM 3AT (on a medium lacking histidine).

In these experiments, a plasmid encoding the DB-DP1 hybrid protein was transformed into the yeast strain MaV103 which contains a SPAL10:URA3 allele. Transformants were selected on a medium which lacked leucine. The E2F1 sequence was amplified by PCR, with a plasmid encoding AD-E2F1 (AA 159-437 of E2F1) serving as a template. The 5' primer which was used corresponded to a sequence located in the coding sequence for AD. The sequence of the primer was located approximately 100 bp upstream of the junction of AD and the first amino acid (AA 159) of E2F1. The 3' primer that was used corresponded to the sequence immediately adjacent to the stop codon of the E2F1 ORF. Using these primers and this E2F1 template, several PCR amplifications reactions were performed over a range of conditions that are conducive to mutagenesis of the amplified sequence. In these several reactions, the concentration of manganese and/or the relative concentrations of nucleotides varied according to conventional methods for using PCR to introduce mutations in a sequence. While the optimal conditions for mutagenesis depend on the length and sequence of the fragment being amplified, suitable conditions give a mutagenesis frequency which is high enough so that mutants can be detected among a number of yeast colonies that can be practically screened on a single petri plate, and yet the frequency is low enough to avoid multiple mutations in the amplified sequence.

Gap Repair Method: The gap repair method was used to incorporate the mutagenized sequences into a plasmid. (FIGS. 18A and 18B). In this case, the AD-E2F1 plasmid was linearized by digestion at a unique BglII site located in the middle of the E2F1 sequence. As an alternative, an "empty" AD plasmid that is linearized in its polylinker can be used, provided that the PCR primers for amplification of E2F1 correspond to plasmid sequences and sequences in the PCR fragment.

For gap repair, 100 ng of the amplified PCR fragment and 100 ng of the linearized plasmid were co-transformed by the lithium acetate method into yeast cells which expressed DB-DP1. In this example, the transformants were selected on a growth medium which lacked leucine and tryptophan. After two days of growth on a rich growth medium, the first step of selection was performed by replica-plating the transformants onto a medium which lacked leucine and tryptophan and which included 0.1% 5-FOA (Sc-L-T+5FOA medium) (FIG. 19). We detected a correlation between the number of colonies on the plate and the concentration of manganese and the composition of the nucleotides (i.e., the extent of mutagenesis). Colonies which grew on a medium which included 5-FOA and which lacked leucine and tryptophan were replica-plated onto plates lacking leucine and tryptophan in order to allow recovery (FIG. 19).

For the second step in the selection, the colonies on these plates were replica-plated onto plates which lacked leucine, tryptophan, and histidine, and which contained low concentrations of 3AT. Colonies which grew on these plates were expected to contain a mutation in E2F1 which weakly affected the ability of E2F1 to interact with DP-1 (FIG. 19). Data which are representative of the data obtained with the two-step selection method are provided in the Table 1.

TABLE 1

|  | Number of Transformants | Number of 5-Foa$^R$ | Number of 3AT$^R$ |
| --- | --- | --- | --- |
| na DNA | 0 | nt | nt |
| AD-E2F1 circular | 10,000 | 2–3 | 0 |
| AD empty (pPC86) | 10,000 | 10,000 | 0 |
| PCR fragment alone | 0 | nt | nt |

TABLE 1-continued

|  | Number of Transformants | Number of 5-Foa$^R$ | Number of 3AT$^R$ |
| --- | --- | --- | --- |
| Linearized plasmid alone | 500 | 50 | 0 |
| PCR + plasmid | 10,000 | 500 | 20–30 |

To confirm the phenotype of the colonies which grew in the second step of the selection process, the colonies were first purified by picking them and streaking them for single colonies on Sc-L-T plates. Four purified colonies were then patched onto Sc-L-T plates, then replicated onto a medium lacking histidine and containing 0.1% 5-FOA, 10 mM 3AT, and X-gal. Only the colonies were still able to grow under these conditions were analyzed further. Approximately 90% of the initially selected colonies passed this additional test. DNA extracted from these cells was used to transform *E. coli* cells, and transformed cells were selected on a medium that included ampicillin. The resulting colonies contained plasmids encoding either DB-DP1 or AD-E2F1 hybrid proteins. Plasmids encoding AD-E2F1 were identified by restriction digest analysis of DNA obtained from the transformed *E. coli* cells.

Plasmids encoding AD-E2F1 were re-introduced into yeast cells containing the GAL1:HIS3 and SPAL10:URA3 alleles and which expressed DB-DP1. Transformed cells were selected on Sc-L-T media. Four transformants were patched onto a Sc-L-T medium then replica-plated onto a medium lacking leucine, tryptophan, and histidine, and containing 0.1% 5-FOA, 10 mM 3AT, and X-gal (FIG. 20). As a positive control, the wild-type DB-E2F1 allele was reintroduced into the cells containing the GAL1:HIS3 and SPAL10:URA3 alleles (FIG. 20, bottom row), and pPC86, an empty AD plasmid (i.e., a plasmid lacking E2F1), served as a negative control.

The AD-E2F1-34 allele provides an example of a plasmid which does not retest the phenotypes expected of a mutant allele. In other words, the growth and β-gal phenotypes of AD-E2F1-34 were indistinguishable from wild-type AD-E2F1. The hypothesis that AD-E2F1-34 was identical to the wild-type allele was confirmed by sequence analysis of AD-E2F1-34 which did not reveal any mutations in the sequence AD-E2F1-34. Although some wild-type alleles were recovered in the shuttling process to *E. coli*, approximately 90% of the recovered alleles were mutants, as is desired.

We sequenced 12 AD-E2F1 alleles, and in 11 of these 12 alleles, we detected a single nucleotide change in the 1.2 kb of sequence encoding E2F1. In six of the alleles, the mutation mapped to a domain that is termed the Marked Box 2 (MB2) domain (FIG. 21). The MB2 domain is represented by a stretch of 18 amino acids. The fact that the mutations are clustered within this 18 amino acid region suggests that the MB2 domain is required for binding of E2F1 to DP1. Further support for the suggested role of the MB2 domain comes from the observation that, between the five human E2F proteins, there is a high degree of homology in this region of the proteins (FIG. 21, top).

Additional support for the value of the two-step selection method comes from the observation that there is a correlation between (i) the various mutations that were produced and identified with this method and (ii) the various phenotypes that were detected (FIG. 20). For example, the E2F1-31 allele, which strongly affected the interaction between E2F1 and DP1 (i.e., cells expressing this allele exhibited a high level of resistance to 5-FOA (FIG. 20)), was associated with a small in-frame deletion of the MB2 domain (FIG. 21). In contrast, the allele containing two mutations, E2F1-30, affected the interaction relatively mildly; cells containing this allele grew poorly on 5-FOA. Although two mutations were found in this allele, both mutations were at positions in the MB2 domains which are not completely conserved between different members of the E2F family (FIG. 21, top and bottom), suggesting that these residues are less critical for the interaction. In accordance with these data is the fact that the alleles which had conservative mutations affected the interaction and the growth phenotype to an intermediate extent. In these alleles (E2F1-20, -32, and -65), the mutations replaced the isoleucine at amino acid 284 with either threonine or asparagine. If desired, these mutant alleles can be reintroduced into yeast cells in order to examine the function of the mutant gene products further.

Isolation of Relatively Strong Mutations by a Two-Step Selection Method: We have isolated and sequenced eight alleles of E2F1 which lacked the ability to interact with DP1 in the first step of the two-step selection procedure (FIG. 19). Sequence analysis of each of those alleles revealed a nonsense mutation, deletion, or insertion which would result in truncation of the E2F1 protein. To avoid selection of truncated mutants, we used a variation of the two-step selection method to identify mutant alleles of E2F1 which are defective in their ability to bind to DP1, but which retain their ability to interact with pRb. The rationale underlying this approach is that, because the pRb binding site is located at the C-terminal domain of the E2F1 allele (the binding site is composed of amino acids 409–427 of amino acids 159–437 of E2F1), mutations which abrogate binding of E2F1 to DP1 without truncating the protein (i.e., affecting binding to pRb) can easily be identified (FIG. 22). We have constructed a plasmid which expresses a DB-pRb hybrid protein (amino acids 302-928 of pRb were used).

For the first step of the selection method, cells are grown on a Sc-L-T medium for two days, then replica-plated onto a Sc-L-T+5-FOA (0.1%) medium (as in FIG. 19). The plasmid expressing DB-DP1 can be eliminated by growing the cells on non-selective media, and cells that have lost the DB-DP1 plasmid while keeping the AD-E2F1 plasmid can be identified by assaying for their ability to grow on the appropriate selective media after replica plating. An alternative method for identifying colonies that have lost the DB-DP1 plasmid is to express a counterselectable marker on the DB-DP1 plasmid and to grow the cells on a medium where expression of the counterselectable marker is lethal (plasmid shuffling). For example, the plasmid encoding DB-DP1 can be engineered to express a CYH2 gene, and cells expressing DB-DP1 can be eliminated on a medium containing cycloheximide. In the second step of the selection, cells containing AD-E2F1 are mated with cells which form a lawn on agar plates and which contain the DB-pRb plasmid, and expression of the selectable reporter gene is measured. The resulting mated cells are then tested on a medium lacking histidine, leucine, and tryptophan and containing 10 mM 3AT. The positive clones in this assay are representative of mutated, but not truncated, E2F1 alleles. Among 350 Foa$^r$ colonies tested, 12 colonies scored positive after mating with cells containing pRb.

In alternative embodiments of this method, a protein other than E2F1 can be fused to the AD with conventional methods. If desired, the protein to be mutagenized can be fused to the DB instead of the AD. The transcription factor which is reconstituted in this method can be one other than GAL4 (e.g., LexA or Ace1 can be used). In addition, reporter genes other than URA3 and HIS3 can be used, provided that combination of reporter genes allows for counterselection in the first step and positive selection (preferably with a titratable phenotype) in the second step.

Functional C-term Tag: To ensure that the mutant proteins characterized in this two-step selection method do not simply represent truncations of the wild-type protein, a functional C-term tag can be covalently bonded to the C-terminal end of any protein which can be expressed in the above clone. Such a functional C-term tag would function like the pRb binding domain in the above-disclosed example. A functional C-term tag is a stretch of amino acids which includes a binding domain for a protein. The pRb binding domain is particularly useful because, at 18 amino acids in length, it is unlikely to dramatically alter the structure of the protein being characterized. To assay for the presence of the carboxyl terminus of the mutated protein, a protein which specifically binds the functional C-term tag is introduced into the cell as a hybrid protein with a DB (or an AD if the mutated protein is fused to the DB). One can then assay the ability of the hybrid protein expressed from the plasmid and the mutated protein present as a hybrid to reconstitute a transcription factor. Positive selection on an appropriate medium can be used to select for cells which retain the full-length protein.

An alternative, but similar, method for identifying strong mutations in the two-step selection method involves constructing a tribrid protein consisting of GAL4-AD-E2F1-GFP (green fluorescent protein) (Chalfie et al., 1994, Science 263:802–805). In this method, the green fluorescent protein serves as a functional C-term tag, and alleles of the resulting fusion protein, AD-E2F1-Green, can be assayed for their ability to interact with DB-DP1. Cells express green fluorescent protein and in which hybrid proteins interact can be identified by their 3AT-resistant, Foa-resistant, β-gal positive phenotype. In addition, cells expressing the green fluorescent protein fluoresce under UV light. Thus, the green fluorescent protein can be used in the selection of mutant alleles. In the selection of strong and weak mutations, expression of normal levels of the full-length interacting protein (e.g., E2F1) can be confirmed by western blot analysis of cell extracts.

To determine whether the newly isolated alleles exhibit similar phenotypes, protein binding assays can be used. For example, each E2F allele can be tested in an in vitro binding assay that involves amplifying, in a PCR reaction, the sequences encoding the various E2F alleles. An example of an appropriate 5' primer is one which has 25 nucleotides corresponding the phage T7 RNA polymerase promoter sequence and 20 nucleotides that correspond to the activation domain near the junction of the activation domain and amino acid 159 of E2F1 (i.e., the first E2F1 amino acid). A suitable 3' primer is one which corresponds to the 3' end of the E2F1 sequence. The PCR products from amplification of this sequence can be used in an in vitro transcription/translation system to generate the corresponding proteins. The mutant proteins can be bound to hybrid proteins having wild-type DP1 bound to glutathione-S-transferase. Interacting pairs of proteins can be purified with glutathione agarose beads, released from the beads, and analyzed by SDS-polyacrylamide gel electrophoresis.

Identification of Compensatory Mutations: Additional information about the mutations identified in the two-step selection method can be gained by creating and identifying mutations in the wild type partner (DP-1 in the example) that restore interaction of the two proteins (here, E2F1 and DP-1). For example, in this method, the sequence of DP-1 which encodes the E2F1-binding domain is amplified and mutagenized by PCR. In accordance with the gap repair method, the PCR products are then co-transformed into yeast cells containing specific AD-E2F1 mutant plasmids along with the DB-DP-1 plasmid linearized in the corresponding region. The transformants then are replica-plated onto a medium containing 3AT and lacking histidine, and the surviving colonies are analyzed further. Each allele can be amplified in E. coli, sequenced, and re-introduced into yeast to retest its phenotype to ensure that the pairs of mutants interact. By carrying out this process for a number of alleles having a variety of mutations, a genetic map representing the protein/protein interactions can be constructed.

Isolation of a Relatively Large Set of Pairs of Compensatory Mutations by "Bivalent Genetics": The two-step selection methods and the scheme leading to the construction of bidirectional combinatorial libraries suggest the feasibility of a genetic method referred to here as "bivalent genetics," by which it is possible to select for large numbers of pairs of compensatory mutations in genes encoding interacting molecules. In two independent experiments, performed in yeast strains of different mating type, libraries of mutations affecting an interaction are furst generated according to the "two-step selection" procedure. In a second step, these two libraries of mutant alleles are challenged with each other by mass mating, and compensatory mutations (where the interaction is restored) are selected in a set of steps similar to the ones involved in the construction of combinatorial libraries. In particular, by "bivalent genetics" is meant a method by which relatively large sets of pairs of compensatory mutations may be recovered, and, by "two-step selection" is meant a method by which informative mutations that affect molecular interactions in a defined manner may be recovered.

Isolation of Conditional Alleles: The invention also facilitates the production and identification of conditional alleles of interacting molecules. Because the invention provides a convenient method for screening a large number of mutant alleles (approximately $10^{10}$), the invention facilitates the detection of relatively rare conditional alleles. In this method, termed Conditional Alleles in a Two-Step Selection (CATS), one of the two interacting molecules is mutagenized in order to isolate conditional mutant alleles that interact with the other, wild-type, allele under certain conditions (i.e., permissive conditions) but not under other conditions (i.e., restrictive conditions). Any of numerous conditions, selected by the practitioner, can be used as the permissive or restrictive conditions. Commonly, a difference in temperature characterizes the distinction between permissive and restrictive conditions, although the invention is not limited to the use of alterations in temperature. For example, the presence of absence of a drug can define the difference between a permissive and a restrictive condition.

The CATS method relies upon the use of counterselection with a selectable/counterselectable reporter gene and the method resembles the more general two-step selection method described above. A schematic representation of the strategy used for CATS is provided in FIG. 23B. In this method, the desired interacting molecules are fused, separately, to the DB and AD of a transcription factor, and the employed yeast strain contains a selectable/counterselectable reporter gene (e.g., a URA3 gene). PCR mutagenesis methods (as described above) are used to mutate one of the interacting partners, and the PCR products are introduced into the cell with conventional methods for gap repair. Selectable markers on the plasmids expressing the AD and the DB can be used to select for repair of the gap and for maintenance of the plasmid encoding the wild-type interacting molecule.

The resulting transformants then are replica-plated onto a medium containing a drug (e.g., 5-FOA) which inhibits the growth of cells expressing the counterselectable reporter gene, and the transformants then are incubated under restrictive conditions. Of the various transformants, only the cells which contain mutant alleles affecting the interaction of the molecules of interest will be selected for in this first (negative) selection step.

The second selection step selects for mutant alleles which are functional under permissive conditions. The cells which survived the first step are transferred (e.g., by replica-plating) to a medium which positively selects for cells expressing the selectable/counterselectable gene; these cells are incubated under permissive conditions. Cells containing a conditional allele(s) of one of the interacting molecules will grow.

The mutant alleles can then be recovered and characterized by extracting the plasmid DNA and amplifying it in bacteria, then characterizing the DNA and the encoded protein with conventional methods. The conditional alleles identified with the invention affect the ability of two molecules to interact, and thus these conditional alleles point to residues or nucleotides that are critical for interaction. As was described above, the identification of the interaction domain of a molecule is critical for the rational design of therapeutics and for a detailed understanding of biological processes.

We have used CATS to isolate a conditional allele of cJun which interacts with cFos at 36° C. but not at 30° C. (FIG. 24). These data indicate that at 36° C. in, cFos and the mutant cJun reconstitute the GAL4 transcription factor, leading to expression of URA3 and resulting in lethality when the cells are grown on 5-FOA. In contrast, when the cells expressing the conditional allele are grown at the restrictive temperature, the interaction is prevented and the cells survive growth on 5-FOA. Thus, these data indicate that the invention provides a convenient method for isolating and identifying conditional alleles of molecules which can be further characterized with conventional techniques.

Other Embodiments

The interaction of numerous types of RNA molecules, DNA molecules, or proteins can be measured in the invention. For example, interactions which can be assayed in the invention include interactions between antibodies and antigens, receptors and ligands, a restriction enzyme and the DNA site it cleaves, and viral proteins and host proteins. For example, the invention allows for the identification of protein/protein interactions which occur in the HIV provirus. In this method, HIV proteins are separately expressed in the form of AD and DB hybrid proteins, and the ability of the HIV proteins to reconstitute the intact transcription factors is assayed. Thus, the invention provides a convenient method for identifying all of the protein/protein interactions encoded within an entire genome. The identification of HIV protein/protein interactions facilitates the discovery of compounds which exert a therapeutic activity by disrupting protein/protein interactions. In a similar method, the invention can be used to identify interactions between HIV proteins and proteins of activated human T-cells.

The invention can also be used to isolate and characterize monoclonal antibodies. In this method, an antigen/antibody binding reaction is used to reconstitute a transcription factor. In this method, an antigen and a DNA-binding moiety (e.g., the DB of GAL4) are expressed as a hybrid protein; the immunoglobulin heavy chain and a gene activating moiety (e.g., the AD of GAL4) are produced as a hybrid protein; and an immunoglobulin light chain is expressed as a fusion protein with a nuclear localization sequence (FIG. 25). The ability of the antibody to bind to the antigen can be assayed by detecting expression of the reporter gene(s). In view of the combinatorial nature of the immune system, and the somatic refinement capabilities of the immune system, the invention, which is combinatorial in nature and capable of refinement, is particularly well-suited for identifying antibody/antigen interactions.

If desired, plasmids encoding self-activating hybrid proteins can be eliminated from cells by using DB and AD vectors which contain "shuffling" counterselectable markers. These genes allow for selection of cells that have lost either the DB or AD plasmid with integration of the gene encoding the hybrid protein. For shuffling, expression of the counterselectable reporter gene can be tested under conditions which select against the DB or AD plasmid, and clones that score positive in this assay are eliminated from further steps in the analysis. The plasmids used to express the proteins and RNA molecules employed in the invention can employ selectable markers to ensure that the plasmids are maintained in the cell.

What is claimed is:

1. A method for determining whether a first test protein interacts with a second test protein, the method comprising:

(a) providing a first population of mating competent cells, wherein a plurality of the cells of said population contain:
  (i) a first reporter gene operably linked to a first DNA binding protein recognition site; and
  (ii) a first fusion gene that expresses a first hybrid protein, said first hybrid protein comprising a test protein covalently bonded to a DNA binding moiety which specifically binds to said DNA binding protein recognition site;

(b) providing a second population of mating competent cells, wherein a plurality of the cells of said second population contain:
  (i) a second reporter gene operably linked to a second DNA binding protein recognition site; and
  (ii) a second fusion gene which expresses a second hybrid protein, said second hybrid protein coprising a second test protein covalently bonded to a gene activating moiety;

(c) mixing said first and said second populations of mating competent cells under conditions conducive to formation of mated cells; and (d) detecting expression of at least one reporter gene as a measure of the ability of the first test protein to interact with the second test protein, wherein said expressed reporter gene is said first or said second reporter gene or another reporter gene included in said first or said second mating competent cells or said mated cells, and is operably linked to either said first or second DNA binding protein recognition sites, and wherein said first fusion gene in said first population of mating competent cells is derived from a cDNA library.

2. The method of claim 1, wherein at least one of the reporter genes is selected from the group consisting of selectable reporter genes, counterselectable reporter genes, and selectable/counterselectable reporter genes.

3. The method of claim 1, wherein at least one of the reporter genes is a selectable reporter gene and at least one is a counterselectable reporter gene.

4. The method of claim 1, wherein at least one of the reporter genes is a selectable/counterselectable reporter gene.

5. The method of claim 1, wherein at least one of the reporter genes is a counterselectable reporter gene.

6. The method of claim 1, wherein the first and second DNA binding protein recognition sites are different.

7. The method of claim 1, wherein the first and second DNA binding protein recognition sites are identical.

8. The method of claim 1, wherein the first and second reporter genes are operably linked to identical promoters.

9. The method of claim 1, wherein the first and second reporter genes are operably linked to different promoters.

10. The method of claim 1, wherein at least one of the reporter genes is located on a plasmid.

11. The method of claim 1, wherein at least one of the fusion genes is located on a plasmid.

12. The method of claim 1, wherein at least one of the reporter genes is integrated into the genome of a plurality of the cells of the population of mating competent cells.

13. The method of claim 1, wherein expression of two reporter genes is detected.

14. The method of claim 1, wherein expression of three reporter genes is detected.

15. The method of claim 1, wherein the second test protein comprises a randomly generated sequence.

16. The method of claim 1, wherein the second test protein comprises an intentionally designed sequence.

17. The method of claim 1, wherein the first and second populations of cells are yeast cells.

18. The method of claim 1, wherein at least one of the reporter genes is selected from the group consisting of amino acid biosynthetic genes, nucleic acid biosynthetic genes, and antibiotic resistance genes.

19. The method of claim 1, wherein at least one of the reporter genes encodes a fluorescent protein.

20. The method of claim 1, wherein at least one of the reporter genes is selected from the group consisting of LEU2, HIS3, ADE2, TRP1, GFP, and lacZ.

21. The method of claim 1, wherein the DNA binding moiety comprises the DNA binding domain of a protein selected from the group consisting of GAL4, LexA, and Ace1.

22. The method of claim 1, wherein the gene activating moiety comprises the transcriptional activation domain of a protein selected from the group consisting of GAL4, VP16, and Ace1.

23. The method of claim 1, wherein at least one of the DNA binding protein recognition sites comprises at least one binding site for a protein selected from the group consisting of GAL4, LexA, and Ace1.

24. The method of claim 1, wherein each of the first and the second reporter genes is operably linked to 1 to 100 DNA binding recognition sites.

25. The method of claim 1, wherein at least one of the reporter genes is operably linked to a promoter that includes an upstream repressor sequence.

26. The method of claim 1, wherein at least one of the reporter genes is operably linked to a SPO13 promoter.

27. The method of claim 1, further comprising isolating a mated cell that expresses at least one of the reporter genes, thereby producing an isolated mated cell.

28. The method of claim 5, wherein the reporter genes are identical counterselectable reporter genes.

29. The method of claim 5, wherein the reporter genes are different counterselectable reporter genes.

30. The method of claim 5, wherein the counterselectable reporter gene is selected from the group consisting of URA3, LYS2, CYR2, CAN1, and GAL1.

31. The method of claim 5, wherein expression of the counterselectable reporter gene is detected as inhibition of cell growth.

32. The method of claim 7, wherein the reporter genes are different.

33. The method of claim 10, wherein the plasmid is a low copy number plasmid.

34. The method of claim 11, wherein the plasmid is a low copy number plasmid.

35. The method of claim 17, wherein the yeast cells are *S. cerevisiae* cells.

36. The method of claim 17, wherein cells of one of the populations of yeast cells are of the MATa mating type and cells of the other population of yeast cells are of the MATα mating type.

37. The method of claim 24, wherein each of the first and the second reporter genes is operably linked to 1 to 20 DNA binding recognition sites.

38. The method of claim 27, further comprising isolating plasmid DNA from the isolated mated cell.

39. The method of claim 27, further comprising amplifying at least a portion of a fusion gene of the isolated mated cell.

40. The method of claim 27, further comprising sequencing at least a portion of a fusion gene of the isolated mated cell.

41. The method of claim 27, further comprising hybridizing a probe to the DNA of the isolated mated cell.

42. The method of claim 32, wherein the first and second reporter genes are operably linked to different promoters.

43. A method for determining whether a first test protein interacts with a second test protein, the method comrising:
    (a) providing a first population of mating competent cells, wherein a plurality of the cells of said population contain:
        (i) a first reporter gene operably linked to a first DNA binding protein recognition site; and
        (ii) a first fusion gene, wherein the first fusion gene expresses a hybrid protein, said first hybrid protein comprising a first test protein covalently bonded to a DNA binding moiety which specifically binds to said DNA binding protein recognition site;
    (b) providing a second population of mating competent cells, wherein a plurality of the cells of said second population contain:
        (i) a second reporter gene operably linked to a second DNA binding protein recognition site; and
        (ii) a second fusion gene, wherein the second fusion gene expresses a second hybrid protein said second hybrid protein comprising a second test protein covalently bonded to a gene activating moiety;
    (c) mixing said first and said second populations of mating competent cells under conditions conducive to formation of mated cells; and
    (d) detecting expression of a reporter gene as a measure of the ability of the first test protein to interact with the second test protein, wherein said reporter gene is said first or said second reporter gene or another reporter gene included in said first or said second mating competent cells or said mated cells, and is operably linked to either said first or second DNA binding protein recognition sites, wherein said first fusion gene in said first population of mating competent cells is derived from a CDNA library and said second fusion gene in said second population of mating competent cells is derived from a CDNA library.

44. The method of claim 43, wherein at least one of the reporter genes is selected from the group consisting of selectable reporter genes, counterselectable reporter genes, and selectable/counterselectable reporter genes.

45. The method of claim 43, wherein at least one of the reporter genes is a selectable reporter gene and at least one is a counterselectable reporter gene.

46. The method of claim 43, wherein at least one of the reporter genes is a selectable/counterselectable reporter gene.

47. The method of claim 43, wherein at least one of the reporter genes is a counterselectable reporter gene.

48. The method of claim 43, wherein the first and second DNA binding protein recognition sites are different.

49. The method of claim 43, wherein the first and second DNA binding protein recognition sites are identical.

50. The method of claim 43, wherein at least one of the reporter genes is operably linked to a SPO13 promoter.

51. The method of claim 43, wherein the first and second reporter genes are operably linked to identical promoters.

52. The method of claim 43, wherein the first and second reporter genes are operably linked to different promoters.

53. The method of claim 43, wherein at least one of the reporter genes is located on a plasmid.

54. The method of claim 43, wherein at least one of the fusion genes is located on a plasmid.

55. The method of claim 43, wherein at least one of the reporter genes is integrated into the genome of a plurality of the cells of the first or second population of mating competent cells.

56. The method of claim 43, wherein expression of two reporter genes is detected.

57. The method of claim 43, wherein expression of three reporter genes is detected.

58. The method of claim 43, wherein the first and second populations of cells are yeast cells.

59. The method of claim 43, wherein at least one of the reporter genes is selected from the group consisting of amino acid biosynthetic genes, nucleic acid biosynthetic genes, and antibiotic resistance genes.

60. The method of claim 43, wherein at least one of the reporter genes encodes a fluorescent protein.

61. The method of claim 43, wherein at least one of the reporter genes is selected from the group consisting of LEU2, HIS3, ADE2, TRP1, GFP, and lacZ.

62. The method of claim 43, wherein the DNA binding moiety comprises the DNA binding domain of a protein selected from the group consisting of GAL4, LexA, and Ace1.

63. The method of claim 43, wherein the gene activating moiety comprises the transcriptional activation domain of a protein selected from the group consisting of GAL4, VP16, and Ace1.

64. The method of claim 43, wherein at least one of the DNA binding protein recognition sites comprises at least one binding site for a protein selected from the group consisting of GAL4, LexA, and Ace1.

65. The method of claim 43, wherein each of the first and the second reporter genes is operably linked to 1 to 100 DNA binding recognition sites.

66. The method of claim 43, wherein at least one of the reporter genes is operably linked to a promoter that includes an upstream repressor sequence.

67. The method of claim 43, further comprising isolating a mated cell that expresses at least one of the reporter genes, thereby producing an isolated mated cell.

68. The method of claim 47, wherein the reporter genes are identical counterselectable reporter genes.

69. The method of claim 47, wherein the reporter genes are different counterselectable reporter genes.

70. The method of claim 47, wherein the counterselectable reporter gene is selected from the group consisting of URA3, LYS2, CYH2, CAN1, and GAL1.

71. The method of claim 47, wherein expression of the counterselectable reporter gene is detected as inhibition of cell growth.

72. The method of claim 49, wherein the reporter genes are different.

73. The method of claim 53, wherein the plasmid is a low copy number plasmid.

74. The method of claim 54, wherein the plasmid is a low copy number plasmid.

75. The method of claim 58, wherein the yeast cells are *S. cerevisiae* cells.

76. The method of claim 58, wherein cells of one of the populations of yeast cells are of the MATa mating type and cells of the other population of yeast cells are of the MATα mating type.

77. The method of claim 65, wherein each of the first and the second reporter genes is operably linked to 1 to 20 DNA binding recognition sites.

78. The method of claim 67, further comparising isolating plasoid DNA from the isolated mated cell.

79. The method of claim 67, further comprising amplifying at least a portion of a fusion gene of the isolated mated cell.

80. The method of claim 67, further comprising sequencing at least a portion of a fusion gene of the isolated mated cell.

81. The method of claim 67, further comprising hybridizing a probe to the DNA of the isolated mated cell.

82. The method of claim 72, wherein the first and second reporter genes are operably linked to different promoters.

83. A method for determining whether a first test protein interacts with a second test protein, said method comprising:
   a) providing in a cell:
      i) at least three different reporter genes each operably linked to a DNA binding protein recognition site;
      ii) a first fusion gene which expresses a first hybrid protein, said first hybrid protein comprising a first test protein covalently bonded to a DNA binding moiety which specifically binds to said DNA binding protein recognition sites; and
      iii) a second fusion gene which expresses a second hybrid protein, said second hybrid protein comprising a second test protein covalently bonded to a gene activating moiety; and
   b) detecting expression of each of said reporter genes as a measure of the ability of said first test protein to interact with said second test protein.

84. The method of claim 83, wherein expression of each reporter gene is detected sequentially.

85. The method of claim 83, wherein expression of the at least three reporter genes is detected simultaneously.

86. The method of claim 83, wherein at least one of the reporter genes is a counterselectable reporter gene.

87. The method of claim 83, wherein said DNA binding protein recognition sites are identical.

88. The method of claim 83, wherein said DNA binding protein recognition sites are different, and said first hybrid protein comprises at least two different DNA binding moieties.

89. The method of claim 83, wherein at least one of the fusion genes is located on a plasmid.

90. The method of claim 83, wherein at least one of the reporter genes is integrated into the genome of said cell.

91. The method of claim 83, wherein said cell is a yeast cell.

92. The method of claim 83, further comprising isolating a cell which expresses each of said reporter genes.

93. The method of claim 83, wherein each of the different reporter genes is individually operably linked to a DNA binding protein recognition site.

94. The method of claim 86, wherein said counterselectable reporter gene is selected from the group consisting of URA3, LYS2, CYH2, CAN1, and GAL1.

95. The method of claim 87, wherein said reporter genes are operably linked to different promoters.

96. The method of claim 89, wherein said plasmid is a low copy number plasmid.

97. The method of claim 91, wherein said yeast cell is *S. cerevisiae*.

98. The method of claim 92, further comprising amplifying at least a portion of a fusion gene of said isolated cell.

99. The method of claim 92, further comprising sequencing at least a portion of a fusion gene of said isolated cell.

100. A method for determining whether a first and second test protein interact with a third test protein, said method comprising:
   a) providing in a cell:
      i) at least two different reporter genes each operably linked to a different DNA binding protein recognition site;
      ii) a first fusion gene which expresses a first hybrid protein, said first hybrid protein comprising a first test protein covalently bonded to a first DNA binding moiety which specifically binds to a first DNA binding protein recognition site;
      iii) a second fusion gene which expresses a second hybrid protein, said second hybrid protein comprising a second test protein covalently bonded to a second DNA binding moiety which specifically binds to a second DNA binding protein recognition site; and
      iv) a third fusion gene which expresses a third hybrid protein, said third hybrid protein comprising a third test protein covalently bonded to a gene activating moiety; and
   b) detecting expression of each of said reporter genes as a measure of the ability of said first and second test proteins to interact with said third test protein.

101. The method of claim 100, wherein at least one of the reporter genes is a counterselectable reporter gene.

102. The method of claim 100, wherein each of the different reporter genes is individually operably linked to a DNA binding protein recognition site.

103. A cell comprising:
   i) at least three different reporter genes each operably linked to a DNA binding protein recognition site;
   ii) a first fusion gene which expresses a first hybrid protein, said first hybrid protein comprising a first test protein covalently bonded to a DNA binding moiety which specifically binds to said DNA binding protein recognition sites; and
   iii) a second fusion gene which expresses a second hybrid protein, said second hybrid protein comprising a second test protein covalently bonded to a gene activating moiety.

104. The cell of claim 103, wherein at least one reporter gene is a counterselectable reporter gene.

105. The cell of claim 103, wherein said DNA binding protein recognition sites are identical.

106. The cell of claim 103, wherein said DNA binding protein recognition sites are different, and said first hybrid protein comprises at least two different DNA binding moieties.

107. The method of claim 103, wherein each of the different reporter genes is individually operably linked to a DNA binding protein recognition site.

108. A cell comprising a fusion gene which expresses a hybrid protein, said hybrid protein comprising a test protein covalently bonded to a gene activating moiety and C-terminal tag.

109. The cell of claim 108, wherein said C-terminal tag is a fluorescent protein or is a sequence which interacts with a second protein.

110. A cell comprising a fusion gene which expresses a hybrid protein, said hybrid protein comprising a test protein covalently bonded to a DNA binding moiety and a C-terminal tag.

111. The cell of claim 110, wherein said C-terminal tag is a fluorescent protein or is a sequence which interacts with a second protein.

112. A genetic construct comprising a first reporter gene operably linked to a first DNA binding protein recognition site and a second reporter gene operably linked to a second DNA binding protein recognition site, wherein said first and said second DNA binding protein recognition sites are different.

113. The genetic construct of claim 112, wherein at least one of the reporter genes is a counterselectable reporter gene.

114. A genetic construct comprising a fusion gene which expresses a hybrid protein, said hybrid protein comprising a test protein covalently bonded to a gene activating moiety and a C-terminal tag.

* * * * *